(12) United States Patent
Davies et al.

(10) Patent No.: US 8,926,984 B1
(45) Date of Patent: ***Jan. 6, 2015

(54) METHOD AND SYSTEM FOR HARVESTING MICRO ORGANISMS

(71) Applicant: Independence Bio-Products, Dublin, OH (US)

(72) Inventors: Christopher J. Davies, Longview, TX (US); John Russell Teague, Marshall, NC (US); Ronald A. Erd, Powell, OH (US)

(73) Assignee: Independence Bio-Products, Inc., Dublin, OH (US)

( * ) Notice: Subject to any disclaimer, the term of this patent is extended or adjusted under 35 U.S.C. 154(b) by 112 days.

This patent is subject to a terminal disclaimer.

(21) Appl. No.: 13/802,467

(22) Filed: Mar. 13, 2013

Related U.S. Application Data

(62) Division of application No. 13/158,085, filed on Jun. 10, 2011, now Pat. No. 8,458,952.

(60) Provisional application No. 61/354,083, filed on Jun. 11, 2010.

(51) Int. Cl.
*A61K 36/02* (2006.01)
*A01G 7/00* (2006.01)
*A01H 13/00* (2006.01)
*C12N 1/12* (2006.01)

(52) U.S. Cl.
CPC ........................................ *C12N 1/12* (2013.01)
USPC ....................... 424/195.17; 47/1.4; 435/257.1

(58) Field of Classification Search
None
See application file for complete search history.

(56) References Cited

U.S. PATENT DOCUMENTS

| | | | |
|---|---|---|---|
| 2,658,310 | A | 11/1953 | Cook |
| 2,867,945 | A | 1/1959 | Gattas |
| 3,431,200 | A | 3/1969 | Noah |
| 3,521,400 | A | 7/1970 | Ort |
| 3,645,040 | A | 2/1972 | Ort |
| 3,780,471 | A | 12/1973 | Ort |
| 4,005,546 | A | 2/1977 | Oswald |
| 4,137,868 | A | 2/1979 | Pryor |
| 4,209,388 | A | 6/1980 | DeFraites |
| 4,235,043 | A | 11/1980 | Harasawa |
| 4,258,661 | A | 3/1981 | Maghen |
| 4,267,038 | A | 5/1981 | Thompson |
| 4,320,594 | A | 3/1982 | Raymond |
| 4,910,912 | A | 3/1990 | Lowrey, III |
| 4,958,460 | A | 9/1990 | Nielson |
| 5,121,708 | A | 6/1992 | Nuttle |
| 6,615,767 | B1 | 9/2003 | Untermeyer |

(Continued)

OTHER PUBLICATIONS

Algaculture, http://en.wikipedia.org/wiki/Algaculture, 10 pages, last visited Jun. 18, 2012.

(Continued)

*Primary Examiner* — Chris R Tate
*Assistant Examiner* — Russell Fiebig
(74) *Attorney, Agent, or Firm* — Sci-Law Strategies, PC

(57) ABSTRACT

In an embodiment of the invention, aqueous growth medium in a pond can be used to grow algae which can be pumped to a primary dewatering device where the algae can be separated from the harvested growth media based on the flow of the harvested growth media and gravity. The flow through the primary de-watering device can be optimized to maintain log phase growth in the pond, while minimizing the pumping cost and maximizing the concentration of total solids in the primary de-watered algae.

20 Claims, 39 Drawing Sheets

(56) References Cited

U.S. PATENT DOCUMENTS

| | | |
|---|---|---|
| 6,740,232 B1 | 5/2004 | Beaulieu |
| 6,923,906 B2 | 8/2005 | Oswald |
| 7,905,049 B2 | 3/2011 | Erd |
| 2002/0034817 A1 | 3/2002 | Henry |
| 2005/0239182 A1 | 10/2005 | Berzin |
| 2007/0048848 A1 | 3/2007 | Sears |
| 2007/0289206 A1 | 12/2007 | Kertz |
| 2008/0009055 A1 | 1/2008 | Lewnard |
| 2008/0155890 A1 | 7/2008 | Oyler |
| 2009/0113790 A1 | 5/2009 | Erd |
| 2010/0093078 A1 | 4/2010 | Wang |

OTHER PUBLICATIONS

Belarbi, El Hassan, A process for high yield and scaleable recovery of high purity eicosapentaenoic acid esters . . . , Enzyme & Microbial Technology (2000), pp. 516-529, vol. 26.

Benemann, J.R., System & Economic Analysis of Microalgae Ponds . . . , Dept. of Energy Pittsburgh Energy Tech. Ctr. Under Grant No. DE-FG22-93PC93204 (Mar. 21, 1996), pp. 1-201.

Borowtiza, Michael A., Culturing Microalgae in Outdoor Ponds, Algal Culturing Techniques (2005), pp. 205-218, chap. 14, Academic Press.

Briggs, M., Widescale Biodiesel Production from Algae (revised 2004), Uni. of New Hampshire, Physics Department, 8 pages, http://www.unh.edu/p2/biodiesel/article_alge.html.

Chisti, Y., Biodiesel from microalgae, Biotechnology Advances (2007), pp. 294-306, vol. 25, Institute of Technology and Engineering, Massey University, NZ.

Goldberg, Highway or Country Road: Algal Recruitment with Distance . . . , J. Mar. Biol. Ass. U.K. (2004), pp. 879-882, vol. 84.

GPSI completes Algae to Biodeisel Winter Demo Testing, http://www.greenstarusa.com/news/08-08-3B.html (Mar. 25, 2008).

Grima, E. Molina et al., Recovery of microalgal biomass and metabolites: process options and economics, Biotechnology Advances (2003), pp. 491-515, vol. 20.

Grima, E. Molina, Microalgae, Mass Culture Methods, , Encyclopedia of bioprocess technology . . . (1999), pp. 1753-1769, vol. 3, University of Almeria, Almeria, Spain.

Manual on Production and Use . . . , Fisheries & Aquaculture Department, FAP Corporate Document Repository, www.fao.org/docrep/003/w3732e/w3732e06.htm, last visited Jun. 18, 2012.

MIT Algae Photobioreactor, http://www.youtube.com/watch?v=EnOSnJJSP5c (May 11, 2007).

Oil from Algae, http://www.oilalgae.com/algae/ap/ap.html, last visited Jun. 18, 2012.

Preliminary Patentability Report in PCT Application PCT/US2008/080674 (Dec. 2008).

Pulz, 0., Photobioreactors: production systems for photgraphic microorganisms, Appl Microbial Biotechnol (2001, published online Aug. 22, 2000), pp. 289-293, vol. 57.

Reisling, Thomas F., Ph.D., Cultivating Algae for Liquid Fuel Production (Sep. 4, 2007), 7 pages, http://www.oalkhavenpc.org/cultivating_algae.htm.

Sazdanof, N., Modeling & Simulation of the Algae to Biodiesel Fuel Cycle, Honors Undergraduate Theses (2006), Submitted to College of Engineering Honors Comm., Ohio State Uni.

Schirmer A. et al., Microbial Biosynthesis of Alkanes, Science (2010), pp. 559-562, vol. 329.

Search report in PCT Application PCT/US2008/08067 4 (Dec. 29, 2008).

Sheehan, J. et. al., A Look Back at the U.S. Department of Energy's Aquatic Species Program: Biodiesel from Algae—Part 1 Program Summary (Jul. 1998).

Shelef, Get al., DE840130036, Microalgae Harvesting and Processing: A Literature Review (Aug. 1984),SER1./STR-231-2396.

Spolaore, P. et al., Review: Commercial Applications of Microalge (2006), J. Bioscience and Bioengineering, No. 2, pp. 87-96, vol. 101.

Terry, Kenneth L., System design for the autotrophic production of microalgae, Enzyme Microb. Technol. (Oct. 1985), pp. 474-487, vol. 7.

Tredici, Mario R., Bioreactores, Photo, Encyclopedia of bioprocess technology . . . (1999), pp. 395-419, vol. 1, University of Florence, Florence, Italy.

Wijffels, R.H. et al., An Outlook on Microalgal Fuels, Science (2010), pp. 796-799, vol. 329.

Wilde, E.W. et. al, Cultivation of algae and nutrient removal in a waste heat utilization process; J. of Appl. Phycology (1991), pp. 159-167, vol. 3, Kluwer Acad. Pub., Belg.

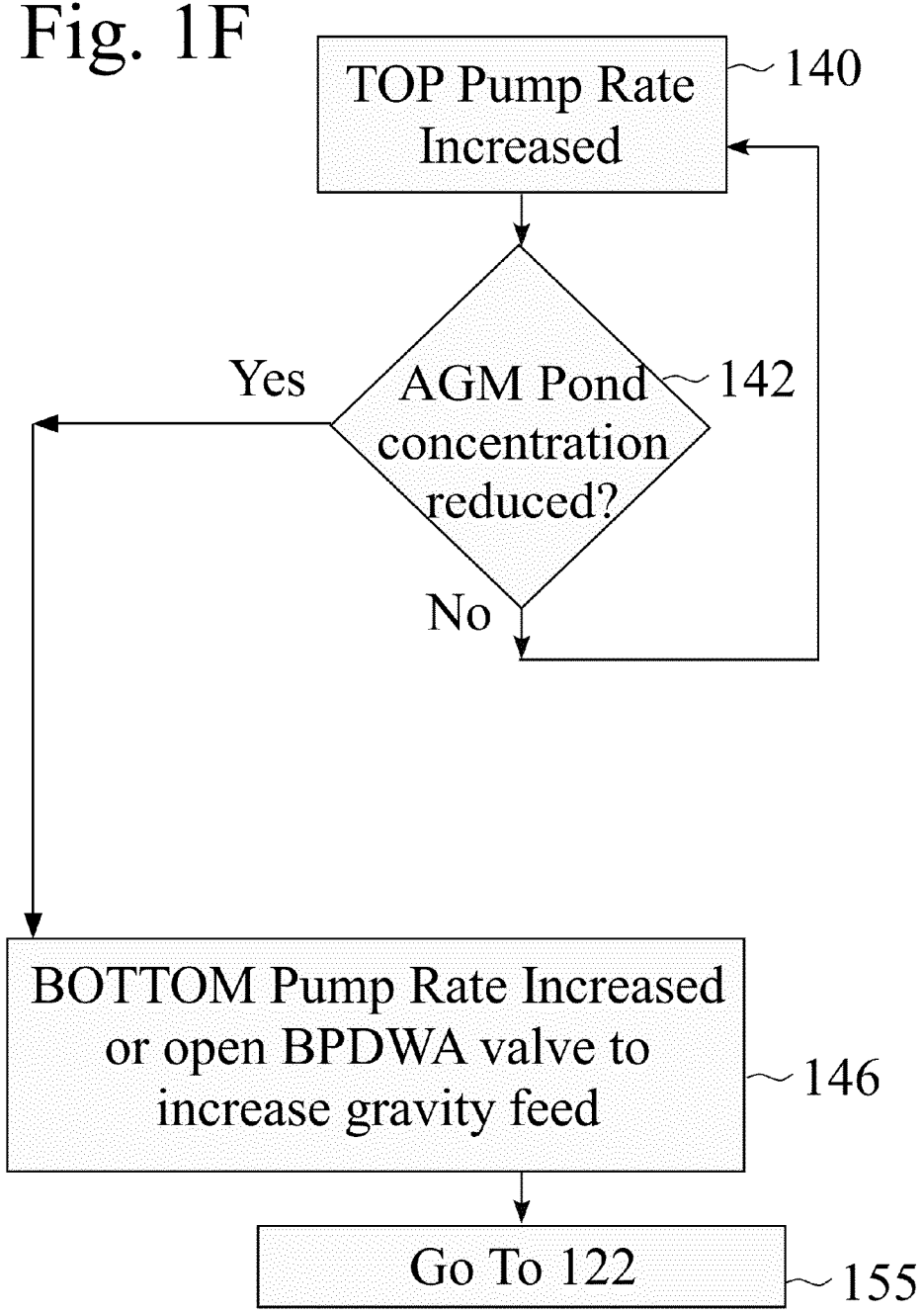

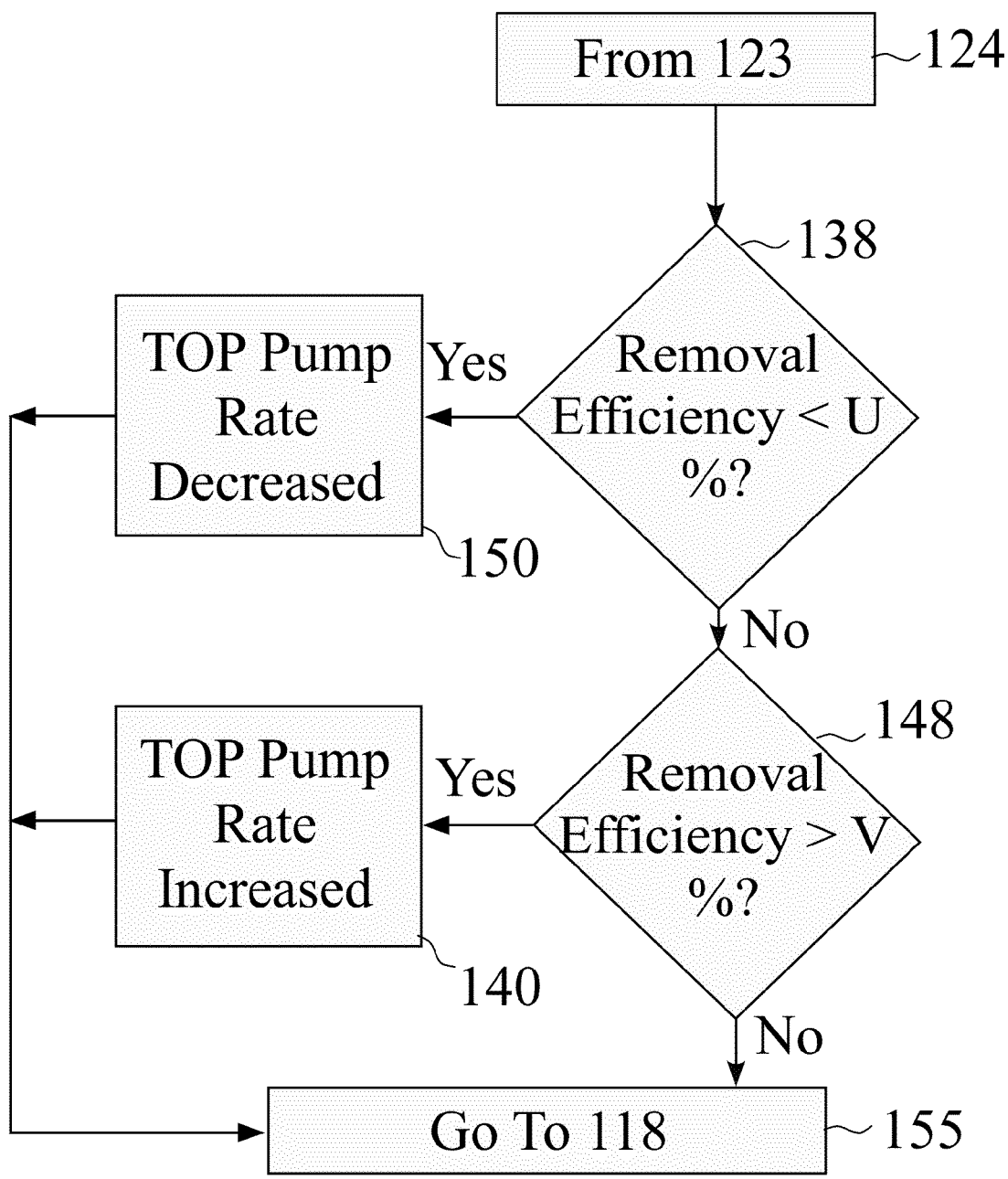

METHOD AND SYSTEM FOR HARVESTING MICRO ORGANISMS

PRIORITY CLAIM

This application is a divisional of U.S. application Ser. No. 13/158,085 entitled "Method and System for Harvesting Micro Organisms" by Christopher J. Davies et al. and filed Jun. 10, 2011, which issued Jun. 11, 2013 as U.S. Pat. No. 8,458,952, which claims priority to the U.S. Provisional Application No. 61/354,083, entitled "Method and System for Harvesting Micro Organisms" by Christopher J. Davies et al. filed Jun. 14, 2010. These applications are herein expressly incorporated by reference in their entireties.

CROSS REFERENCE TO RELATED APPLICATION

This application is related to the following application: (1) U.S. Utility patent application Ser. No. 11/993,743, entitled "Algae Production" by Ronald A. Erd, filed Nov. 1, 2007, which issued as U.S. Pat. No. 7,905,049, and (2) U.S. Utility patent application Ser. No. 13/020,996, entitled "Algae Production" by Ronald A. Erd, filed Feb. 4, 2011. These applications (1)-(2) are herein expressly incorporated by reference in their entireties.

FIELD OF THE INVENTION

This invention relates to a method and system of harvesting micro organisms from a pond.

BACKGROUND OF THE INVENTION

Microalgae can range from approximately 1 μm to greater than 200 μm in size. Some microalgae form chains or colonies of multiple cells. The composition of algae includes lipids, carbohydrates, ribonucleic acids and proteins. Algae typically require sunlight, water, carbon dioxide and other nutrients in order to grow. The surfaces of algae include negative charges due to the presence of mannuronic acid, β-L-glucuronic acid, β-D-xylosyl, alginic acid and sulfonated polysaccharide residues. The exact composition of the cell walls varies with algae species and conditions of growth.

Culture of microalgae can be practiced for production of hydrocarbons, synthesis of a source of protein, generation of a number of organic substances, wastewater treatment, solar energy conversion and combinations of the these processes. Nutrient supplements rich in carbon dioxide, nitrogen and phosphorous can significantly increase growth rates of algae. Addition of metal ions which generate metal hydroxides can minimize dispersion forces leading to flocculation. Alternatively, high molecular weight organic polymers can flocculate algae by forming a network of bridges. Addition of flocculants into culture medium in order to induce flocculation is a routine procedure in waste water treatment.

Algae solid-aqueous liquid separation processes include screening, filtration (cake filtration and deep bed filtration), micro strainers, sedimentation, flotation, gravity and centrifugation (fixed wall and rotating wall). Wastewater treatment involves the lowering of the suspended solids to a level acceptable for discharge of the water without causing deleterious effects on the ecology of the discharge area.

Sedimentation is a physical water treatment process used to settle out suspended solids in water under the influence of gravity. For example, a water clarifier can be used in the metal finishing industry to remove metal ions from waste water. Alternatively, sedimentation can be used as a primary stage in modern waste water treatment plant, reducing the content of suspended solids as well as pollutants embedded in the suspended solids. Remaining suspended solids can be reduced by chemical coagulation and flocculation in subsequent steps.

SUMMARY OF THE INVENTION

In an embodiment of the present invention, a fractionation tank fed by a system to culture algae can be used to separate the size of algae in a media to harvest the large cells while returning the smaller less mature size cells to the system to culture more algae and to allow further time for growth of the less mature cells. In this embodiment of the invention, the top primary de-watered media being returned to the system to culture algae is not apparently different from the harvested growth media being fed into the fractionation tank. That is the fractionation tank does not appear to be purifying or clarifying the harvested growth media even though algae does accumulate at the bottom of the fractionation tank. Using appropriate criteria to regulate the pumping flow rate allows bottom primary de-watered algae to be harvested from the fractionation tank. In an embodiment of the present invention, the bottom primary de-watered algae can be recovered from the harvested growth media while the aqueous growth media can be returned to the pond to encourage the algae to continue to grow. In an embodiment of the present invention, a method of generating primary de-watered algae comprises a system to culture algae containing aqueous growth media, a primary de-watering device, means for transporting the growth media to be harvested to the primary dewatering device and a flow control device. The growth media to be harvested includes one or more species of algae, wherein the concentration of the one or more species of algae in the system can be used to calculate the harvested growth media concentration. The primary de-watering device separates the harvested growth media into the top primary de-watered algae and the bottom primary de-watered algae, wherein the primary de-watering device includes an entrance for the growth media to be harvested, a first exit for the top primary de-watered algae and a second exit for the bottom primary de-watered algae. In an alternative embodiment of the invention, a flow control device regulates the flow of aqueous growth medium. In an embodiment of the invention, harvested growth media is transported from a system to culture algae into a primary de-watering device, wherein a flow control device regulates a top primary de-watered algae concentration relative to a growth media to be harvested concentration between a lower limit of approximately 5% and an upper limit of approximately 75%.

In an embodiment of the present invention, a method is provided for the separation of algae from growth media to be harvested, the method comprising introduction of the growth media to be harvested to a fractionation tank comprising an inlet for the growth media to be harvested, an outlet for the top primary de-watered algae, one or more surfaces to accelerate algae settling, wherein the configuration of the inlet for the growth media to be harvested and the outlet for the top primary de-watered algae allows for enhanced interaction of the introduced growth media to be harvested to the one or more surfaces. In an embodiment of the invention, the method further comprises the removal of bottom primary de-watered algae with minimal disruption of algae that has settled. In an embodiment of the invention, the method further comprises an outlet by which the bottom primary de-watered algae can be removed. In an embodiment of the invention, the method further comprises using the growth media to be harvested from which algae have been removed for seeding further algaculture.

In an alternative embodiment of the invention, a flow control device regulates the flow of aqueous growth medium. In an embodiment of the invention, harvested growth media is pumped from the pond into the primary de-watering device, wherein the flow control device regulates the top primary de-watered algae concentration relative to the harvested growth media concentration between a lower limit of approximately 5% and an upper limit of approximately 75%. In another embodiment of the invention, harvested growth media is pumped from the pond into the primary de-watering device, wherein the flow control device regulates the top primary de-watered algae concentration relative to the harvested growth media concentration between a lower limit of approximately 75% and an upper limit of approximately 95%.

BRIEF DESCRIPTION OF THE DRAWINGS

This invention is described with respect to specific embodiments thereof. Additional features can be appreciated from the Figures in which:

FIG. 1(F) is a flowchart showing a procedure used to increase the TOP pump rate as required in the flowcharts shown in FIG. 1(B), FIG. 1(E) and FIG. 1(H) according to various embodiments of the invention;

FIG. 1(K) is a flowchart showing a procedure used to optimize primary de-watering of GMH based on the removal efficiency according to an embodiment of the invention;

DETAILED DESCRIPTION OF THE INVENTION

Definitions

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

As used herein, the term "fractionation" is defined as 'separating into parts based on the density' and in a specific embodiment of the invention as 'separating the algae in the medium based on the density of the algae'. A "fractionation tank" or "fractionation stage" are used to describe a device or stage for a primary de-watering process where less than 75% of the algae in the medium is removed from the medium.

The term "optical density (OD)" is a measure of the amount of light transmitted through a medium in a visible spectrometer at 600 nm. This measure of the concentration of algae in media will vary depending on the settling time of the algae in the media under the conditions used. Thus using the fractionation tank conditions with different strains of algae will give a range of optical densities based on the varying settling times of the algae. The term approximately when used before the OD will be used to indicate that the measurement encompasses lower and higher OD's due to this settling effect. The term "total solids (TS)" refers to the weight of solids recovered after drying the medium. In contrast to the OD, the TS measurement can be a more absolute measurement of the amount of algae in media.

Figure 19:
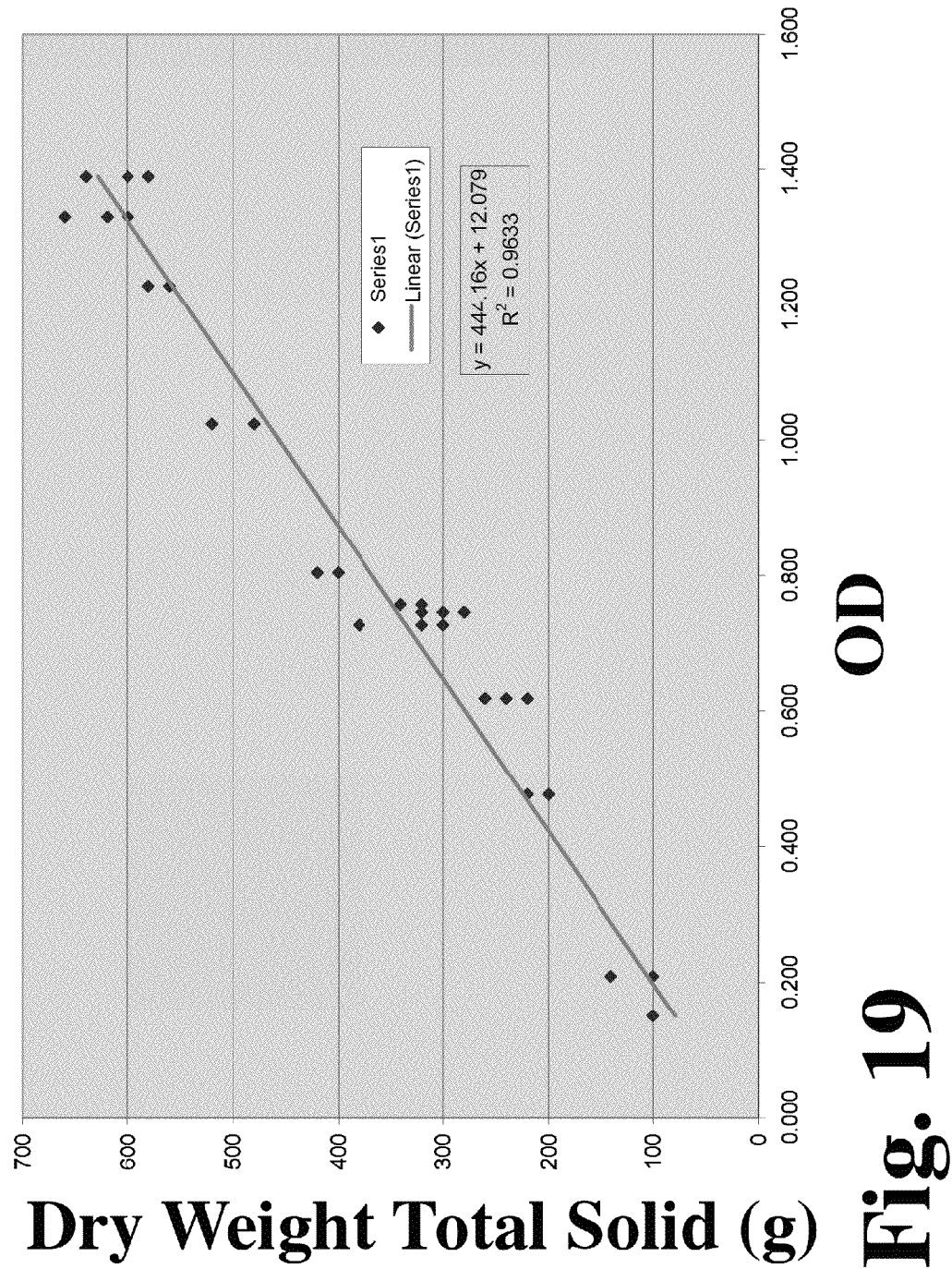
FIG. 19 shows the correlation between the optical density (OD measurements and total solids (TS) measurements for dry weight algae.

The OD measurements generally correlate well with cell counting estimates of the media, as shown in Table I, where trends observed in the cell counts are reflected in the OD measurements. It is noted that because the variation in size of algae is not taken into consideration when counting the number of cells, it is possible that some of the variation observed in Table I reflects actual differences between the media measured using light absorption versus cell counting. The OD measurements also correlate well with the TS measurements for dry weight algae, as shown in FIG. 19.

The term "algae or aqueous growth medium (AGM)" refers to the medium used to grow algae which can range from 0-4 OD". The term "primary de-watering device (PDWD)" refers to a device used to increase the concentration of the algae in the medium. The term "growth media to be harvested (GMH)" refers to the AGM after it has entered the PDWD. In various embodiments of the invention, the GMH ranges from approximately 0.5-4 OD. The term "secondary de-watering device (SDWD)" refers to a device used to further increase the concentration of the algae in the media.

Table I

Comparison of the OD measurements with Cell Count measurements for Algae Growth Media (AGM)

| Days | OD (at 600 nm) | Cell Counts ($\times 10^5$) |
|---|---|---|
| 4 | 0.65 | 297 |
| 6 | 0.73 | 421 |
| 6 | 1.03 | 656 |
| 7 | 0.92 | 379 |
| 8 | 0.73 | 400 |
| 8 | 0.81 | 241 |
| 9 | 0.92 | 300 |
| 10 | 1.25 | 593 |
| 11 | 1.12 | 549 |

The term "primary de-watered algae medium (PDWA)" refers to the product of the process that fractionates the GMH. The term top PDWA (TPDWA) refers to the medium that is less concentrated than the GMH after the fractionation process of the PDWD. In an embodiment of the invention, the TPDWA is returned to the system used to culture algae. The term "bottom PDWA (BPDWA)" refers to the medium that is more concentrated than the GMH after the fractionation process of the PDWD. In an embodiment of the invention, the BPDWA can be sent to a secondary de-watering step.

In some embodiments of the invention that use an intrachannel PDWD there is little or no difference between the AGM and the GMH at the point where the AGM flows into the PDWD. Even in these cases the term AGM will be used to identify the inflow into the PDWD whereafter the flow will refer to GMH until the TPDWA exits the PDWD to return to the open channel pond as AGM.

The term "bottom SDWA (BSDWA)" refers to the product that is more concentrated than the BPDWA after the process of the SDWD. The BSDWA can range from approximately 10-40% TS. The term "top SDWA (TSDWA)" refers to the medium that is less concentrated than the BSDWA after the process of the SDWD. The TSDWA can be returned to the pond.

The term "log phase growth" refers to the growth phase of algae after the initial 'lag phase' when the algae are multiplying exponentially by cell division. The term 'stationary phase' refers to the phase of algae growth after log phase where growth is attenuated, which can be caused by depletion or accumulation of products.

The term "pond" is used to refer to a body of water which can include an ocean, a sea, a lake, a river, a stream or a man made structure that holds a body of water with a volume in excess of 100 m$^3$. The term "open pond" is used to refer to a pond in direct contact with the atmosphere.

The term "biomass recovery" is used to refer to the amount of BPDWA collected from the fractionation tank. The biomass recovery is dependent on the rate of flow of the GMH, the concentration of the GMH, the type of algae, the phase of growth of the algae, and the settling characteristics of the algae.

The term "settling time" is used to indicate the time the GMH is allowed to fractionate in the PDWD which can be calculated based on the flow rate into the PDWD and the volume of the PDWD.

The term "flotation characteristics" refers to the buoyancy of the algae. The flotation characteristics can depend on a number of parameters including the species of algae, the growth phase of the algae, the concentration of algae, the concentration of flocculants in the growth media, the temperature of the media and the presence and intensity of sunlight.

The term "paddle" refers to a device used to move all or a portion of the body of water contained in the pond. A paddle includes a mixer, a turbine, a fan, a wheel, an auger, a pump or other device which can induce a flow in the AGM in the pond.

The term "reseeding" refers to the addition of less mature micro organism cells to an aqueous growth medium in order to grow the micro organism.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without some or all of the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes.

The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

The intensity of the negative charge of algal surfaces is a function of at least the ionic strength of the aqueous algae medium, the pH, the presence of polysaccharides, the presence of ammonium sulfate, the presence of auto-flocculants and algae absorption of ions from the aqueous medium. The electro negativity has been shown to increase as the algae grow. The propensity to flocculate has been attributed to one or more of the electro negativity of the algae, the counter ions present on the algae and exuded agents synthesized by the algae. The stability of aqueous algae medium can depend on a number of parameters including the negative charge on the algae cell surfaces, the algae cell dimensions, the algae cell density, the nature of counter ions present on the algae cell wall, the ionic strength of the solution, and the presence of an algae exudate. In an embodiment of the invention, metal ions can be added which generate metal hydroxides which can minimize dispersion forces leading to flocculation of the algae. Alternatively, high molecular weight organic polymers can flocculate algae through a bridging action. In an embodiment of the invention, algal flocculants can be added into algae cultures in order to induce flocculation. Both of these means to flocculate algae involve the addition of chemicals which can be undesirable for a continuously growing pond and can lead to deleterious or uncontrolled effects on the sustained algae growth.

An important first step in the processing of cultivated algae for commercial purposes is the separation of the algae from the aqueous medium in which it is grown. That is, the efficient separation dewatering and drying of microalgae can determine the economic feasibility of any microalgae production system. This separation and de-watering step is usually achieved by centrifugation. Due to the relatively low concentration of algae in the medium, dewatering by centrifugation is inefficient and energy intensive. Therefore the expense can become a prohibitive cost. In an embodiment of the invention, the method provides a cost efficient means of producing algae.

Primary De-Watering

In an embodiment of the invention, a method of pre-concentrating the GMH can be used prior to a secondary de-watering step. In an embodiment of the invention, a method of primary de-watering the GMH can be used prior to a secondary de-watering step. In an embodiment of the invention, an effective method of primary de-watering the GMH can use a fractionation tank to settle and collect the fractionated algae prior to secondary de-watering. In an embodiment of the invention, a fractionation step can be an energy efficient method of primary de-watering the GMH. In an embodiment of the invention, a fractionation step can be a cost effective method of primary de-watering the GMH.

Algae solid-aqueous liquid separation processes include screening, filtration (cake filtration and deep bed filtration), micro strainers, sedimentation, flotation, gravity and centrifugation (fixed wall and rotating wall). Screening relies upon passing the aqueous algae medium through a screen of given aperture size. Microstrainers and vibrating screen filters have been used to separate algae. Filtration relies upon a pressure drop for the aqueous algae medium to pass through the filtrate. The pressure can be applied by gravity, vacuum, pressure and centrifugal forces. Filtration techniques typically requires backflushing to release bound algae. Microstrainers consist of a rotary drum covered by a straining fabric, stainless steel or polyester. A backwash spray collects the particles onto an axial trough. High gradient magnetic filtration has been used for the removal of suspended particles and heavy metals from wastewater. In an embodiment of the invention, gravity sedimentation can separate the aqueous algae medium into a slurry of higher concentration and an effluent of substantially clear liquid.

Clarifiers can utilize gravity in conjunction with passing the liquid over parallel plates to settle solids from a liquid flow. The liquid inflow can be pre-treated. Next the liquid can be transferred into a flocculation tank where flocculent is added to promote flocculation. In the flocculation tank, the liquid can move up through a series of plates where the solids can separate out from the liquid and settle to form sludge at the bottom of the clarifier. The clean water can be directed out through laundering troughs for polishing and water reuse or simply as 'cleaned' waste. The solids are typically taken from the sludge cones to be discarded.

The advantage of a clarifier when treating waste water is that the process uses gravity and water flow to separate particulate matter. Clarifiers have previously been used to help meet Environmental Protection Agency guidelines and to meet solid discharge requirements relating to metal finishing wastes and water municipal wastes.

In an embodiment of the invention, a clarifier tank can be used as a fractionation tank. In an embodiment of the invention, a fractionation tank without settling plates can be used to fractionate solids dispersed in a flowing liquid. The rate of flow of the GMH into the fractionation tank equals the rate of flow of TPDWA out through the outlets plus the rate of flow of BPDWA out through the outlets. Further, the average residence time of the GMH within the fractionation tank is determined primarily by the flow rate of GMH into the inlet and the volume of the fractionation tank. In an embodiment of the invention, the sedimentation of the BPDWA from the GMH depends on the channeling of the GMH entering the fractionation tank and the subsequent flow and turbulence characteristics of the GMH.

In an embodiment of the invention, TPDWA from which some but not all algae have been removed can be re-used for algaculture. In an embodiment of the invention, TSDWA from which some but not all algae have been removed can be re-used for algaculture. In an embodiment of the invention, the TPDWA can be recycled back to the open system used to culture algae. In an embodiment of the invention, the TSDWA can be recycled back to the system used to culture algae. In an embodiment of the invention, the fractionation tank can utilize gravity in conjunction with parallel 'settling plates' to settle solids from a liquid flow. In various embodiments of the invention, the settling plates can be made of one or more materials selected from stainless steel, steel, tar coated steel, epoxy coated steel, polyethylene, polyester and a non corrosive substance. In an embodiment of the invention, the fractionation tank can utilize gravity without settling plates to settle solids dispersed in a flowing liquid.

Measurements made returning the TPDWA to the pond found that not only was the TPDWA ideally conditioned with nutrients to grow the selected species of algae, but the TPDWA also carried the correct developmental stage algae to keep the pond in log phase growth when the GMH was being pumped at an appropriate rate. It was unexpected that the fractionation tank can return the media to the pond where the algae was sized based on the absence of settling. It was also unexpected that the returned algae can be ideal reseeding feedstock for producing further algae in the pond. It was also an unexpected result that an intrachannel fractionation stage can return the TPDWA to the pond where the algae was sized based on the absence of settling. It was also an unexpected result that the returned algae can be ideal reseeding feedstock for producing further algae in the pond. By eliminating the pumping of AGM to a PDWD, the costs of the algae harvesting can be significantly reduced. However, it was unexpected that the algal growth rates could be increased by using an intrachannel fractionation stage. The increased growth rates were attributed to the increased exposure of the TPDWA to seeded medium and sunlight using an intrachannel fractionation stage as no pumping of AGM in piping was required. It was noted that while resident in the piping the AGM is receiving less nutrients, less dissolved carbonates and less sunlight. The level of nutrients was expected to drop off with the distance that the AGM was piped from the nutrient source in the pond. The increased growth rates were also attributed to a lesser extent to the reduced handling of the reseeding algae when little or no pumping in piping was required.

In an embodiment of the invention, the fractionation tank can be operated at a flow rate too rapid to allow clarification of the GMH but can act to size fractionate the algae. In an embodiment of the invention, significant algae can settle at flow rates below 60 GPM. It was an unexpected result that the fractionation tank can also be used to affect a sizing of the algae extracted from the media based on the settling time for the algae where the residence time of the media in the fractionation tank was less than approximately two hours.

The flow rate through the fractionation tank with return of the TPDWA to the pond has multiple effects depending on the state of the pond. A faster flow rate decreases residence time and thereby nominally decreases removal efficiency (OD reduction from GMH to TPDWA). Normally, it is expected that a fast rate of flow can be utilized to assist the growth of the algae by returning more algae to the pond and only removing the most dense or fastest settling algae. Normally, a slower rate of flow can be used to harvest algae, where all but the less dense or slower settling algae can be removed.

However, the mass of the material removed can be dependent on the concentration and stage of growth of the algae in addition to the rate of the water moving through the fractionation tank. In various embodiments of the invention, at a flow rate of 10 GPM, the OD of the GMH going to the TPDWA can change from 1.0 to 0.5. Unexpectedly, for the same pond (i.e., the same concentration, stage of growth and species of algae) at a flow rate of 100 GPM, with the OD of the GMH going to the TPDWA can change from 1.0 to 0.8. That is, unexpectedly the fractionation tank can harvest significantly more material at a faster flow rate. Accordingly, in an embodiment of the invention, as the OD in the pond increases, the GMH flow rate can be increased. In an embodiment of the invention, a GMH flow rate that is too slow can result in the OD in the pond increasing. This is an unexpected result based on the normal expectations outlined above. It is counter intuitive that more material is removed at the faster flow rate and less material is removed at a slower rate. This observation also reflects the critical balance between flow rate and the growth rate of the algae in the pond. It is also counter intuitive that removal of more material from the GMH allows maintenance of the GMH in an appropriate growth rate.

In an embodiment of the invention, the larger and/or denser algae is more suitable for extracting and refining oil. In an embodiment of the invention to maximize growth, the pond GMH concentration was held within a desired range and the difference between the GMH and the TPDWA was adjusted with the flow rate. In this manner, the TPDWA concentration relative to the GMH concentration can be initially approximately 5% and thereafter be increased to approximately 75%. At a subsequent time this ratio can vary between 5 and 75%, depending on the condition of the algae growth in the pond.

In an embodiment of the invention, the aqueous growth medium (AGM) is typically approximately 0-4 OD (optical density). In an embodiment of the invention, GMH is typically approximately 0.5-4 OD. In an embodiment of the invention, pumping of the GMH can begin as soon as the pond has been seeded with the algae. In this embodiment, the pumping rate can be very fast (120 GPM or greater) to insure that the algae is not significantly harvested initially. In an alternative embodiment of the invention, pumping of the GMH begins when the GMH reaches 0.2 OD. In this embodiment, the pumping rate can be reasonably fast (approximately 80 GPM) to insure that the algae is not over harvested initially. In another embodiment of the invention, pumping of the GMH begins when the GMH reaches 0.5 OD. In an embodiment of the invention, an interval of time of approximately seven days can be required before the concentration of the algae in the AGM has reached a sufficient level for harvesting. In an alternative embodiment of the invention, an interval of time of approximately ten days can be required before the concentration of the algae in the AGM has reached a sufficient level for harvesting. In another embodiment of the invention, an interval of time of approximately fourteen days can be required before the concentration of the algae in the AGM has reached a sufficient level to make harvesting worthwhile. In an embodiment of the invention, an interval of time of approximately fourteen days after seeding can be required before log phase growth occurs. In an embodiment of the invention, a fractionation tank can be used to preconcentrate growth media to be harvested as shown in Table II. Table II shows that the primary dewatering step operates with approximately 8-41% efficiency. In various embodiments of the invention, the primary de-watering can operate with an efficiency of between 10-60%. A fractionation tank can be used to preconcentrate the bottom primary de-watered algae from the GMH to 0.7-10% TS. In an embodiment of the invention, further drying can be carried out on the BPDWA. In an embodiment of the invention, after secondary de-watering a BSDWA can yield approximately 10-60% TS.

TABLE II

Comparison of GMH and TPDWA Algae Concentrations

| GMH Concentration (OD) | TPDWA Concentration (OD) | Reduction (OD) | Flow Rate (GPM) |
| --- | --- | --- | --- |
| 0.81 | 0.69 | 15 | 70 |
| 0.9 | 0.7 | 23 | 50 |
| 0.92 | 0.85 | 8 | 65 |
| 1.2 | 1.0 | 17 | 50 |
| 1.2 | 0.9 | 25 | 50 |
| 1.2 | 0.9 | 25 | 50 |
| 1.7 | 1.0 | 41 | 50 |

Figure 1A:
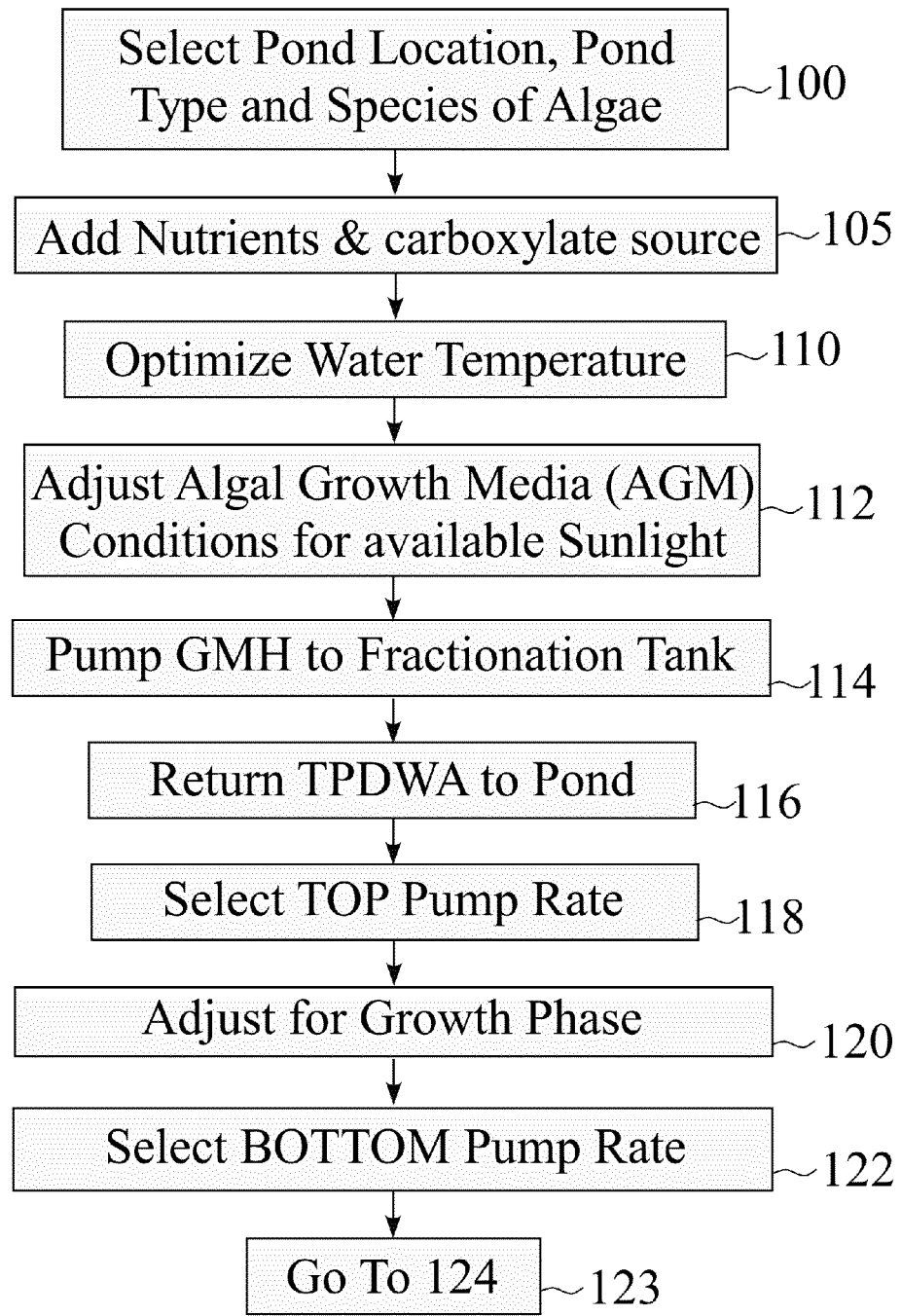
FIG. 1(A) is a flowchart showing the procedure used to optimize growth of one or more selected species of algae in a pond according to an embodiment of the invention.

As shown in FIG. 1A, the location, the pond type, the pond size selected and the specie or species of algae can be selected 100. Nutrients and one or more carboxylate sources such as dissolved $CO_2$ can then be added 105. Based on the species selected, the water temperature can be optimized 110. The algae growth media (AGM) conditions can be adjusted for the available sunlight and algae concentration 112. Next the GMH TOP can be pumped to the fractionation tank 114. The TPDWA can be returned to the pond 116. Next the TOP pump rate for the GMH can initially be selected based on the concentration of the AGM 118. In various embodiments of the invention an initial TOP pump rate of 50 GPM can be selected. The TOP pump rate can be optimized to keep the algae growing in the appropriate phase 120. The BOTTOM pump rate can be adjusted to maximize harvesting 122. The process outlined in FIG. 1A can be optimized according to one or more of the schemes set out in FIGS. 1B-1K, as shown at 123.

Figure 2A:
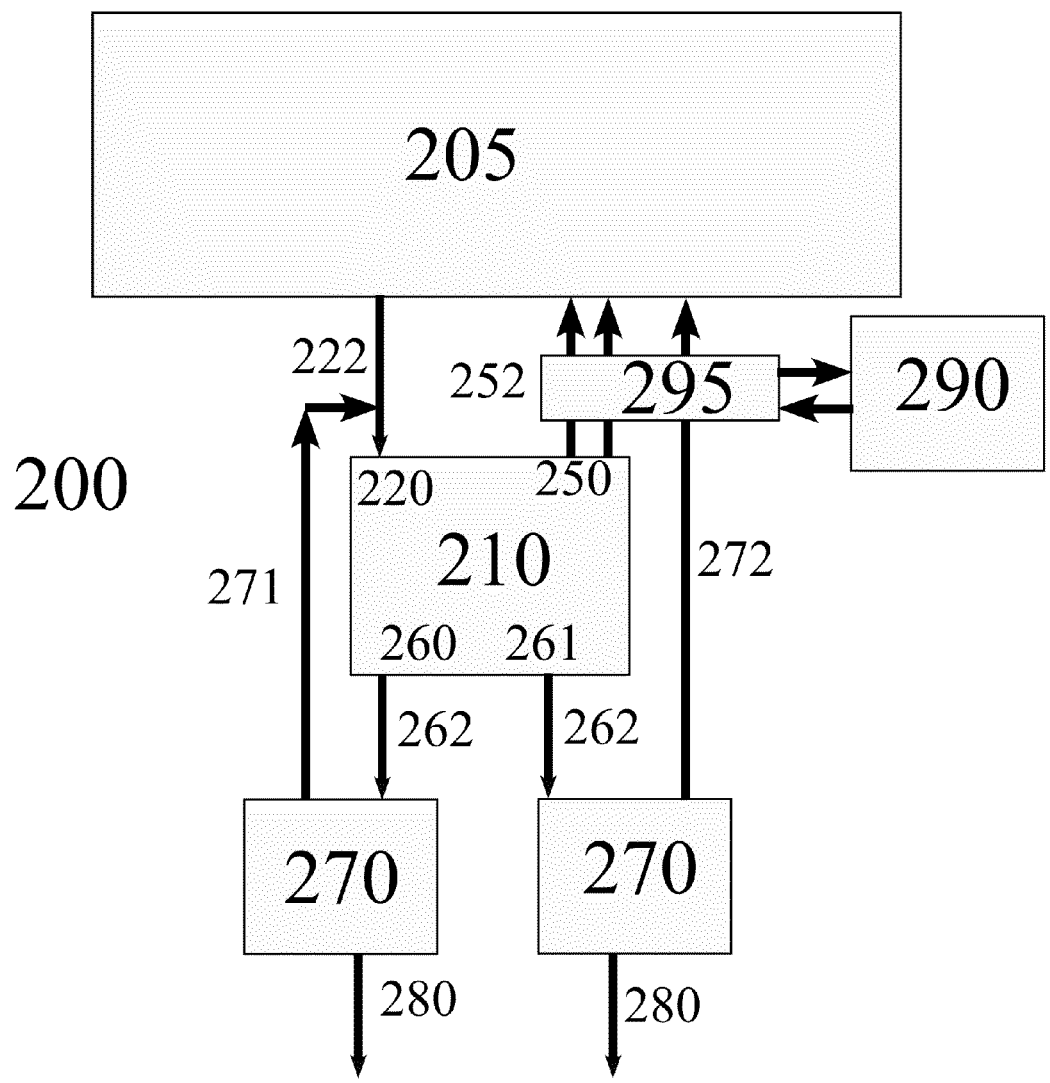
FIG. 2(A) is a schematic drawing of the pond, the fractionation tank and the secondary de-watering device according to an embodiment of the invention.

In an embodiment of the invention, shown in FIG. 2A, the AGM from the pond 205 is pumped to the fractionation tank 210. The GMH 222 enters the fractionation tank 210 at inlet 220. The TPDWA 252 exits the fractionation tank at 250 to be returned to the pond 205. The BPDWA 262 exits the fractionation tank at 260 and 261 to be sent to one or more secondary dewatering devices 270. The BSDWA 280 is removed from the secondary dewatering devices 270. The TSDWA 280 retrieved from the secondary dewatering devices 270 can either be treated as GMH 222 and fed into the fractionation tank 210 or returned 272 to the pond 205.

Figure 2B:
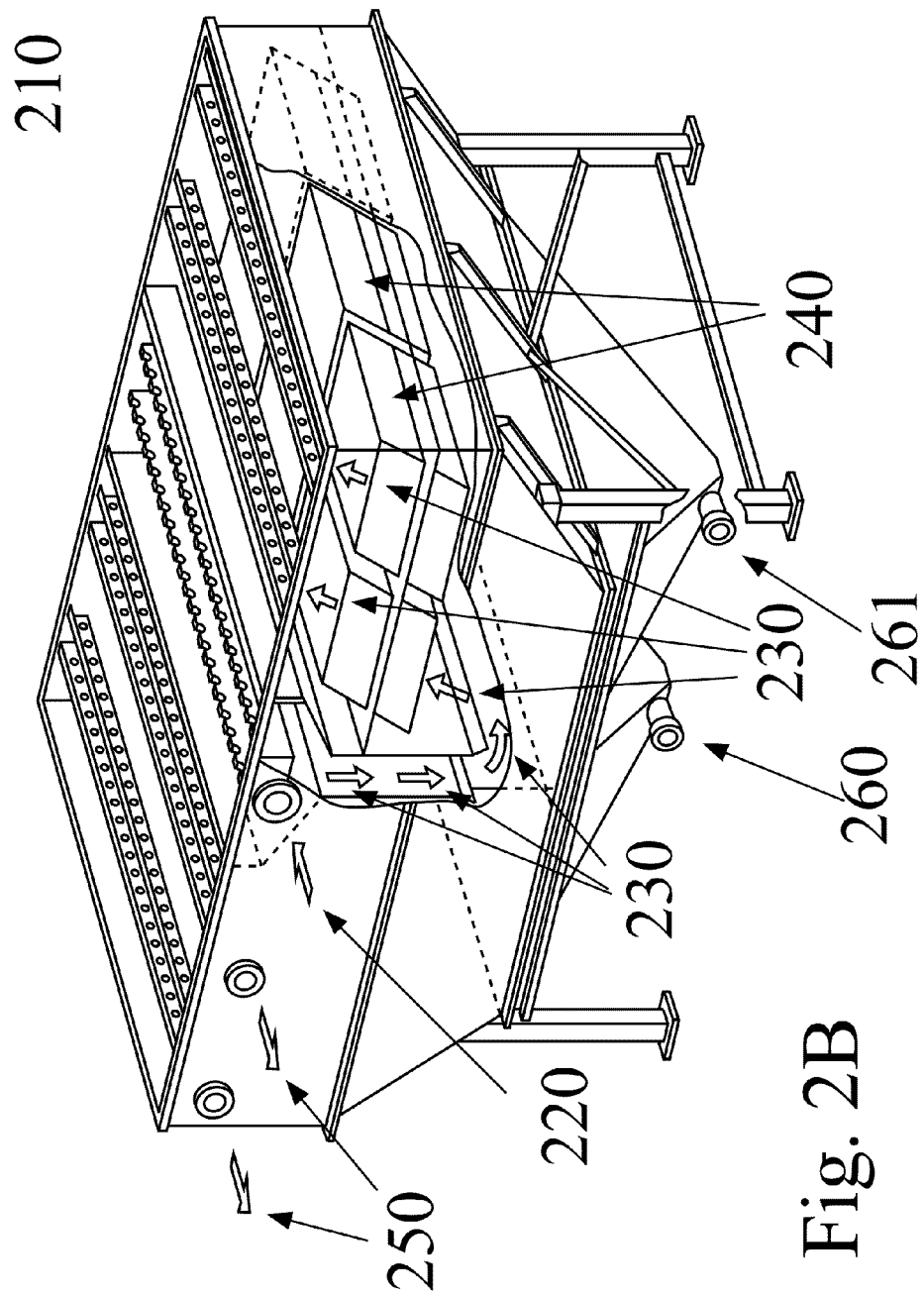
FIG. 2(B) is a line drawing of a fractionation tank with double sludge cones used as a primary de-watering device according to an embodiment of the invention.
Figure 2C:
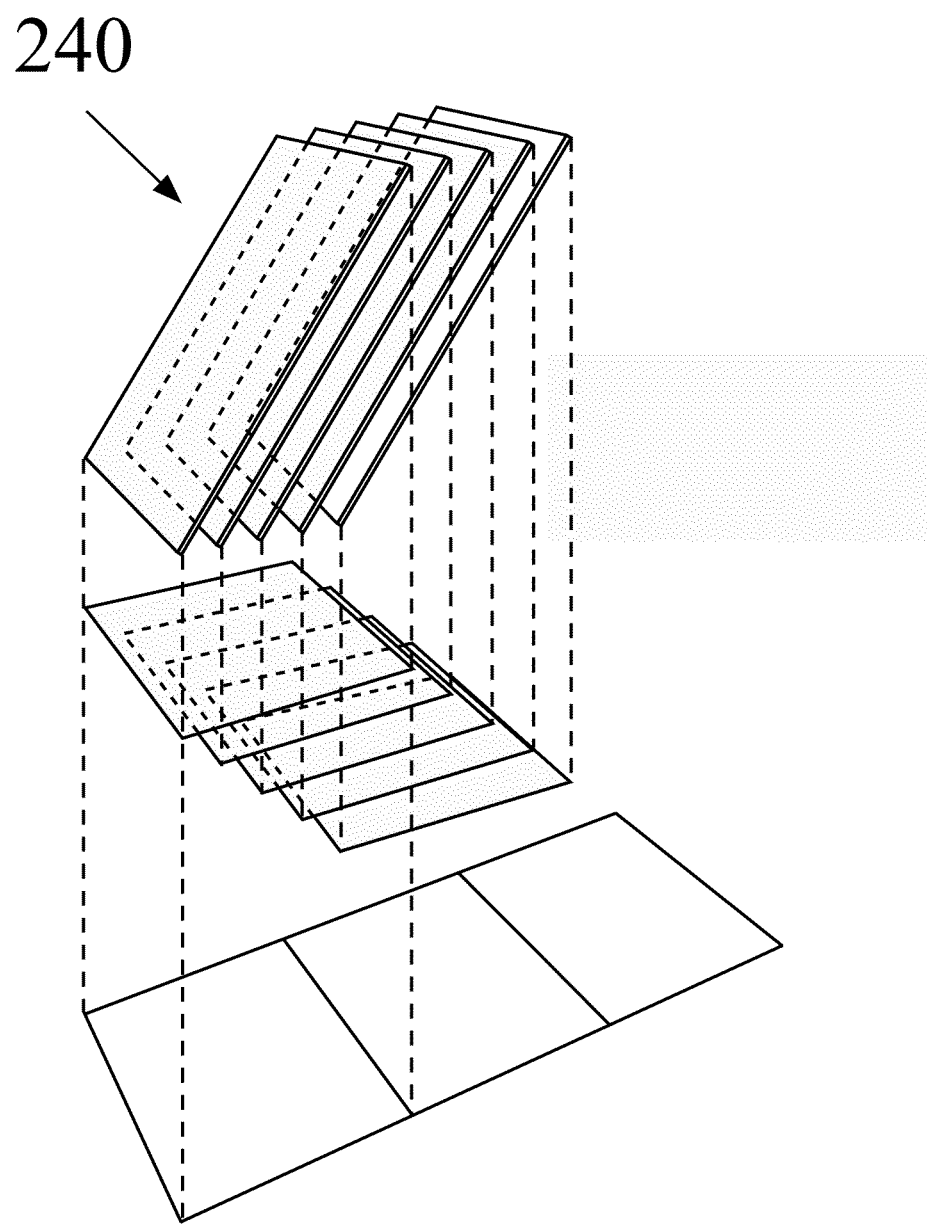
FIG. 2(C) is a line drawing of the sedimentation plates used in a fractionation tank according to an embodiment of the invention.

As shown in FIG. 2B, the GMH enters the fractionation tank 210 at inlet 220. The flow of the media inside the fractionation tank 210 is shown by arrows 230. The media passes downwards towards the bottom of the fractionation tank and is then directed at the sets of inclined plates 240. After passing around and/or over the sets of parallel plates 240 the medium exits the fractionation tank 210 at 250. The TPDWA exiting the fractionation tank at 250 near the top of the fractionation tank 210 can be returned to the pond 105. Since the process of pumping to the fractionation tank 210 can be a continuous process, the BPDWA can be continuously removed from the bottom cones 260 and 261. FIG. 2C shows a perspective view of the parallel plates 240.

In an embodiment of the invention, as shown in FIG. 2A a source of heat 290 can be used to heat the TPDWA 252 and/or the TSDWA 272 prior to return to the pond. In an embodiment of the invention, a source of cold 290 can be used to chill the TPDWA 252 and/or the TSDWA 270 prior and/or the piping used 272 to return to the pond. The heat source 290 can comprise heat generated by one or more of the following sources: a supply heat source, a recovered heat source, and a waste heat source from at least one of: a power plant, an industrial process, a cement plant, a kiln, an agricultural product processing plant, a processing plant, an incinerator, a furnace, an oven, an oil refinery, a petrochemical plant, a chemical plant, an ethanol plant, an amine treating plant, a natural gas processing plant, a steel plant, a metals plant, an ammonia plant, a coal gasification plant, a refinery, a liquid synthetic fuel plant, a gas synthetic fuel plant, an industrial plant, a manufacturing plant and a volume of carbon dioxide from a source of industrial carbon dioxide emission. The cold source 290 can comprise one or more of the following sources: a supply cold source, a recovered cold source, and a waste cold source from at least one of: an industrial process, a cement plant, an agricultural product processing plant, a processing plant, an oil refinery, a petrochemical plant, a chemical plant, an ethanol plant, an amine treating plant, a natural gas processing plant, a steel plant, a metals plant, an ammonia plant, a coal gasification plant, a refinery, a liquid synthetic fuel plant, a gas synthetic fuel plant, an industrial plant, a manufacturing plant and a volume of carbon dioxide from a source of industrial carbon dioxide emission. There are significant cost benefits to introducing the heat/cold through an exchanger 295 as the TPDWA 252 exits the fractionation tank 210. In an embodiment of the invention, the heat/cold exchanger 295 can be used to wrap around the tubing 252 returning the TPDWA to the pond (shell-tube). The liquid passing through the tubing/sleeve can act as a heat/cold exchanger (shell-tube) to heat/chill the tube carrying the GMH 222. In an alternative embodiment of the invention, a liquid-liquid heat/cold exchanger can be used to heat/chill the GMH 222. In various embodiments of the invention, a heat/cold exchanger other than a shell-tube or a liquid-liquid type can be used to heat/chill the GMH, the TPDWA or the TSDWA. In other embodiments, any type of heat/cold exchanger can be used. In an embodiment of the invention, the heat exchanger can be positioned to heat the GMH 222 before entering the fractionation tank 210. In an alternative embodiment of the invention, the heat exchanger can be positioned after the GMH 222 enters the fractionation tank. In an embodiment of the invention, the heat exchanger can be incorporated into the settling plates. In an embodiment of the invention, one side of the plates of the fractionation tank can act as heat exchangers to enhance the removal efficiency. In an embodiment of the invention, the lower side of the settling plates can be used to heat the GMH 222. In an alternative embodiment of the invention, a heat exchanger 295 can be used to heat the TPDWA 252 after it exits the fractionation tank 210 but before it enters the pond 205. In this way the heat energy transferred to the media will not interfere with the fractionation process. Further, the heat will be quickly introduced into the pond before it can dissipate in the fractionation tank. In an alternative embodiment of the invention, depending on weather conditions the heat exchanger can be used to heat the GMH 222 or the TPDWA 252.

The rate of flow of the GMH 222 into the fractionation tank 210 equals the rate of flow of the TPDWA 252 out through the outlets 250 plus the rate of flow of BPDWA 262 out through the outlets 260 and 261. The average residence time of the GMH within the fractionation tank 210 is primarily determined by the flow rate of GMH 222 into the inlet 220. The fractionation tank 210 with and without modifications has previously been used as a clarifier in the metal finishing industry to remove metal ions from water. When used as a clarifier to remove metal ions, the specification flow rate for the clarifier is 120 gallon per minute (GPM). Based on the volume of the fractionation tank, the average residence time can be approximately 50 minutes. At a flow rate of 60 GPM the average residence time of the algae in the fractionation tank 210 can be approximately 100 minutes. At a flow rate of 10 GPM the average residence time of the algae in the fractionation tank 210 can be approximately 10 hours.

In an embodiment of the invention, a flow rate of approximately 1-10 GPM results in significant depletion of the algae from the GMH 222. In an embodiment of the invention, the depletion of the algae from the TPDWA 252 being returned to the pond was detrimental to the growth of the algae in the pond. In an embodiment of the invention, a flow rate of approximately 1-10 GPM was unsuitable for sustaining log phase growth. In an embodiment of the invention, by depleting the abundance of the selected algae strain in the TPDWA 252, the selected strain of algae cannot compete against invasive algae species. Although in theory algae will propagate from a low critical concentration under ideal conditions, when competing against invasive species it can be critical to keep the selected algae strains in log phase growth.

In an embodiment of the invention, a channel system can include a fractionation stage to separate algae in the AGM. In an embodiment of the invention, an intrachannel fractionation stage can be used as a PDWD to separate algae from the GMH. In an embodiment of the invention, a fractionation stage which shares a partition wall with a channel system can be used as a PDWD to separate algae from the GMH. In an embodiment of the invention, an intrachannel fractionation stage can be used to separate the GMH into TPDWA and BPDWA. In an embodiment of the invention, an intrachannel fractionation stage can be used as a PDWD to separate algae from the GMH. The rate of flow of the GMH into the intrachannel fractionation stage equals the rate of flow of TPDWA out of the PDWD plus the BPDWA transported out of the PDWD. For low rates of flow of the BPDWA, the rate of flow of the GMH into the intrachannel fractionation stage equals the rate of flow of TPDWA of the PDWD. Further, the average residence time of the GMH within the fractionation stage is determined primarily by the flow rate of AGM into the PDWD inlet and the volume of the PDWD. In an embodiment of the invention, the sedimentation of the BPDWA from the GMH depends on the channeling of the GMH entering the intrachannel fractionation stage and the subsequent flow and turbulence characteristics of the GMH.

Figure 4A:
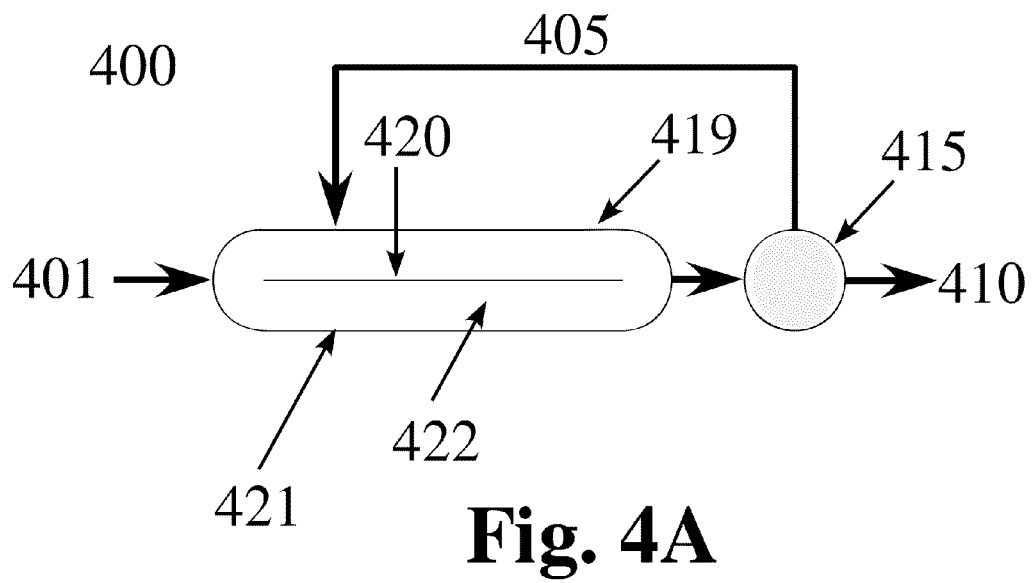
FIG. 4 shows overhead schematics of (A) a open channel pond with a separate fractionation tank and (B) an intrachannel fractionation stage according to different embodiments of the invention.
Figure 4B:
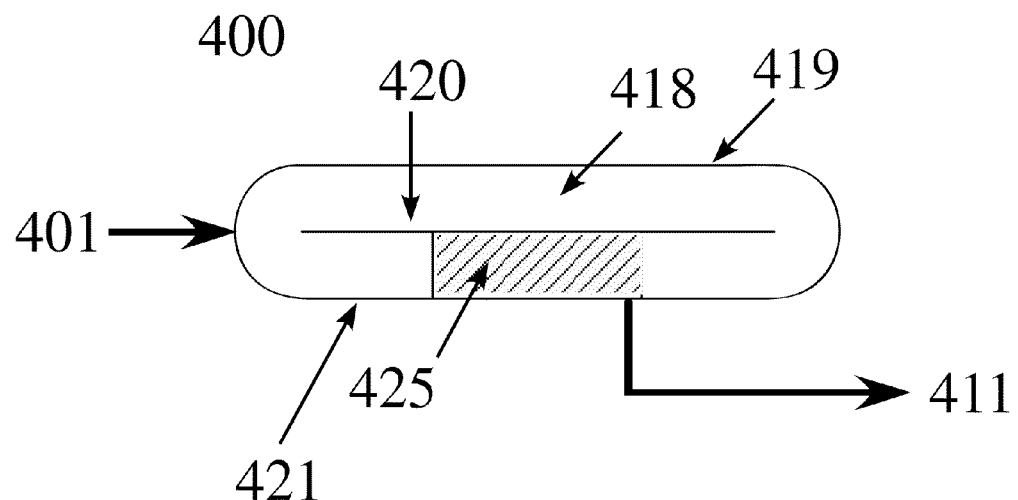

FIG. 4 shows overhead schematics of an open channel pond 400 with an intrachannel divider 420 where either (A) a separate fractionation tank 415 or (B) an intrachannel fractionation stage 425 (location shown in cross hatch shading) according to different embodiments of the invention. In both FIGS. 4A and 4B, AGM 401 can be added to the open channel pond 400 and the BPDWA 410, 411 can be transported from the PDWD (415, 425). However, in FIG. 4A the TPDWA is transported 405 back to the open channel pond 400, whereas in FIG. 4B the GMH flows into the PDWD and the TPDWA exiting the PDWD 425 flows directly back to the open channel pond 400. In various embodiments of the invention, the intrachannel divider 420 can be located offcenter with respect to the mid point between the sides (419, 421) of the open channel pond 400. An advantage of an intrachannel fractionation stage or an adjacent fractionation stage is that it is no longer necessary to pump AGM from the pond 205 or to return 252 to the pond as shown in FIG. 2A.

Figure 5:
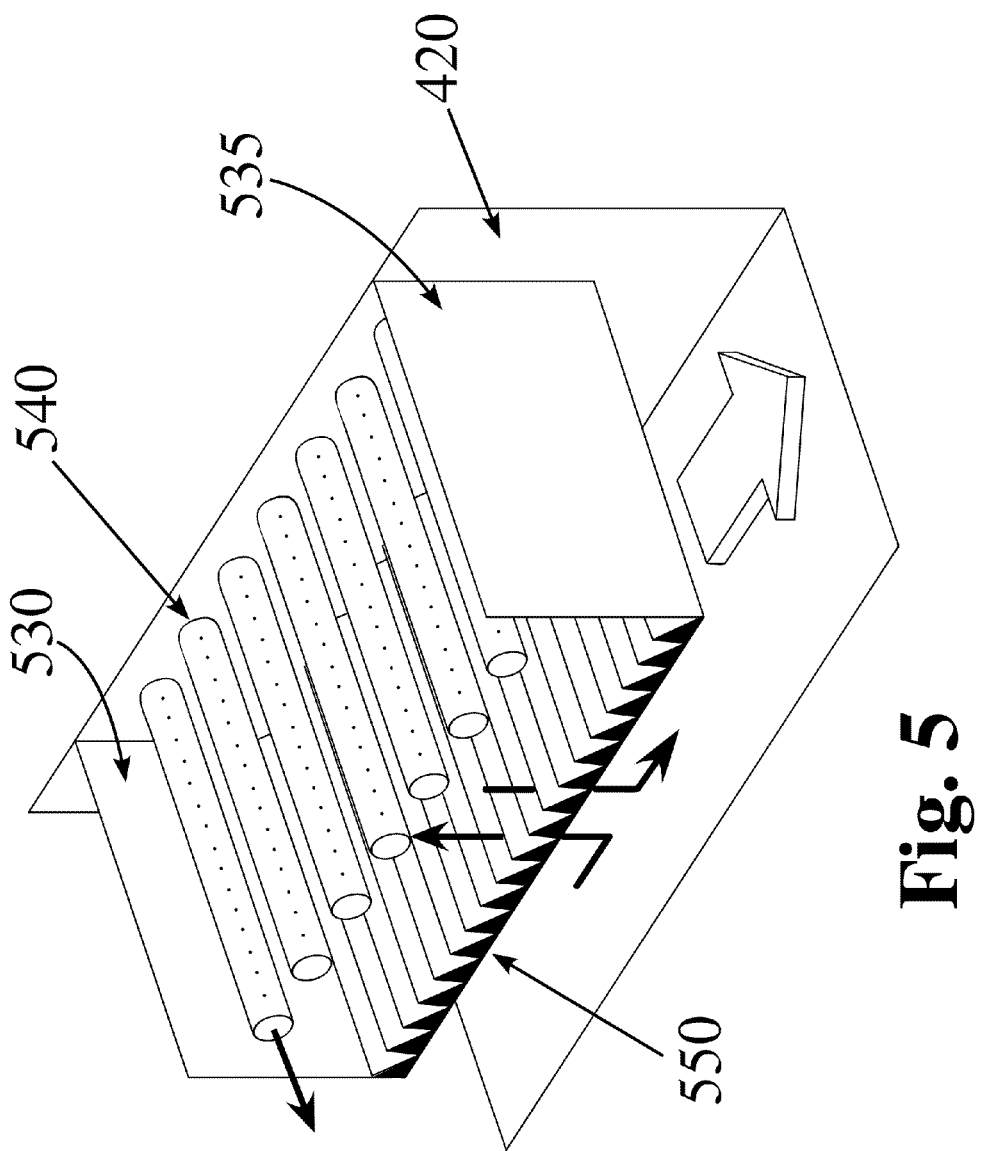
FIG. 5 is a schematic of an intrachannel fractionation stage which shows the fractionation stage uses tubes and plates to separate the algae according to various embodiments of the invention.

FIG. 5 is a schematic of an intrachannel fractionation stage which shows the pipes 540, baffles 550 and end plates 530, 535 used to separate the algae, according to various embodiments of the invention. The fractionation stage can span the entire width of the open ditch channel from the intrachannel divider 420 with the end plates 530, 535 forcing the circulating AGM flow beneath the end plates 530, 535 Baffles 550 form the bottom of the fractionation stage. Spaces between the baffles allow the GMH displaced by the AGM flow to enter the fractionation stage and the TPDWA to return to the open channel. Submerged orifice pipes 540 collect the algae and move it from the ditch system.

Figure 6:
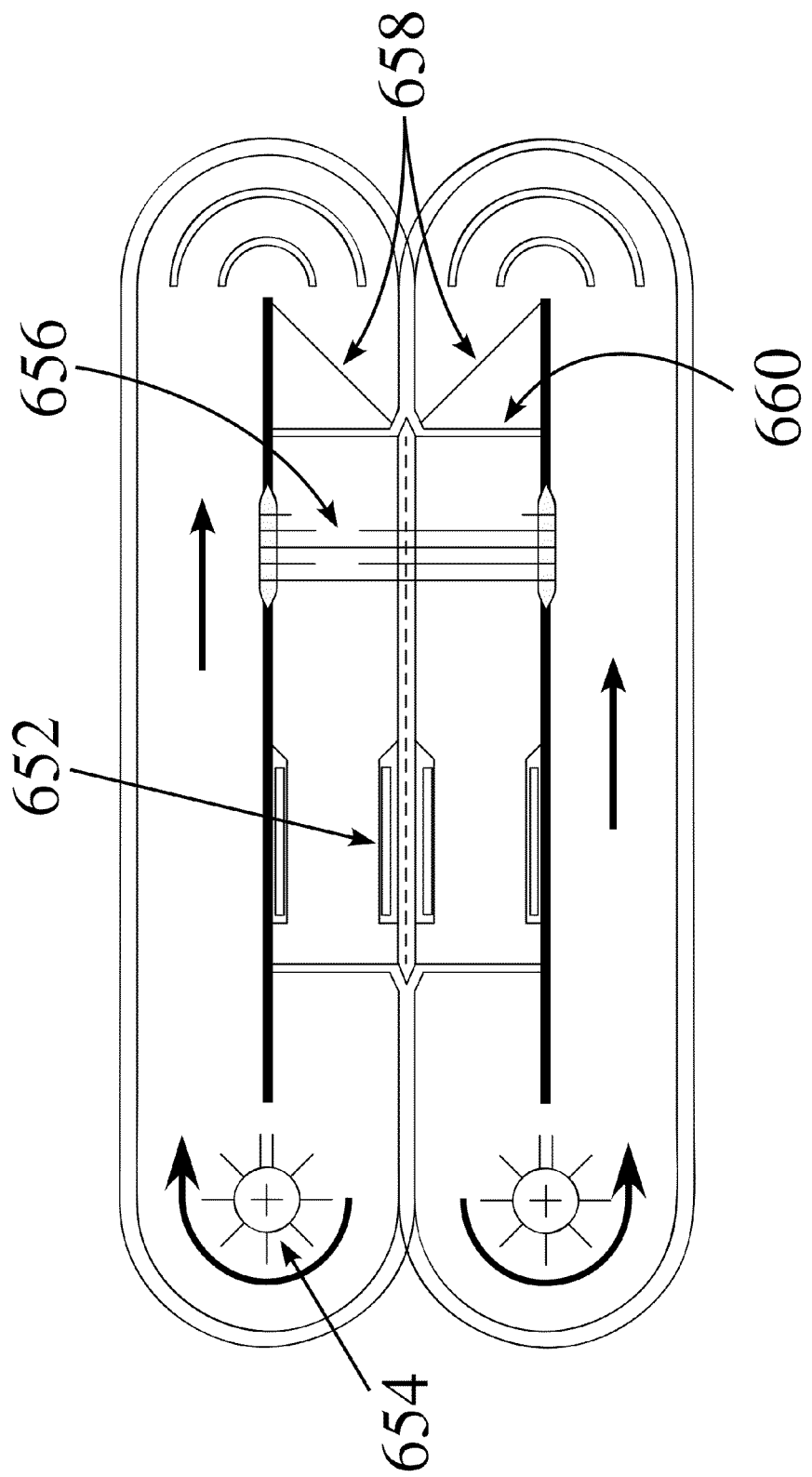
FIG. 6 shows an overhead schematic of a carrousel intrachannel clarifier which can be used in conjunction with an open channel system to separate the algae according to an embodiment of the invention.
Figure 7:
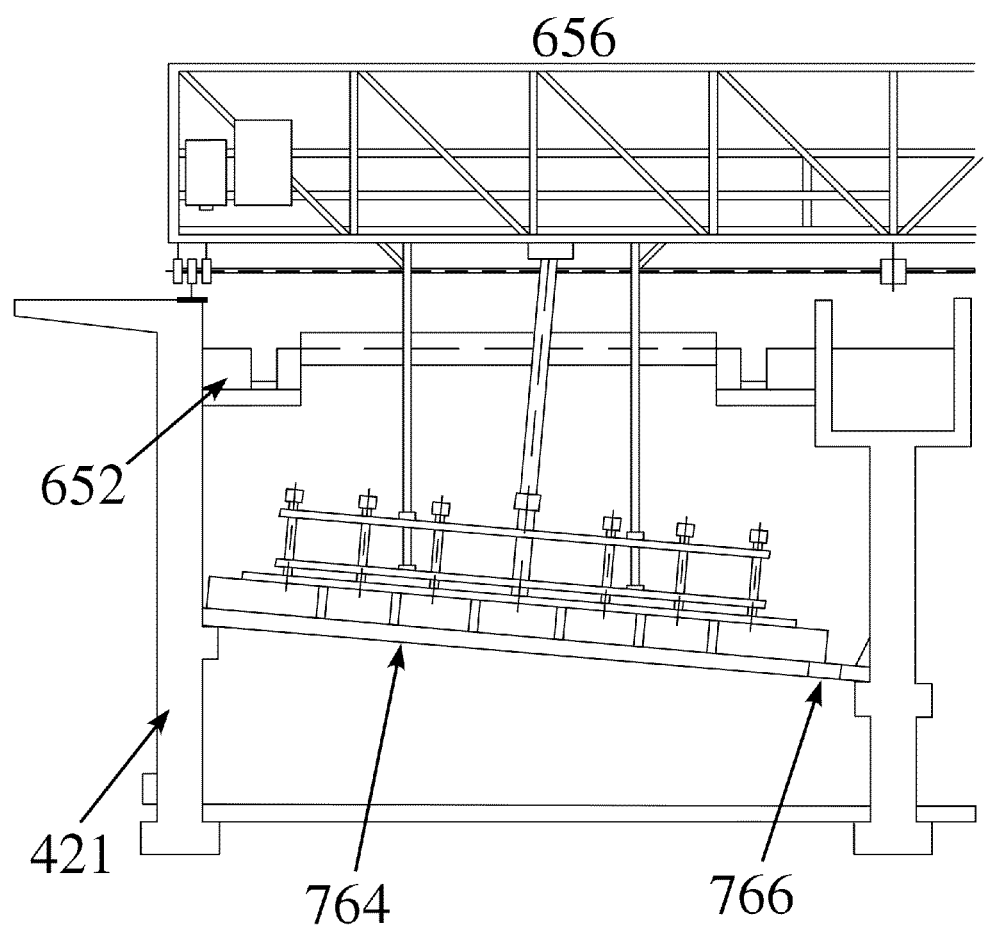
FIG. 7 shows a cross section of a carrousel intrachannel clarifier of FIG. 6 according to an embodiment of the invention.

FIG. 6 shows an overhead schematic of a dual carrousel intrachannel fractionation stage which can be used in conjunction with two adjacent open channel systems according to an embodiment of the invention. Inlet baffles 658 and inlet control gates 660 control the flow of the AGM as it enters the PDWD. A bridge 656 allows access to the PDWD. Floating material and/or TPDWA can be removed with launderers 652. A paddle wheel 654 regulates the AGM flow and thereby the GMH flow. As shown in FIG. 7 the carrousel intrachannel uses a sloped solid floor 764 as a bottom with the circulating AGM flow forced beneath the solid floor 764. In each open channel system, the fractionation stage spans the entire width of one side of the open channel 421. GMH displaced by the AGM flow enters the front of the fractionation stage through inlet control gates 660. Inlet baffles 658 reduce the effects of turbulence at the inlet on fractionation performance. Launders 652 located at the back of the fractionation stage allow floating material including TPDWA to return to the channel system. BPDWA exits through ports 766 located at the side of the sloped bottom.

Figure 8A:
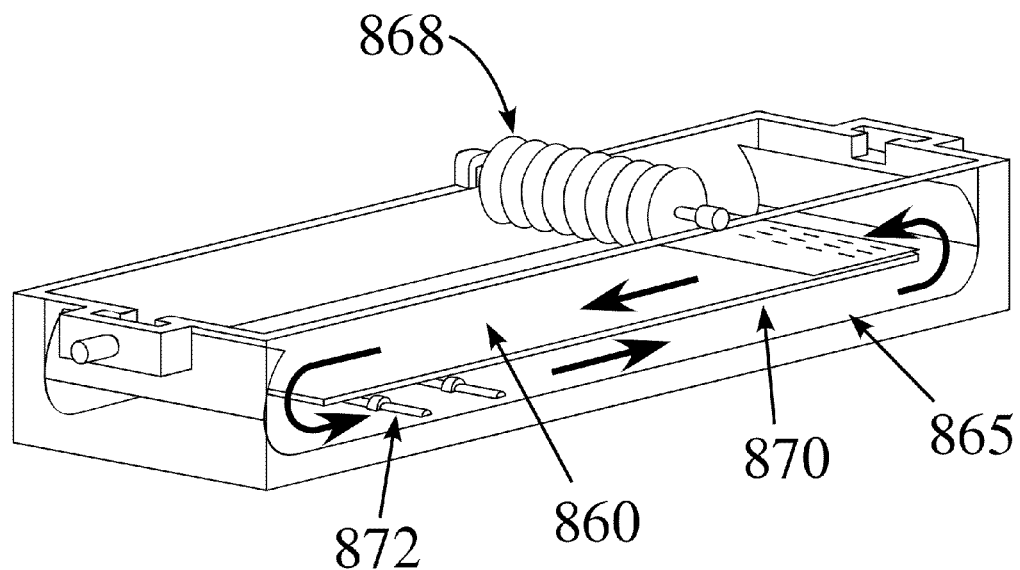
FIG. 8 shows (A) a perspective view and (B) a cross section of a side-channel fractionation stage used in an open channel system to separate the algae according to an embodiment of the invention.
Figure 8B:
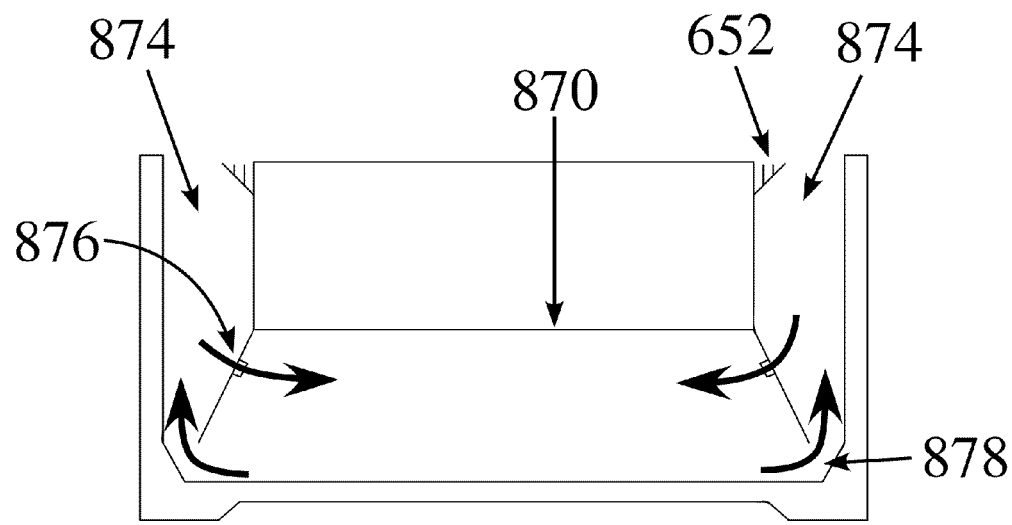

FIG. 8 shows (A) a perspective view and (B) a cross section of a side-channel fractionation stage used in an open channel system according to an embodiment of the invention. In FIG. 8A the AGM is circulated with an auger 868 above a horizontal baffle divider 870. As shown in FIG. 8B, the open channel system consists of a rectangular basin with a horizontal divider baffle 870 that creates an upper 860 and lower 865 compartments in the channel system. AGM in the open channel system continuously circulates, but between the upper 860 and lower 865 compartments. Diffusers 872 in the bottom compartment and the auger 868 circulate the AGM. Side-channel fractionation stage(s) 874 are built into the sides of the open channel system. GMH displaced by the AGM flow enters the slots at the bottom of the fractionation stage 876. Recirculation ports 878 provide for TPDWA to return to the open channel system. BPDWA is trapped and transported from the lower compartment.

Figure 9:
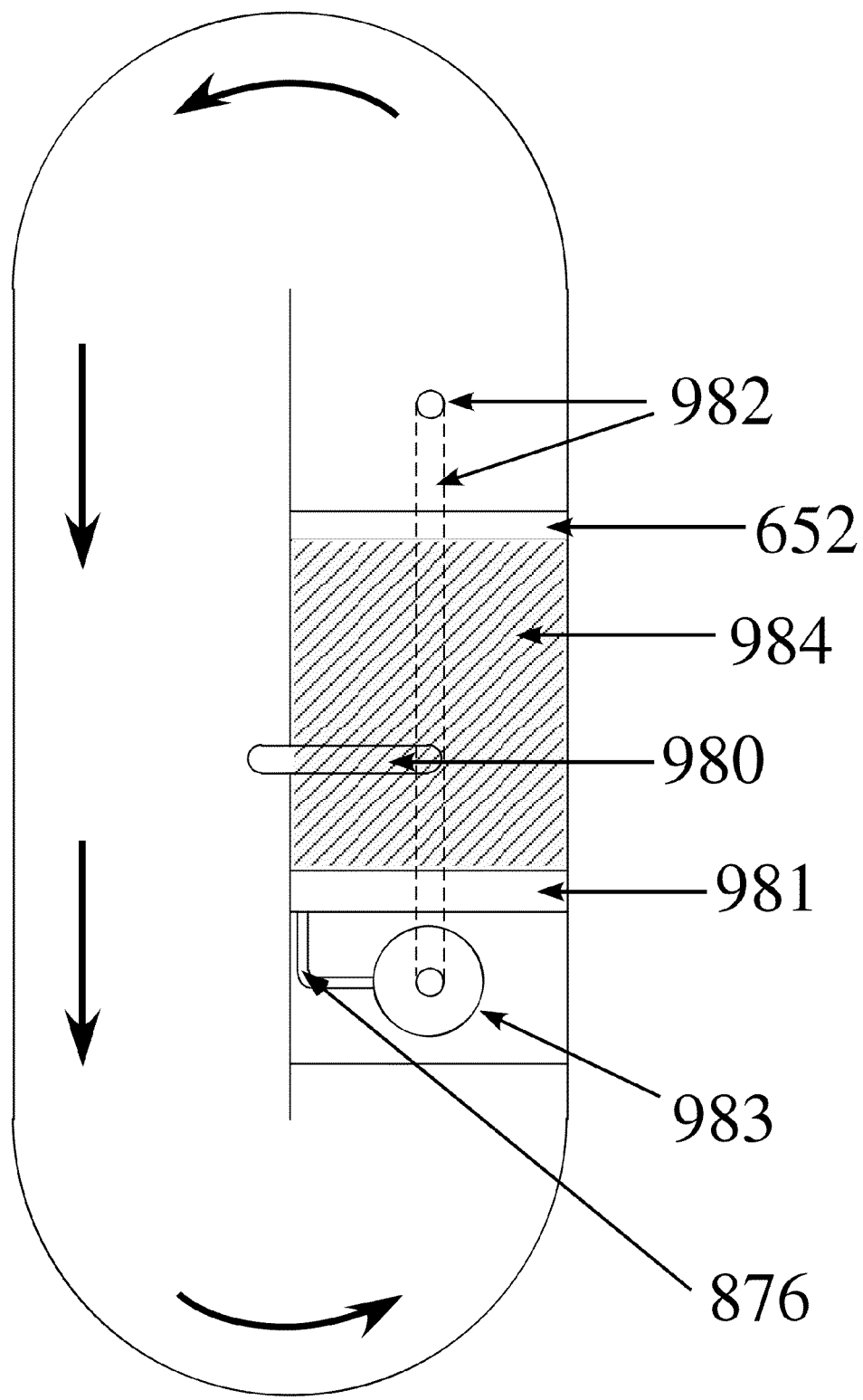
FIG. 9 shows an overhead schematic of an integral fractionation stage used in an intrachannel system to separate the algae according to an embodiment of the invention.
Figure 10:
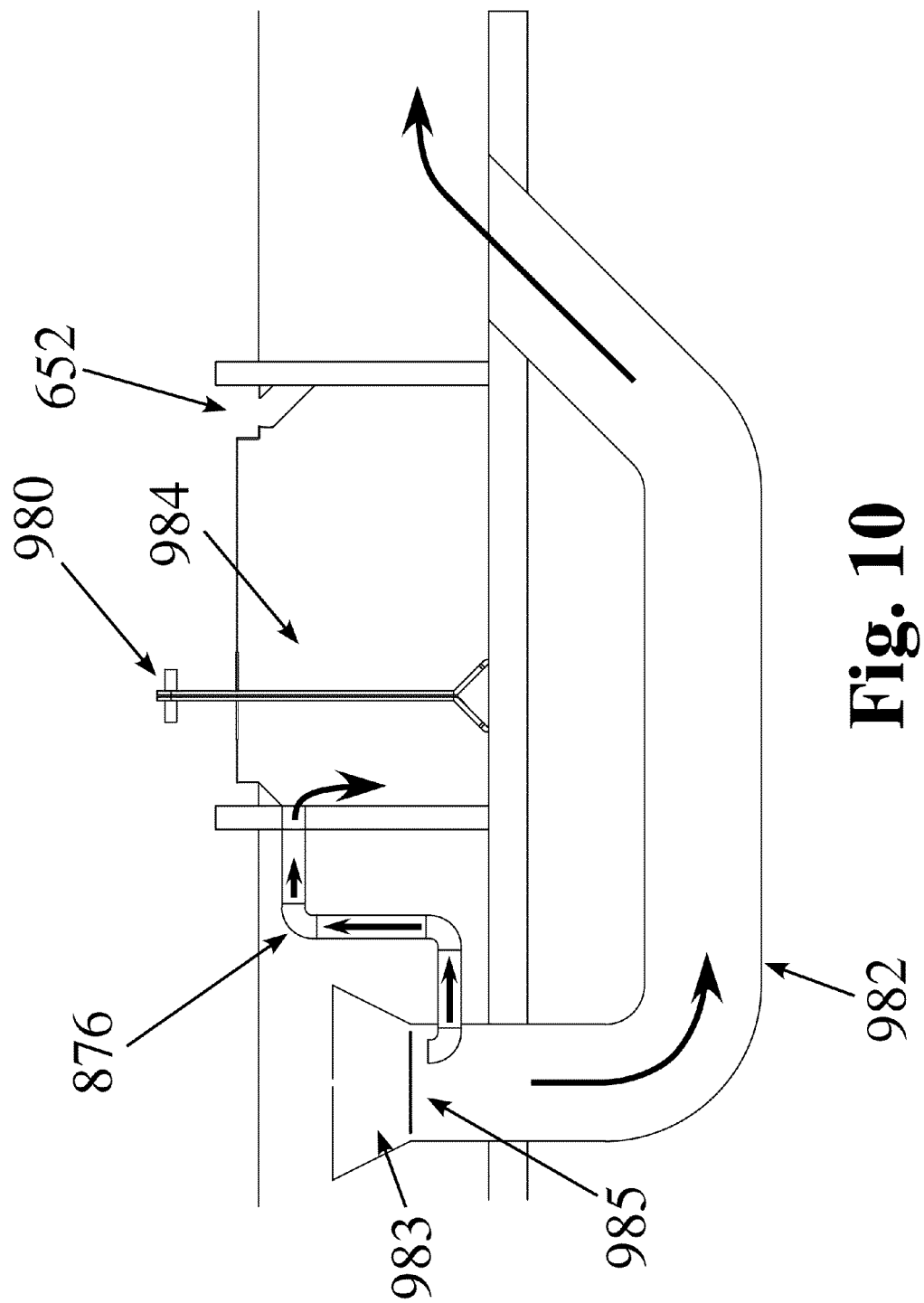
FIG. 10 shows an side view of the integral fractionation stage shown in FIG. 9 according to an embodiment of the invention.

FIG. 9 shows an overhead schematic of an integral fractionation stage used in an intrachannel system according to an embodiment of the invention. The circulating AGM enters a funnel 983 where the GMH is separated and BPDWA flows through a side-tube 876 to a lock 984 (shown in cross hatch shading) defined by barriers 981 and 952. The funnel 983 connects to a tube 982, where the side-tube 876 forms a 'T'. After separation, the tube 982 is used to return the TPDWA past the barrier 952. A siphon 980 is located in the lock 984. As shown in FIG. 10 the fractionation stage including the funnel 983 and barrier 985 in the draft tube 982 are used to transfer TPDWA running underneath the lock 984 back into the channel pond. The draft tube 982 creates a head differential between the fractionation stage and the channel. This head differential permits separated BPDWA to be transferred to the lock 984. Launder(s) 652 within the lock 984 collect and remove floating material and TPDWA from the lock 984 to the channel system. The siphon 980 is used to collect and transport BPDWA from the channel system.

Figure 11:
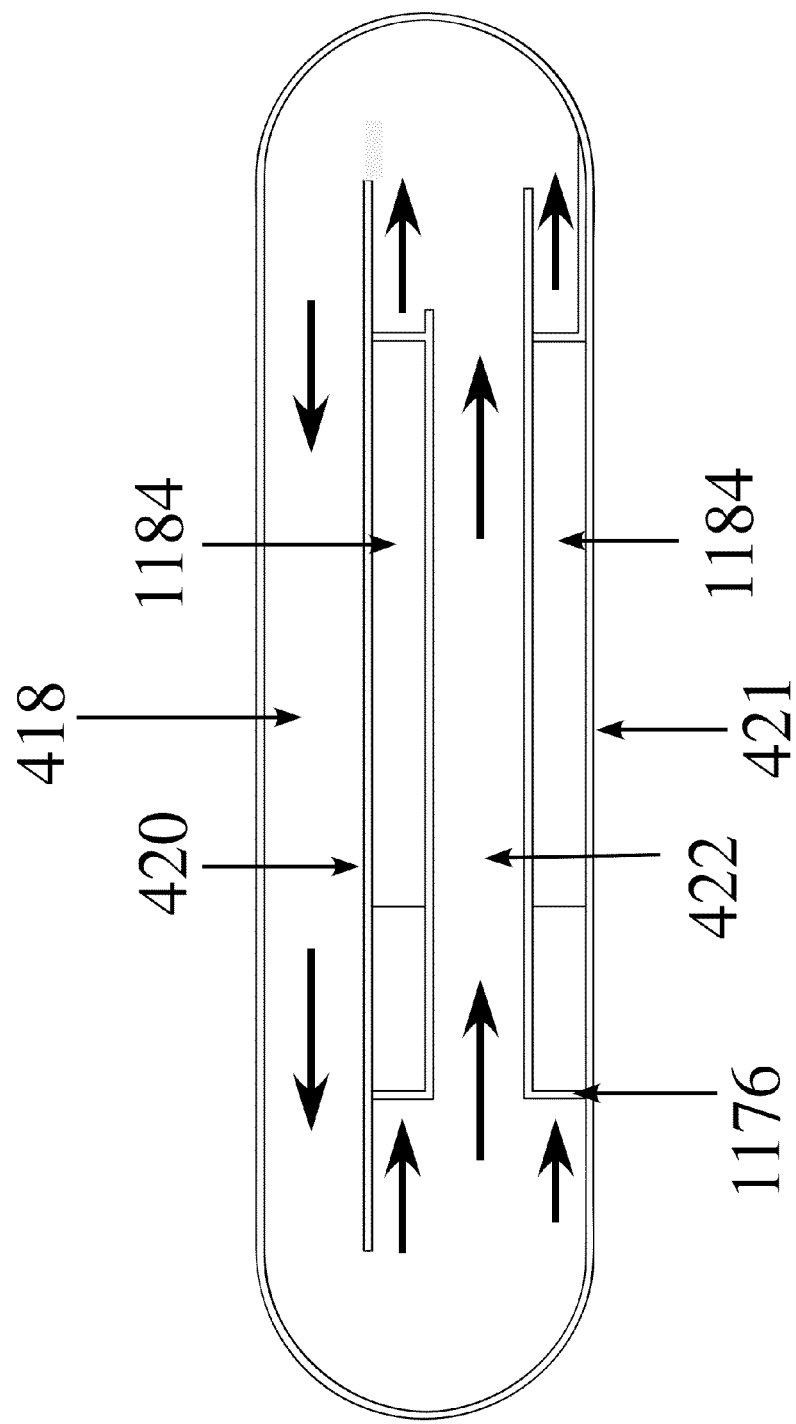
FIG. 11 shows an overhead perspective of a sidewall separator used in an open channel system to separate the algae according to an embodiment of the invention.
Figure 12:
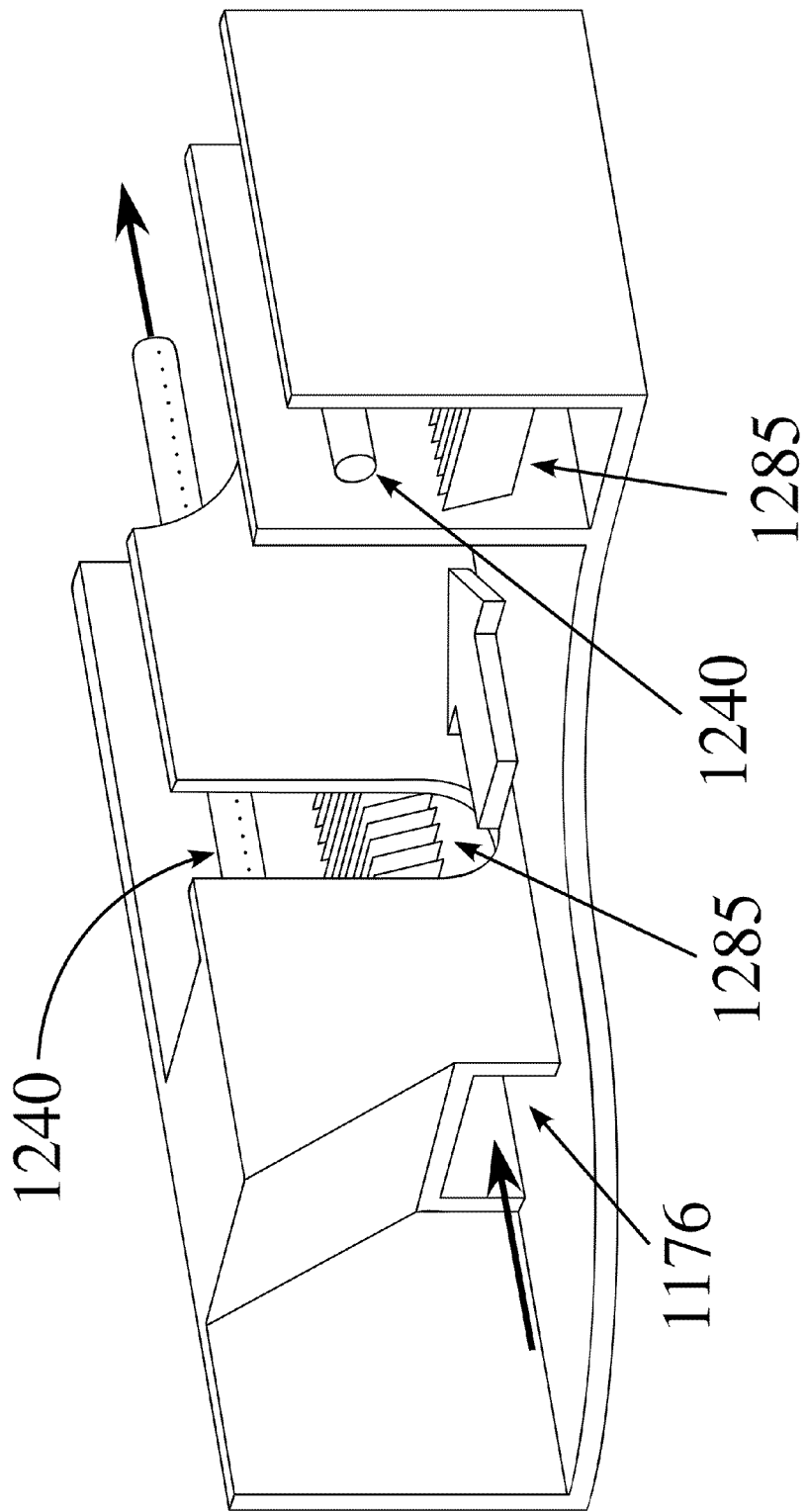
FIG. 12 shows a cut through perspective of a sidewall separator shown in FIG. 11 according to an embodiment of the invention.

FIG. 11 shows an overhead perspective of an algae separation process that uses one or more sidewall separator(s) 1184 in an open channel system. The divider wall 420 in the open channel system is located off center such that the flow through 422 plus the combined flow through the sidewall separators 1184 is equivalent to the flow in 418. Each sidewall separator 1184 projects out from the wall (420, 421) of the open channel system and extends its full depth. Most of the circulating AGM flow is through 422 between the sidewall separators 1184 while a portion of it enters the inlet 1176. The AGM returns via 418. Inside the sidewall separator 1184 GMH, enters 1176 and is pushed or displaced by incoming AGM, and moves through inclined baffles 1285 as shown in FIG. 12. Submerged orifice pipes 1240 collect and return the TPDWA to the open channel system. BPDWA moves down through the baffles 1285 and exits the sidewall separators and the open channel system.

Figure 13:
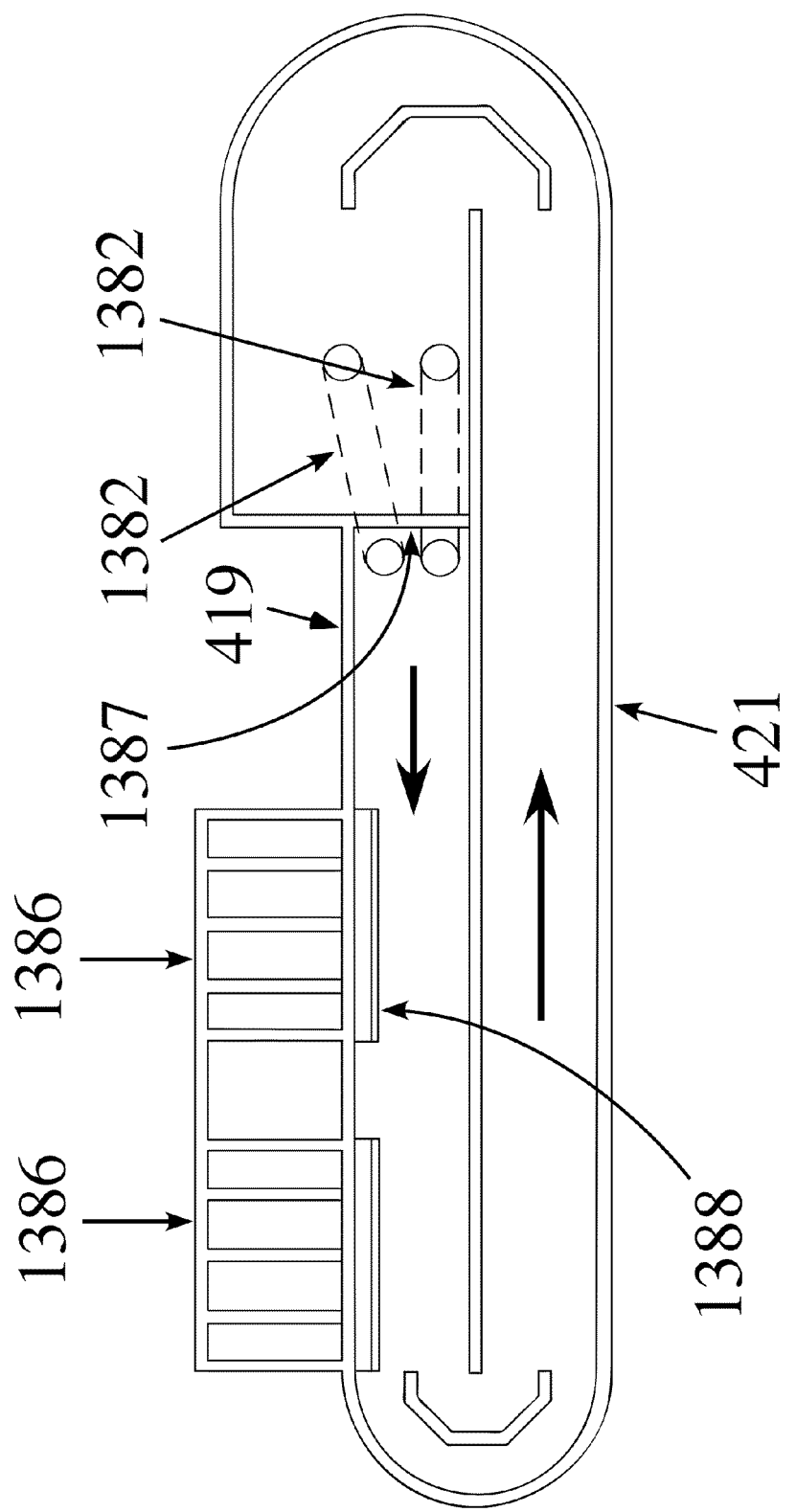
FIG. 13 shows an overhead of an integral fractionation stage used in an open channel system to separate the algae according to an embodiment of the invention.
Figure 14:
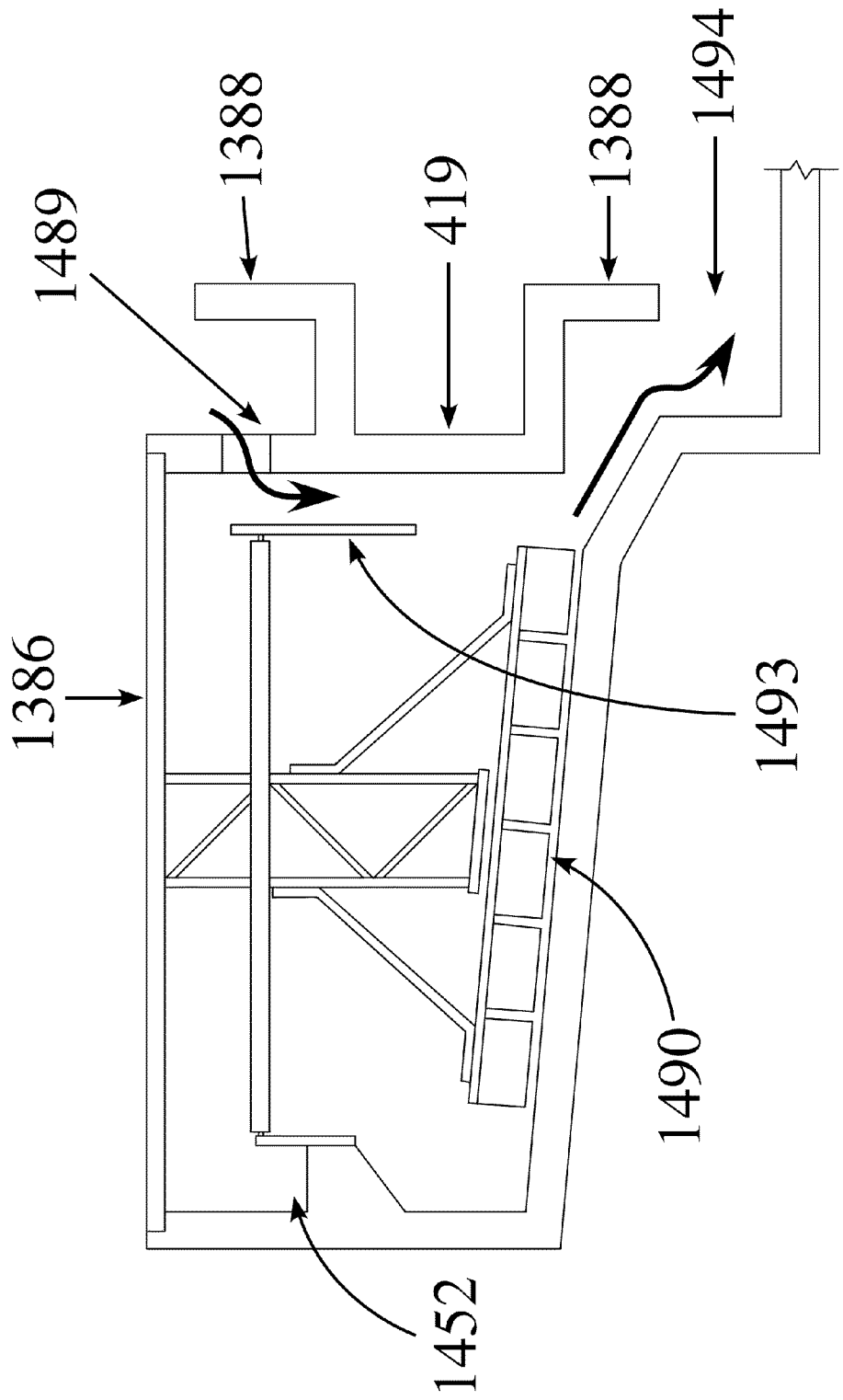
FIG. 14 shows a cross section of the integral fractionation stage shown in FIG. 13 according to an embodiment of the invention.

FIG. 13 shows an overhead view of one or more off-axis fractionation stage(s) 1386 used in conjunction with an open channel system according to an embodiment of the invention. One or more pipes 1382 used to regulate the AGM flow. One or more channel barriers 1387, 1388 are used to direct the AGM flow into the fractionation stage(s) 1386. The fractionation stage(s) can be located adjacent to the open channel system and share a divided wall with the outer wall of the open channel (419, 421). As shown in FIG. 14 GMH displaced by the AGM flow enters the fractionation stage through inlet slots 1489 in the common wall 419 between the open channel system and the fractionation stage 1386. Once in the fractionation stage, the flow encounters a baffle 1493 the height of which can be varied to direct more or less flow through the fractionation stage 1386. One or more launders 1452 at the far side of the fractionation stage 1386 can be used to return TPDWA to the channel system. TPDWA returns to the open channel system through exit 1494. BPDWA is removed through bottom slots 1490.

Figure 15:
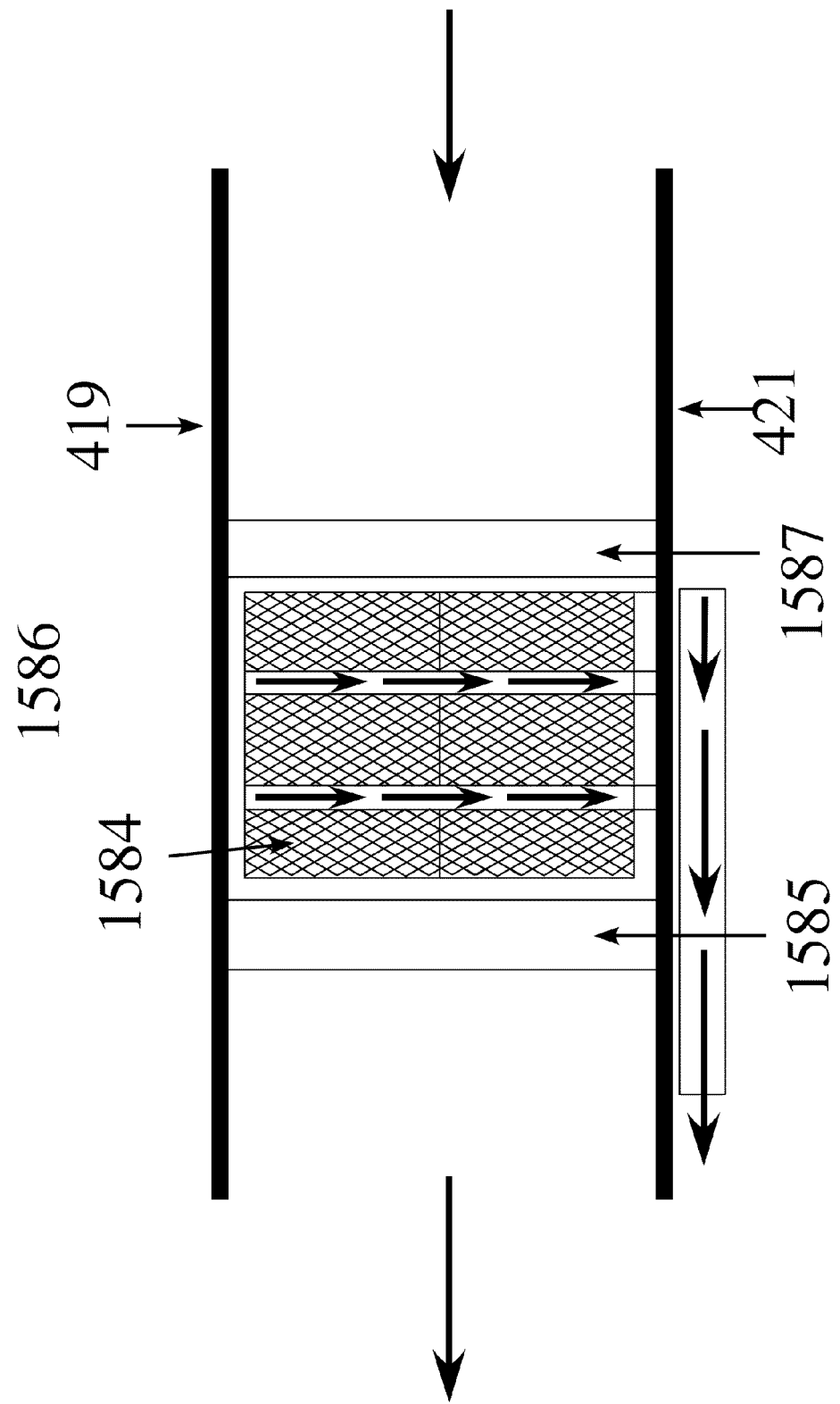
FIG. 15 shows an overhead of an integral fractionation stage (only) used in an open channel system to separate the algae according to an embodiment of the invention.
Figure 16:
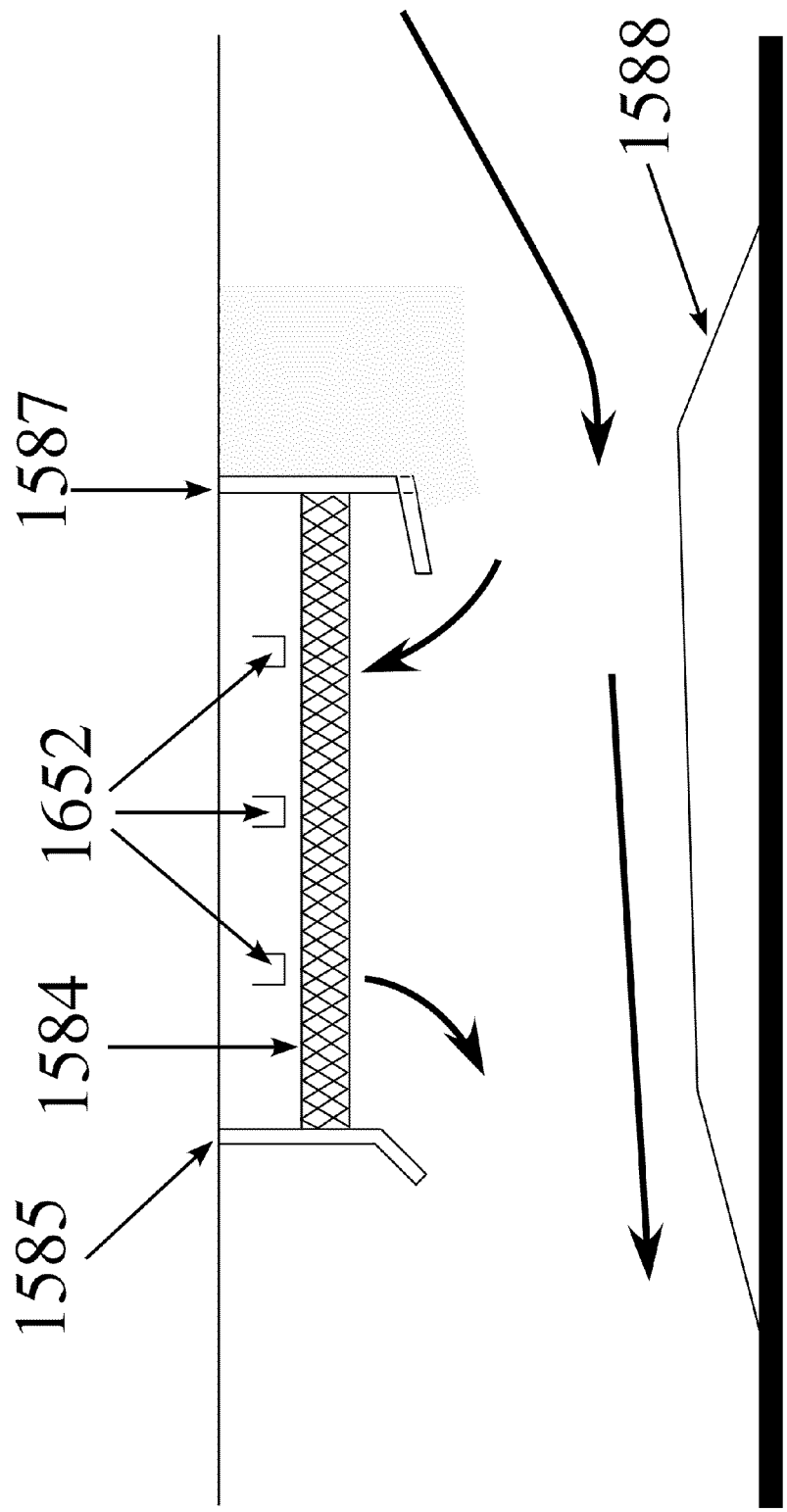
FIG. 16 shows a cross section of the integral fractionation stage shown in FIG. 15 according to an embodiment of the invention.

FIG. 15 an overhead view of an integral fractionation stage 1586 (only) used in an an open channel system according to an embodiment of the invention. The fractionation stage 1586 can span the entire side of the open channel system with standard tube settler modules 1584 located across the entire width from 420 to 421. A barrier 1587 can be used to direct the flow of the AGM into the PDWD which is further defined by the exit wall 1585. As shown in FIG. 16 GMH displaced by the AGM flow proceeds upward through the tube settler modules 1584. TPDWA can be returned to the open channel system through launderers 1652 at the surface while BPDWA flows downward through the tube settler modules and can be removed. Channel flow beneath the fractionation stage 1586 can be increased by a variable height raised section 1588 on the floor of the channel.

Figure 17A:
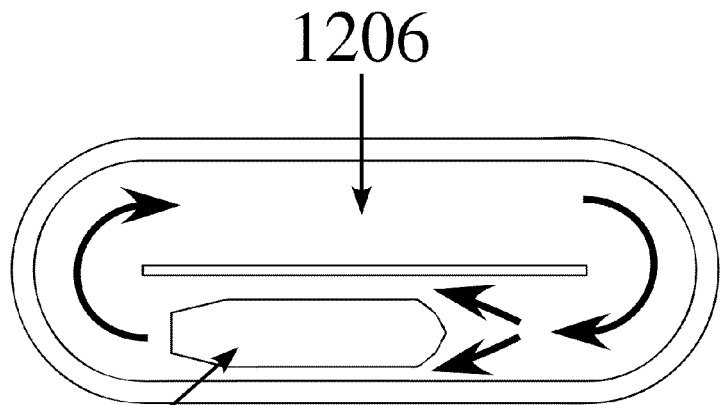
FIG. 17 shows schematically (A) an overhead view of the boat fractionation stage used in an open channel system to separate the algae (B) an overhead view of the boat fractionation stage (only) and (C) a cross section of the boat fractionation stage according to an embodiment of the invention.
Figure 17B:
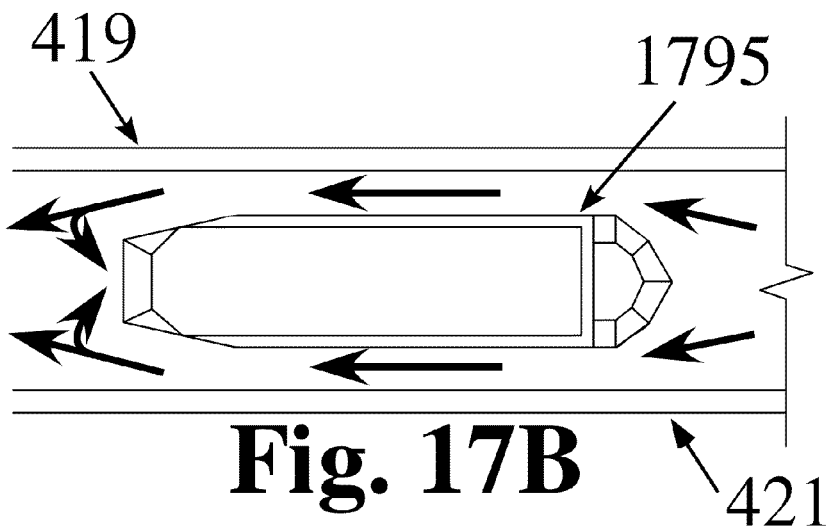
Figure 17C:
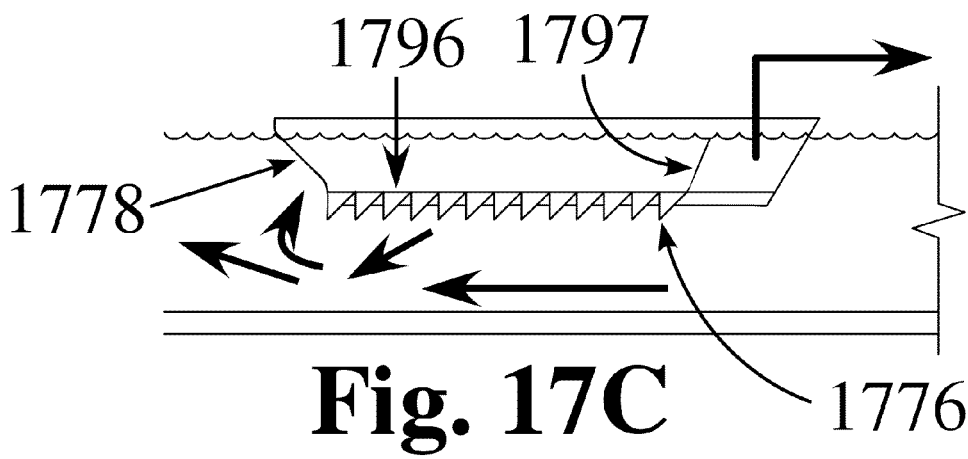

FIG. 17 shows schematically (A) an overhead view of the boat fractionation stage 1795 used in an open channel system (B) an overhead view of the boat fractionation stage 1795 (only) almost spanning the entire width of the open channel 421 and (C) a cross section of the boat fractionation stage according to an embodiment of the invention. As shown in FIG. 17C, the boat fractionation stage is placed in one side of the open channel system where the circulating AGM flows around and underneath it. GMH, displaced by the inflowing AGM, enters at the downstream end or back of the fractionation stage 1778. GMH enters the front of the fractionation stage over a weir 1797 before TPDWA returns to the open channel system. BPDWA exits through return ports that cover the entire bottom of the fractionation stage 1796. Each port can have its own separate hopper. By design, the boat fractionation stage restricts the flow in the open channel system creating a head differential between the fractionation stage and open channel system that assists algae removal through the ports.

Figure 18:
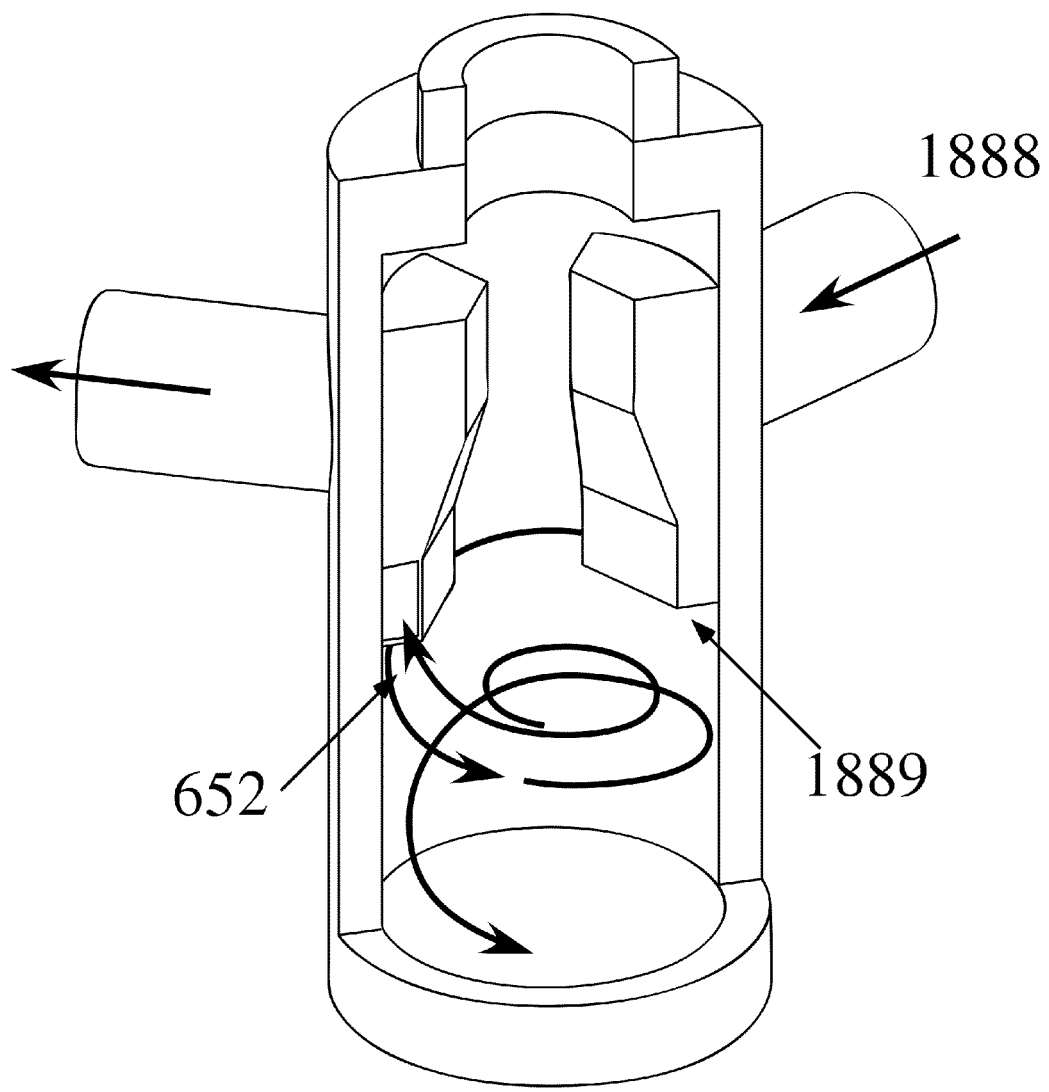
FIG. 18 shows a vortex fractionation stage used in an open channel system to separate the algae according to an embodiment of the invention.

FIG. 18 shows a vortex fractionation stage used in an open channel system according to an embodiment of the invention. The GMH enters (1888, 1889) the vortex fraction system and a circular motion is imparted on the GMH. This circular motion effects a centrifugal force on the denser algae particles and combines with the gravitation force to impart a downward spiral motion. This enhances the fractionation separation of the GMH and traps the BPDWA which is collected at the bottom of the vortex fractionator. The TPDWA flows upwards and out 652 of the vortex separator returning to the pond.

The BPDWA collected is dictated largely by the GMH concentration. In an embodiment of the invention, with lower BPDWA concentrations the BPDWA can be pumped to the secondary dewatering process. With higher BPDWA concentrations the BPDWA can be too dense to efficiently pump to the secondary dewatering process. In an embodiment of the invention, with higher BPDWA concentrations an auger and/or a conveyor can be used to transport the BPDWA to the secondary dewatering process.

In various embodiments of the invention incorporating an intrachannel or adjacent PDWD, a means to control the flow of AGM into the primary dewatering devise can include, a wire, a gate, a cover, a plate, a valve, and a mechanical flow control restrictor.

Intrachannel fractionation stages can restrict the circulating flow of the GMH in the channel. The paddles or other flow equipment engineered to induce the flow in the GMH must overcome these restrictions to maintain adequate velocities throughout the channel. Designers of systems using any of the intrachannel fractionation stages can insure that the flow adequately mixes the algae feed stock, the AGM, and added constituents in the open channel. The flow equipment can be engineered to overcome the increased headloss in the channel because of the intra channel fractionation stage.

Figure 3A:
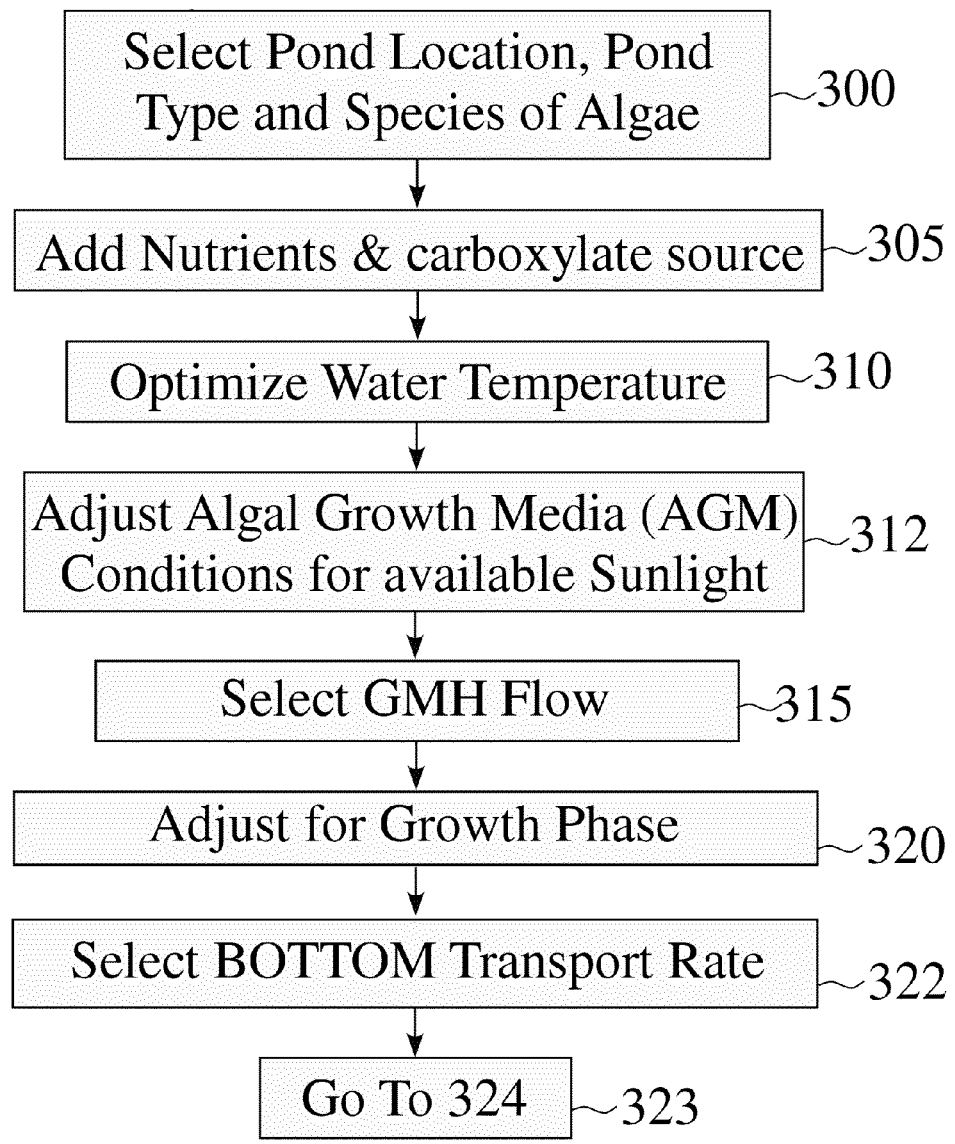
FIG. 3(A) is a flowchart showing the procedure used to optimize growth of one or more selected species of algae in a pond with an in-line primary de-watering device (PDWD) according to an embodiment of the invention.

As shown in FIG. 3A, for an intrachannel fractionation stage located in an open channel pond a number of parameters can be optimized based on the characteristics of the system including the location, the pond type, the pond size selected and the specie or species of algae selected 300. Nutrients and one or more carboxylate sources such as dissolved $CO_2$ can then be added 305. Based on the species selected, the water temperature can be optimized 310. The AGM conditions can be adjusted for the available sunlight and algae concentration 312. Next the GMH flow can be selected 315. The GMH flow can be optimized to keep the algae growing in the appropriate phase 320. The BOTTOM pump rate can be adjusted to maximize harvesting 322. The process outlined in FIG. 3A can be optimized according to one or more of the schemes set out in FIGS. 3B-3K, as shown at 323.

Figure 3B:
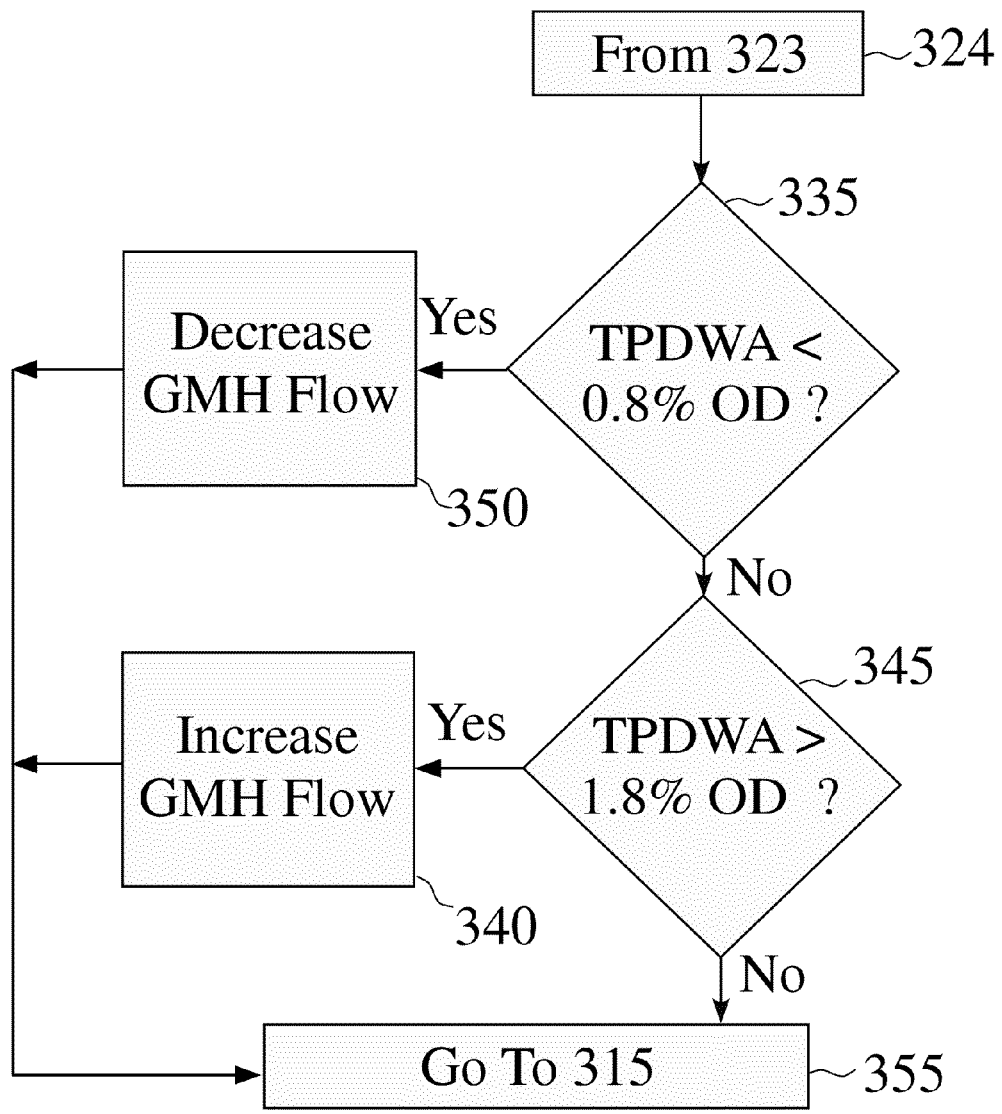
FIG. 3(B) is a flowchart showing a procedure used to optimize primary de-watering of GMH with an in-line PDWD according to an embodiment of the invention.

In an embodiment of the invention, the TPDWA exiting the intrachannel PDWD is tested before being continuously recycled back to the pond. Based on the concentration of the TPDWA different actions can be taken. In an embodiment of the invention, from step 323 a test can be carried out as shown in FIG. 3B, 324. The GMH flow can be decreased 350 (see also FIG. 3G) if the TPDWA concentration falls below 0.8 OD 335. Alternatively, the GMH flow can be increased 340 (see also FIG. 3F), if the TPDWA concentration increases above 1.8 OD 345. After adjusting the GMH flow 340, 350, step 315 is continued at 355. Thus, at step 355 the change in GMH flow can be related back to the procedure shown in FIG. 3A at step 315, and in particular the requirement to keep the algae growing in a particular stage of growth.

Figure 3C:
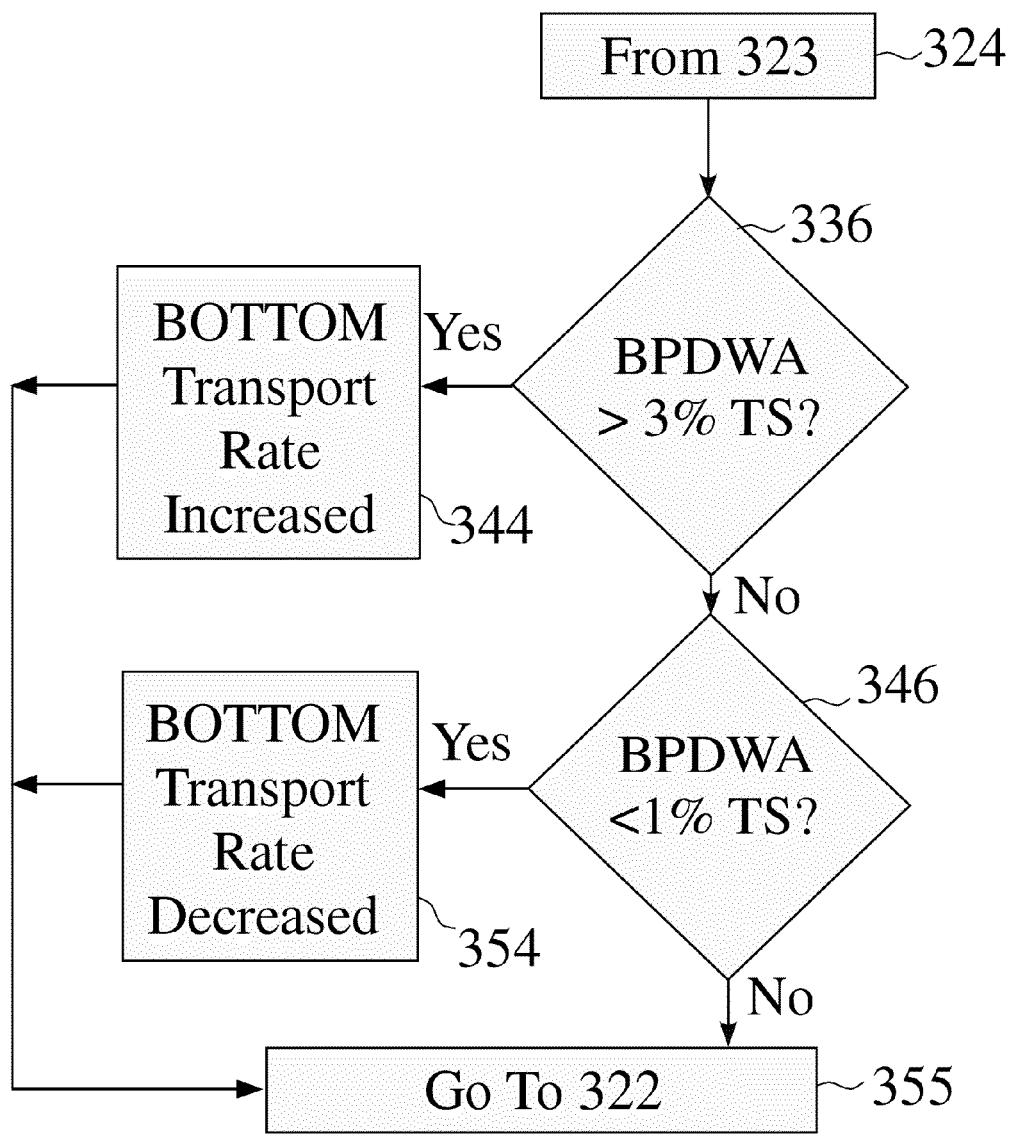
FIG. 3(C) is a flowchart showing a procedure used to optimize primary de-watering of GMH based on the bottom primary de-watered algae (BPDWA) with an in-line PDWD according to an embodiment of the invention.

In an embodiment of the invention, the GMH flow rate is adjusted to keep the concentration of TS in a defined range for a secondary dewatering step. FIG. 3(C) is a flowchart showing the procedure used to optimize primary de-watering of GMH and growth of the TPDWA based on the BPDWA concentration according to an embodiment of the invention. In FIG. 3(C) the GMH directly enters the fractionation stage. The BPDWA is removed from the fractionation tank using pumping, gravity feed, an auger or a conveyor. In these embodiment of the invention, from step 323 a test can be carried out 324. The BOTTOM transport rate can be increased 344 if the BPDWA concentration is above 3% TS 336. Alternatively, the BOTTOM transport rate can be decreased 354 if the BPDWA concentration falls below 1% TS 346. After adjusting the BOTTOM transport rate 344, 354, step 322 is continued at 355. At step 355 the change in BOTTOM transport rate can be related back to the procedure shown in FIG. 3A at step 322, and in particular the requirement to keep the algae growing in a particular growth phase.

In an alternative embodiment of the invention, if the BPDWA is greater than 5% TS, then the AGM and/or GMH flow can be increased. If the BPDWA is less than 0.7% TS, then the AGM and/or GMH flow can be decreased. In another alternative embodiment of the invention, if the BPDWA is greater than 10% TS, then the AGM and/or GMH flow can be increased. If the BPDWA is less than 0.2% TS OD, then the AGM and/or GMH flow can be decreased.

Figure 3D:
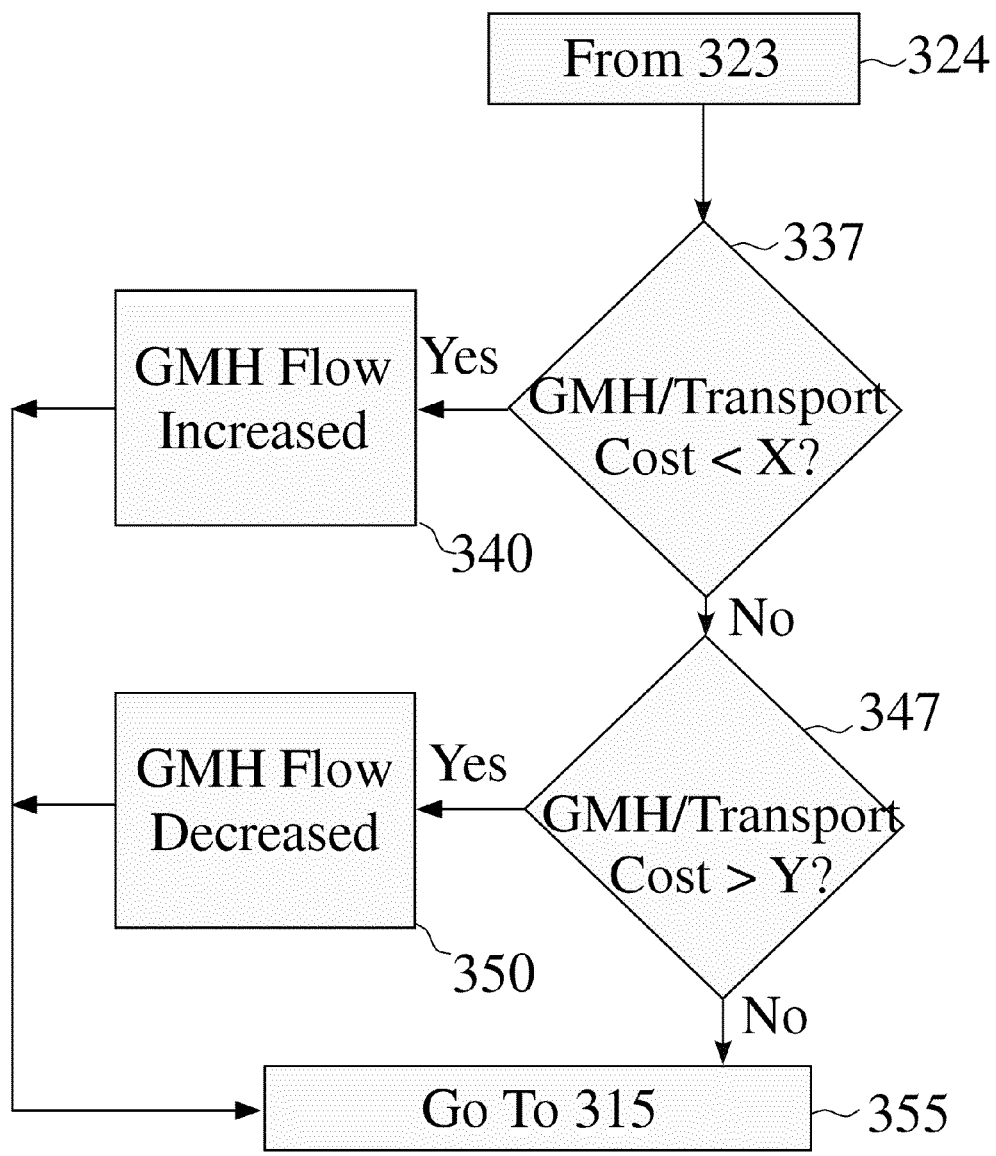
FIG. 3(D) is a flowchart showing a procedure used to optimize primary de-watering of GMH based on the ratio of the GMH to the pumping cost with an in-line PDWD according to an embodiment of the invention.

In an embodiment of the invention primary de-watering of GMH and growth of the algae can be optimized based on the BPDWA and the cost of transporting the BPDWA from the pond to the SDWD and the cost of transporting the TSDWA back into the pond. In FIG. 3(D) the GMH is continuously transported from the pond thru the PDWD and the TPDWA is continuously returned to the pond. The BPDWA is removed from the PDWD using pumping, gravity feed, an auger or a conveyor. Based on the ratio of the GMH concentration and the cost of transporting the BPDWA and/or the cost of transporting the TSDWA different actions can be taken. For example, if the GMH concentration/Transport Cost is less than X 337, then the GMH flow can be increased 340 (see also FIG. 3F). If the GMH concentration/Transport Cost is greater than Y 347, then the GMH flow can be decreased 350 (see also FIG. 3G). After adjusting the GMH flow 340, 350, step 315 is continued at 355. Thus, at step 355 the change in GMH flow is related back to the procedure shown in FIG. 3A at step 315, and in particular the requirement to keep the algae growing in a particular phase. In an embodiment of the invention, the average cost including the cost of transporting for the 10-12 days before the intrachannel fractionation stage begins to produce significant amounts of BPDWA can be incorporated into the calculated cost. In an alternative embodiment of the invention, the average cost excluding the cost of transporting for the 10-12 days before the intrachannel fractionation stage begins to produce significant amounts of BPDWA can be calculated. In an alternative embodiment of the invention, the size of the intrachannel fractionation stage can be chosen based on the pond size, the transport rate, the settling rate, and/or the removal efficiency. In another alternative embodiment of the invention, when the algae are in the appropriate growth conditions it can take less than 10 days to allow biomass recovery from the intrachannel fractionation stage.

Figure 3E:
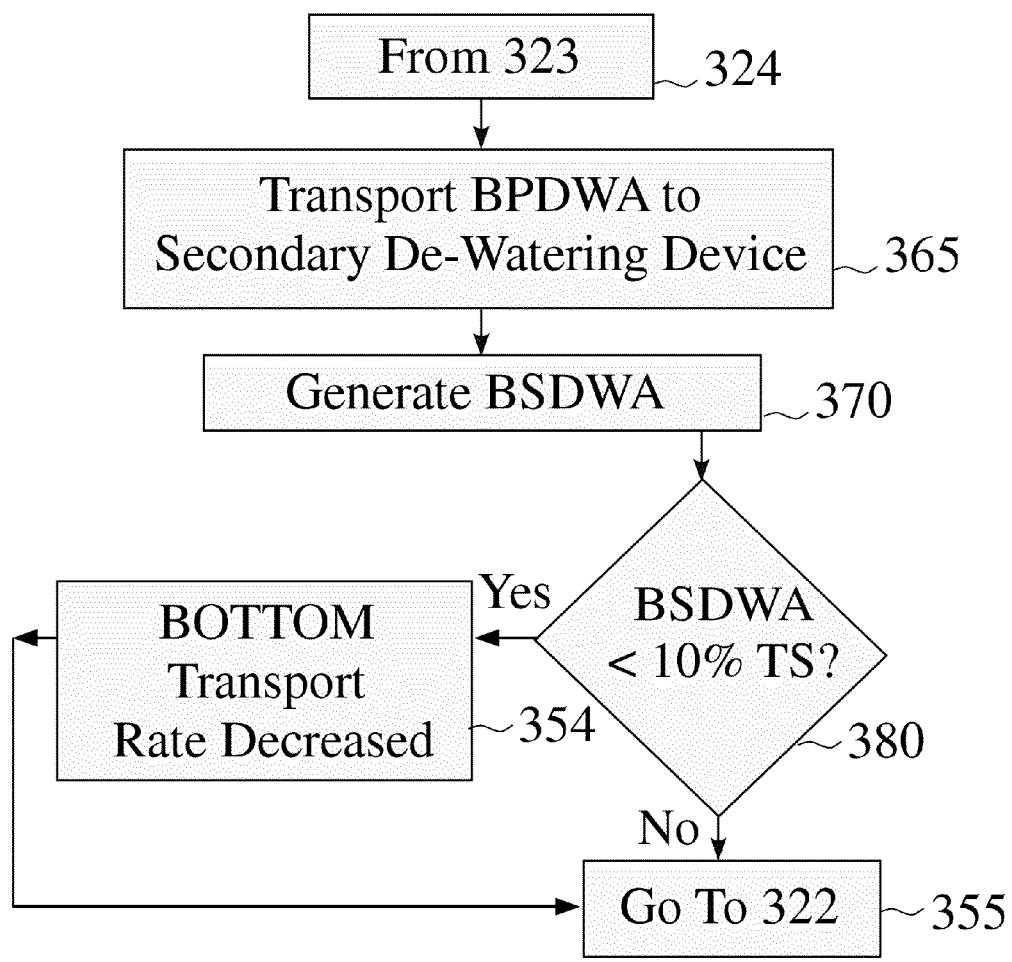
FIG. 3(E) is a flowchart showing a procedure used to optimize primary de-watering of GMH based on the bottom secondary de-watered algae (BSDWA) with an in-line PDWD according to an embodiment of the invention.

In an embodiment of the invention, the primary de-watering of GMH based on the secondary DWA can be optimized according to an embodiment of the invention. In FIG. 3(E) the BPDWA is transported to a secondary de-watering device (SDWD) 365. The BPDWA is further concentrated in the SDWD. Based on the total solids in the bottom secondary DWA (BSDWA) generated 370, different actions can be taken. If the BSDWA concentration is below 10% TS 380, the BOTTOM transport rate can be decreased 354. After adjusting the BOTTOM transport rate 354, step 322 is continued at 355. The change in BOTTOM transport rate can be related back to the procedure shown in FIG. 3A at step 322, and in particular the requirement to keep the algae growing in a particular phase 320.

Figure 3F:
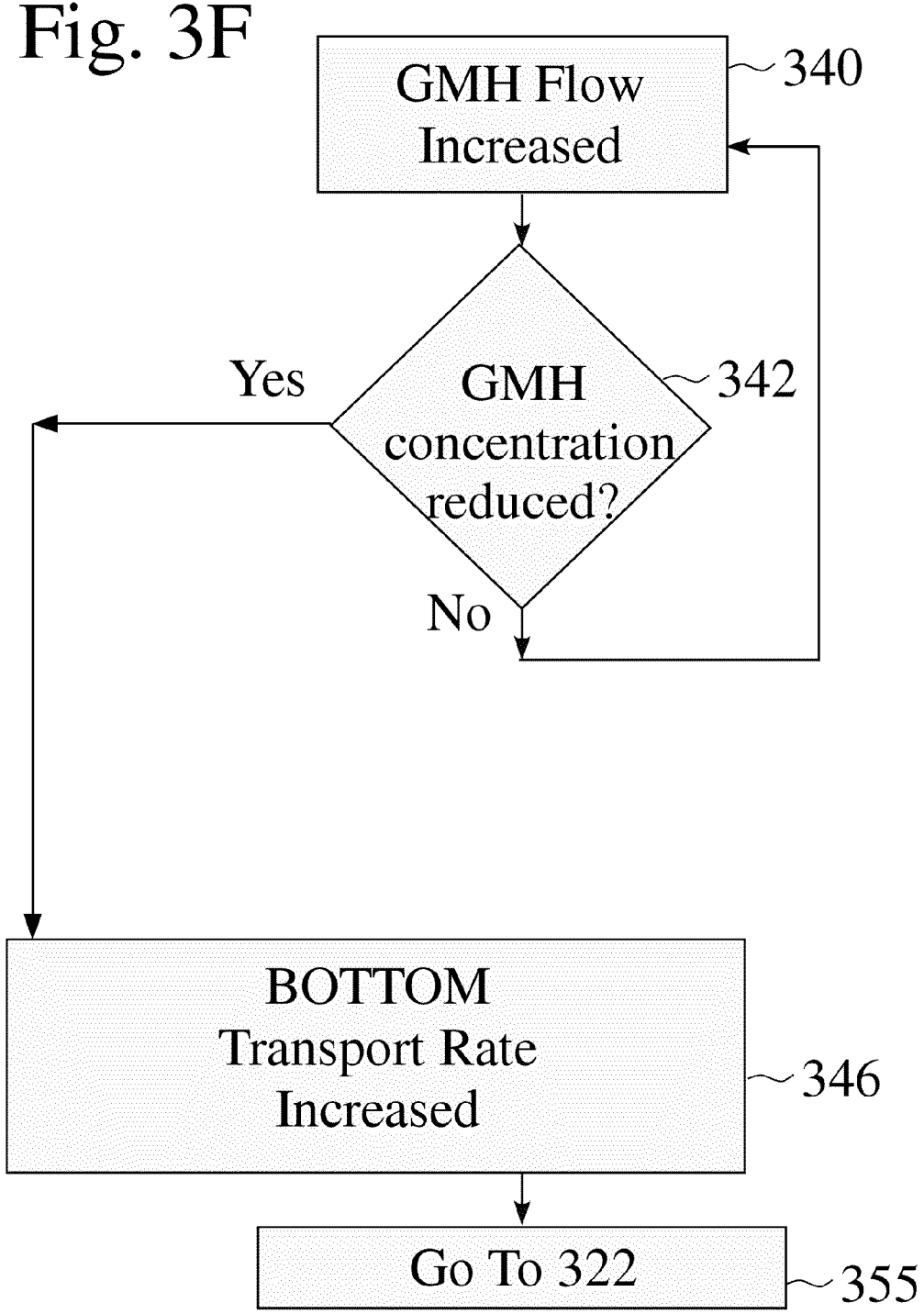
FIG. 3(F) is a flowchart showing a procedure used to increase the GMH flow with an in-line PDWD as required in the flowcharts shown in FIG. 3(B), FIG. 3(E) and FIG. 3(H) according to various embodiments of the invention.
Figure 3G:
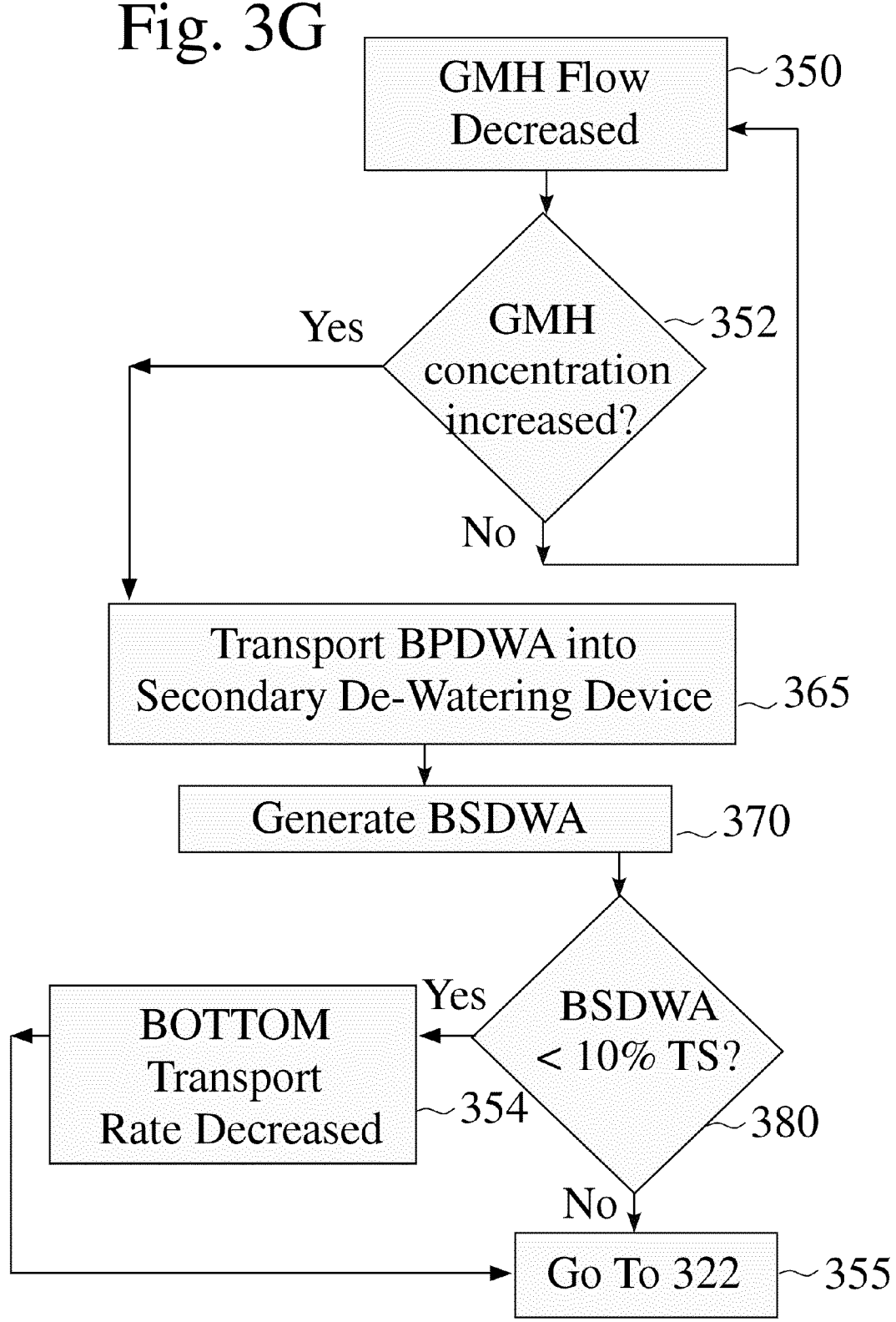
FIG. 3(G) is a flowchart showing a procedure used to decrease the GMH flow with an in-line PDWD as required in the flowcharts shown in FIG. 3(B), FIG. 3(E) and FIG. 3(H) according to various embodiments of the invention.

In FIG. 3F and FIG. 3G the GMH flow can be varied based on the amount of algae harvested in either the BPDWA, or the BSDWA, or some composite measure involving one of these measures and/or the pumping cost. A person having ordinary skill in the art after having read the specification would understand that the GMH flow and the BOTTOM transport rate can be independently adjusted to increase or decrease the amount of algae harvested. Similarly, the AGM flow and the BOTTOM transport rate can be independently adjusted to increase or decrease the amount of algae harvested. Also, the AGM flow and the BOTTOM transport rate can be adjusted in combination to increase or decrease the amount of algae harvested. Finally, the GMH flow and the BOTTOM transport rate can be adjusted in combination to increase or decrease the amount of algae harvested. In FIG. 3F and FIG. 3G the GMH flow and BOTTOM transport rate can be varied based on the GMH flow or the BOTTOM transport rate. When removing more solids or more concentrated solids from the BPDWA, a mechanized transport method can be incorporated to assist gravity feeding to the SDWD. In FIG. 3F the GMH flow can be increased 340 when the GMH concentration is not reduced 342 by an increase in the GMH flow 340. Alternatively, if the GMH concentration is reduced 342 by an increase in the GMH flow 340 then the BOTTOM transport rate can be increased 346. After adjusting the BOTTOM transport rate 346, step 322 is continued at 355. Thus, the change in BOTTOM transport rate can be related back to the procedure shown in FIG. 3A at step 322, and in particular the requirement to keep the algae growing in a particular phase 320. In FIG. 3G the GMH flow can be decreased 350 when the GMH concentration is increased 352 by a decrease in the GMH flow 350. Alternatively, if the GMH concentration is increased 352 by a decrease in the GMH flow 350 then the BPDWA can be transferred to a SDWD to generate BSDWA 365. Based on the total solids in the BSDWA generated 370, different actions can be taken. If the BSDWA concentration is below 10% TS 380, the BOTTOM transport rate can be decreased 354. After adjusting the BOTTOM transport rate 354, step 322 is continued at 355. Thus, a decrease in GMH can be related to a change in BOTTOM transport rate which can be related back to the procedure shown in FIG. 3A at step 322, and in particular the requirement to keep the algae growing in a particular phase 320.

Figure 3H:
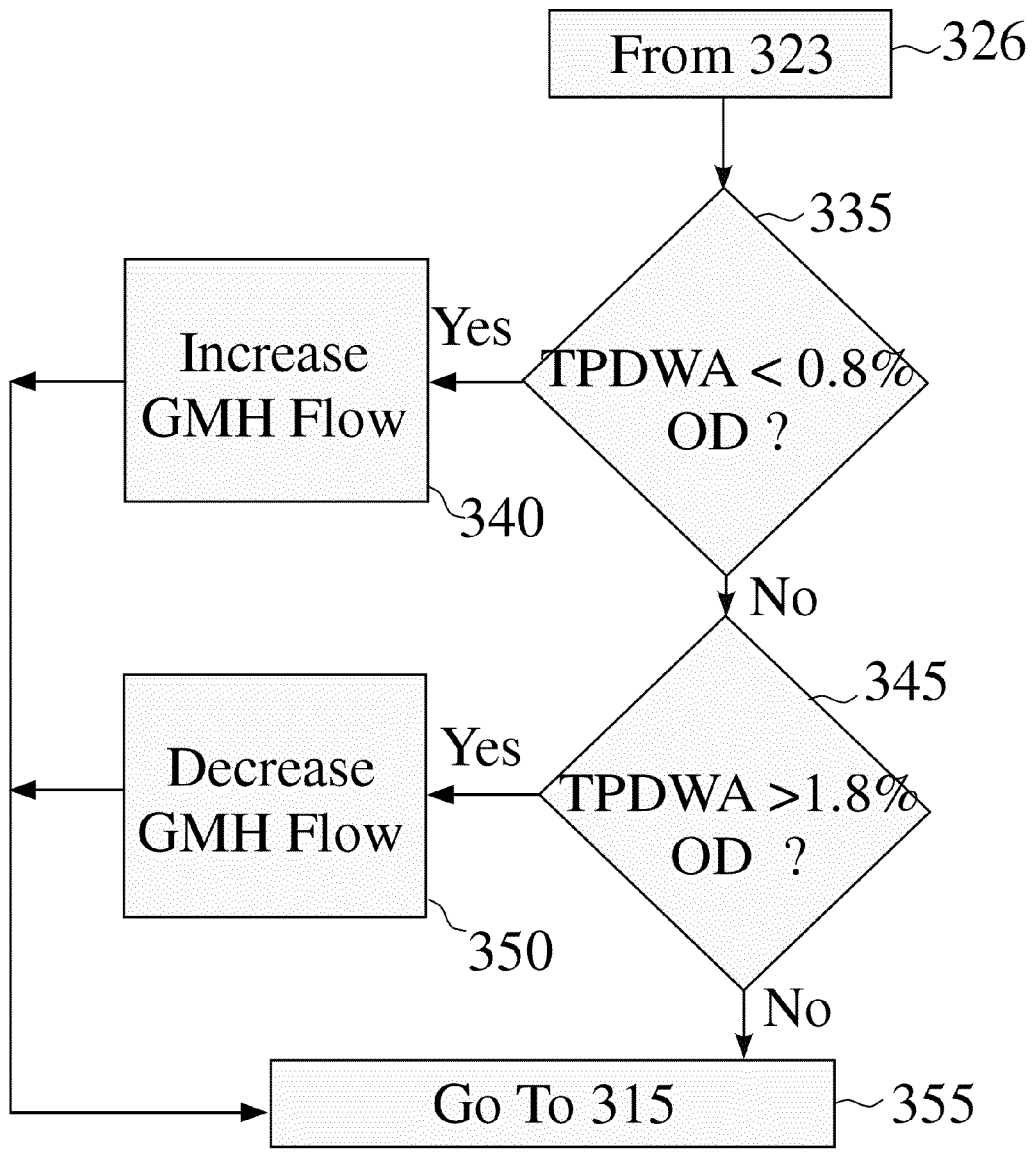
FIG. 3(H) is a flowchart showing a procedure used to optimize primary de-watering of GMH based on the top primary de-watered algae (TPDWA) with an in-line PDWD according to an embodiment of the invention.
Figure 3J:
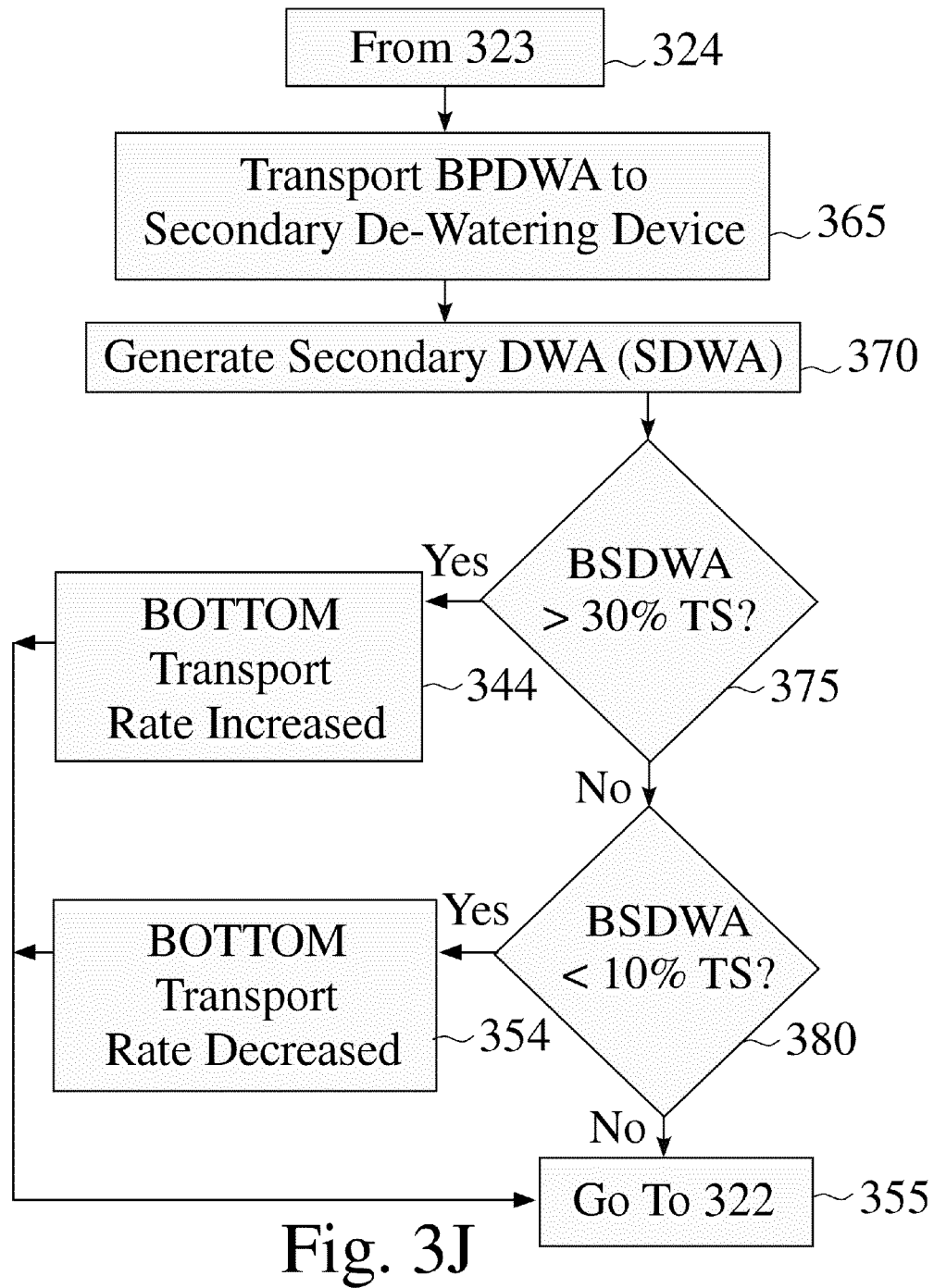
FIG. 3(J) is a flowchart showing a procedure used to optimize primary de-watering of GMH with an in-line PDWD based on the secondary de-watered algae (SDWA) according to an embodiment of the invention.

In an embodiment of the invention, from step 323 a test can be carried out as shown in FIG. 3H, 324. If the TPDWA concentration is below 0.8 OD 335, the GMH flow can be increased 340. Alternatively, if the TPDWA concentration is above 1.8 OD 345, the GMH flow can be decreased 350. After adjusting the GMH flow 340, 350, step 315 is continued at 355. In an embodiment of the invention, from step 323 a test can be carried out as shown in FIG. 3J, 324. The BPDWA can be transported to a secondary dewatering device 365. The BOTTOM transport rate can be increased 344 if the BSDWA concentration rises above 30% TS 375 or the BOTTOM transport rate can be decreased 354 if the BSDWA concentration falls below 10% TS 380. After adjusting the BOTTOM transport rate 344, 354, step 322 is continued at 355.

Figure 3K:
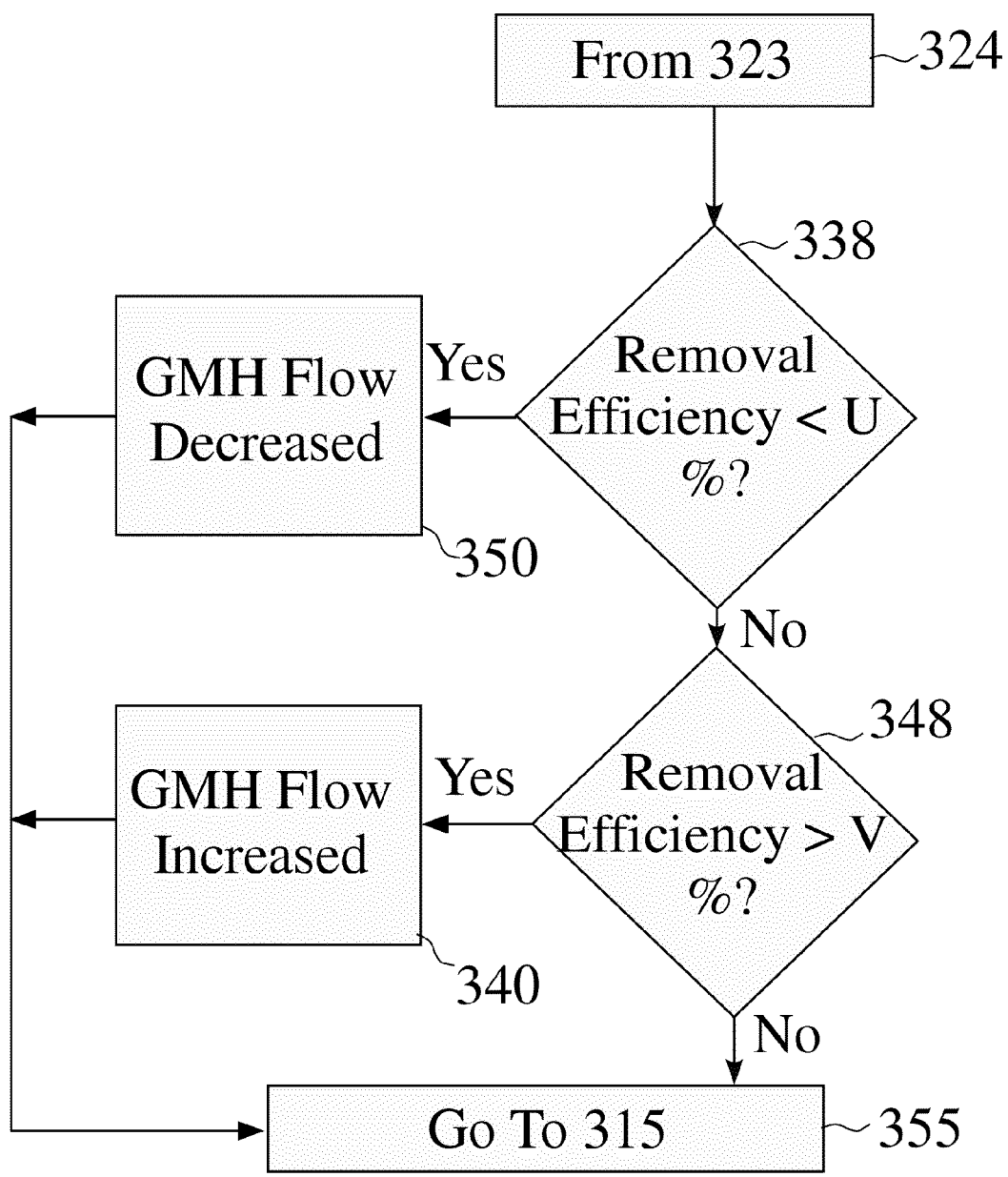
FIG. 3(K) is a flowchart showing a procedure used to optimize primary de-watering of GMH with an in-line PDWD based on the removal efficiency according to an embodiment of the invention.

In an embodiment of the invention, from step 323 a test can be carried out as shown in FIG. 3K, 324. If the pond efficiency is below U % 338, the GMH flow can be decreased 350. Alternatively, if the pond efficiency is above V % 348, the GMH flow can be increased 340. After adjusting the GMH flow 340, 350, step 315 is continued at 355. In an embodiment of the invention, the GMH flow can be decreased when U is set at 10%. In an embodiment of the invention, the GMH flow can be increased when V is set at 70%. In an embodiment of the invention, the pond efficiency (PE) can be given by PE=(1−([TPDWA]/[GMH]))*100, where [TPDWA] is the TPDWA concentration in OD and [GMH] is the GMH concentration in OD.

In various embodiments of the invention, one or more of the procedures shown in FIGS. 3B-3K can be used to help optimize one or both the GMH flow and/or the BOTTOM transport rate to maximize the algae harvest. In various embodiments of the invention, the intrachannel fractionation stage is not used as a water fractionation stage would be used in the water aeration and sludge removal industry. In an embodiment of the invention, the intrachannel fractionation stage is not used as would be used in the waste water industry.

Example 1

A 620 m² open pond (pond A) with a depth of 25 cm+−5 cm which has a volume of 155 m³ (40,950 gallons, or 155,000 L) is used to grow algae. A 932 m² open pond (pond B) with a depth of 25 cm+−5 cm which has a volume of 155 m³ (40,950 gallons, or 155,000 L) is used to grow algae. The fractionation tank manufactured by Met-Chem is typically used as part of a wastewater treatment system for settling metals out of waste water prior to discharge of the waste water. The fractionation tank is constructed of carbon steel. In an embodiment of the invention, the internal plate pack is set at 60 degrees for optimum settling and is constructed of HDPE plastic. FIG. 2B shows the fractionation tank 210. The Met-Chem 8'×16' (10' height) fractionation tank has a total capacity of 1280 cubic feet (9575 gallons, or 36,200 L) and can be filled through a 3 inch inlet 220 with GMH pumped from the AGM grown in the 620 m² open pond. The open pond is located in Ohio. The GMH can be continually pumped from the first pond to the fractionation tank (with exceptions for maintenance, operational and service related shutdowns to the fractionation tank 210) throughout the day and night from March thru to November in Ohio. The GMH can be continually pumped from pond B to the fractionation tank (with exceptions for maintenance, operational and service related shutdowns to the fractionation tank 210) throughout the day and night from March thru to November in Ohio. In 2009/2010, shutoffs occurred so that data were obtained from September to November 2009 and February to November 2010. The GMH flowed out of the fractionation tank through 3 inch outlets 250. The BPDWA is removed after settling through second exits 260 and 261. The BPDWA can be pumped or gravity fed into a secondary de-watering process. The TPDWA exiting the outlet 250 was returned to the open pond to be re-used for algaculture.

The concentration of the algae in the media can be measured using a spectrophotometer (Hach DR2700) irradiating a cell (1 cm path length) at 600 nm and comparing the absorption of this wavelength with a blank cell of water.

The GMH was circulated through the fractionation tank from the first pond but no BPDWA was removed until the GMH had reached approximately 0.5 OD. In an embodiment, it took approximately 10 days of pumping through the fractionation tank before the GMH in open pond A had reached a concentration where sufficient BPDWA was collecting in the fractionation tank. Unexpectedly, approximately two (2) to three (3) days after the open pond B had reached log phase growth of the algae population, a critical mass of algae can settle in the fractionation tank. It was the presence of this critical mass of algae in the bottom of the fractionation tank cone that enabled significant harvesting of algae. This is exemplified by the fact that the fractionation tank can be operated within 24 hours when either pond A or B has a critical mass of algae and the resulting GMH has greater than 0.5 OD. During the approximately 10 days prior to establishing the log phase growth, the BPDWA collected was negligible. After the approximately 10 days, the harvesting was between approximately 20 and 150 kg/day (wet weight) and a BPDWA (second) pump (or gravity feed) was required to continuously remove the BPDWA from the fractionation tank to a SDWD.

Example 2

A clarifier is typically used to reduce the particulate in waste water by an order of magnitude or more (e.g., from 100,000 p.p.m. to less than 1,000 p.p.m.). By operating a fractionation tank at approximately 50 GPM, the efficiency of settling (ES) can be between approximately 5 and 25%. In an embodiment of the invention, the ES can be between approximately 5 and 60% (where ES=(1−([TPDWA]/[GMH]))*100, where [TPDWA] is the TPDWA concentration in OD and [GMH] is the GMH concentration in OD, see Table II above). Unexpectedly, it was found that although the flow rate was too fast to allow complete settling of the algae, the primary dewatering resulted in an increase in the BPDWA collected. Unexpectedly, the increase in BPDWA outweighed the cost of pumping the GMH through the fractionation tank at the faster rate. Using a fractionation tank for settling but not clarification was not known in the art.

Example 3

In an embodiment of the invention, it was found that using a fractionation step can reduce the cost of dewatering the algae. That is, the pumping costs associated with the fractionation tank and the cost of centrifuging the PDWA can be significantly less than the cost of centrifuging the GMH directly. Using a centrifuge with a capacity of 2 GPM can require between 25 and 40 times as many centrifuge hours of operation depending on the flow rate of the fractionation tank (operating at 50-80 GPM). Accordingly, a centrifuge acting as the sole dewatering means treats between 1/25 and 1/40 of the amount of GMH. Thus, the fractionation tank reduces the amount of water that needs to be treated with a centrifuge while at the same time reducing the cost of running the centrifuge. This is a significant cost saving. In addition, using a centrifuge allows all of the solids to be recovered, but does not allow the return of non-disturbed immature algae cells to the pond for re-seeding of the pond. Further, the centrifuge does not select for dense algae in the same manner as the fractionation stage. Accordingly, the use of the fractionation tank can offer the ability to (i) select dense algae for harvesting and (ii) re-seed the pond; advantages over using a secondary dewatering process such as a centrifuge that were unexpected.

Example 4

In an embodiment of the invention, the pond can be allowed to go into different phases of growth to allow harvesting of different characteristic algae. In an embodiment allowing the pond to go into stationery phase can be used to increase the lipid content of the algae harvested. Further, allowing the pond to go into the stationary phase can enable higher yields as the flow rate is increased and more algae accumulate in the pond, an increase in the efficiency of settling in the fractionation pond results. In another embodiment of the invention, the pond can be kept in log phase growth to maximize the biomass growth. In another alternative embodiment of the invention, the pond can be kept in log phase growth to maximize the consumption of carbon dioxide. In another alternative embodiment of the invention, the pond can be kept in log phase growth to increase the trading credits available for the consumption of carbon dioxide.

Example 5

In an embodiment of the invention, the fractionation tank can be operated with plates in one side and without plates on the other side. It is estimated that the plated side had approximately 280 sq ft of settling area, with 2 inch spacing, while the unplated side had about 44 sq ft of settling area, with a distance of nearly 10 feet from top to bottom. Table III shows the yield of algae obtained from a fractionation tank in which one side of the fractionation tank was installed with settling plates (right side) and the other side did not contain settling plates (left side). The BPDWA obtained from each side of the fractionation tank was separately sent to a secondary dewatering process (centrifugation) and the resulting pellets weighed. As shown in Table III, it was unexpectedly found that the yield of algae obtained from the fractionation tank did not correlate with the area of the settling plates 240 in each side of the fractionation tank (see FIGS. 2B and 2C). In a clarifier the settling plates increase the downflow of particles in settling and therefore the settling process can be improved by increasing the area of the settling plates. It was found that the overall yield from the side of the fractionation tank without the settling plates installed (Unplated) was lower than the overall yield from the side of the fractionation tank with the settling plates installed (Plated). However, it was unexpected that the difference between the 'Unplated' side and the 'Plated' side did not correlate with the area of the settling plates in each side of the fractionation tank. Thus operating a fractionation tank without settling plates counter intuitively leads to significant settling of algae from the algae growth media entering the fractionation tank. While the ratio of sq. ft. of settling area was approximately 280:44, the ratio of algae harvested as shown in Table III was approximately 2:1. In the unplated side, the non-turbulent flow in the downward direction results in significant settling. Using a clarifier for fractionation of algae, rather than clarification of wastewater, is not known in the art. Clarifiers clarify top overflow from wastewater. In contrast, a fractionation stage is reducing the concentration of algae in the top fraction compared with the bottom fraction. Unexpectedly, the separation involves mature cells being concentrated in the bottom fraction and the less mature cells being concentrated in the top fraction allowing the less mature cells to be easily returned to culture. The advantage of removing the mature cells is not simply confined to increased productivity for the particular batch being harvested. Similarly the advantage of reseeding the pond with the less mature cells extends for many reproductive cycles forward. By removing mature cells, the algae in the pond no longer have the capability to signals or otherwise effect a shift from the log growth phase to a static growth phase. This allows for the continuous culture of algae for long periods of time. The removal of the mature cells also removes the instrument or a vital component in the mechanism for slowing down the growth phase. Further, removing the main component of a clarifier to improve the settling and obtaining significant harvested material is an unexpected result. In an embodiment of the invention, the fractionation tank can be operated with plates in both sides. In an alternative embodiment of the invention, the fractionation tank can be operated with no plates in either side. In another embodiment of the invention, the fractionation tank can be operated with plates in a portion and no plates in another portion of the fractionation tank.

TABLE III

Bottom Secondary De-Watered Algae (BSDWA) obtained from the Right (Plated) compared with the Left (Unplated) Cone of a Fractionation Tank as a function of the Algae Growth Media (AGM) over a ten (10) day period

| Day | AGM Concentration (OD) | Right Cone Plated (kg) | Left Cone Unplated (kg) | Flow (GPM) |
|---|---|---|---|---|
| 09 | 0.92 | 11.953 | 7.551 | 50 |
| 10 | 0.98 | 30.563 | 14.284 | 20 |
| 11 | 1.1 | 30.368 | 14.463 | 30 |
| 12 | 0.8 | 24.087 | 19.560 | 40 |
| 13 | 0.7 | 15.147 | 5.701 | 45 |
| 14 | 0.8 | 9.960 | 7.667 | 50 |
| 15 | 1.0 | 30.847 | 21.943 | 60 |
| 16 | 0.92 | 44.321 | 27.791 | 65 |
| 17 | 0.73 | 54.143 | 16.045 | 75 |
| 18 | 0.92 | 24.919 | 15.444 | 60 |
| 19 | 1.3 | 19.256 | 11.869 | 60 |
| 20 | 1.1 | 44.189 | 10.444 | 60 |

Example 6

The introduction of the primary de-watering step which resulted in a higher concentration of BPDWA was found to increase the performance of a number of secondary dewatering steps. In an embodiment of the invention, using centrifugation as the secondary de-watering step, increases the concentration of the BPDWA from approximately 2% to approximately 15% TS.

Example 7

Covering the Fractionation Tank

It was noticed that algae was floating to the top of the fractionation tank. The floating characteristics were assumed to be at least partially induced by available sunlight. In an embodiment of the invention, in order to reduce the floating characteristics a cover was placed on the fractionation tank. The cover blocked sunlight and increased the biomass recovery. When the fractionation tank was covered to limit sunlight availability to algae in the fractionation tank, the cover either reduced the tendency to float or increased the tendency of the algae to settle. In an alternative embodiment of the invention, the algae in an uncovered fractionation tank is harvested at night to reduce the algae flotation characteristics.

In an embodiment of the invention, it was noticed that algae settling characteristics increased when a cover was placed on the fractionation tank. A cover can insulate the fractionation tank and thereby keep in or keep out the heat. A cover can also limit solar heating of the fractionation tank. When the fractionation tank was covered to limit sunlight availability to algae in the fractionation tank, the cover increased the settling characteristics of the algae through a thermal mechanism.

In an embodiment of the invention, it was observed that the fastest growing pond had less flocculation and settling. However, on cloudy days the algae seemed to settle and move more into the water column than on sunny days. In an embodiment of the invention, a cover was placed on the fractionation tank. The cover blocks sunlight which can aid in settling and the cover can keep in heat. In an embodiment of the invention, a portion of the pond can be covered prior to harvesting to reduce the algae flotation characteristics or increase the tendency of the algae to settle.

Example 8

Adjusting the GMH Pumping Time to Sustain Log Phase Growth

In an embodiment of the invention, the rate of flow is adjusted to keep the concentration (measured in OD) in the algae pond within a defined range. In an embodiment of the invention, the size of the pond and/or the pump rate (see FIGS. 1F and 1G) can be varied to allow the fractionation tank to be run almost continuously (i.e., approximately 24 hours per day). In an alternative embodiment the fractionation tank is run 20 to 24 hours per day. In an alternative embodiment the fractionation tank is run 10 to 20 hours per day. In an embodiment of the invention, the TOP pump rate is adjusted to keep the concentration (measured in OD) in the pond within a defined range of log phase growth and the fractionation tank to be run approximately 24 hours per day. In an embodiment of the invention, the size of the pond is adjusted to keep the concentration (measured in OD) in the pond within a defined range of log phase growth and the fractionation tank to be run approximately 24 hours per day.

FIGS. 1B-1J show a series of flowcharts of different procedures that can be used to optimize biomass recovery according to a variety of embodiments of the invention. In various embodiments of the invention, the concentration of one or more parameters selected from the group consisting of AGM concentration, GMH concentration, TPDWA concentration, BPDWA concentration, TSDWA concentration, BSDWA concentration, AGM condition, GMH condition, TPDWA condition, BPDWA condition, TSDWA condition, BSDWA condition, TOP pump cost of operation, BOTTOM pump cost of operation, TOP pump capital cost, BOTTOM pump capital cost.

Figure 1B:
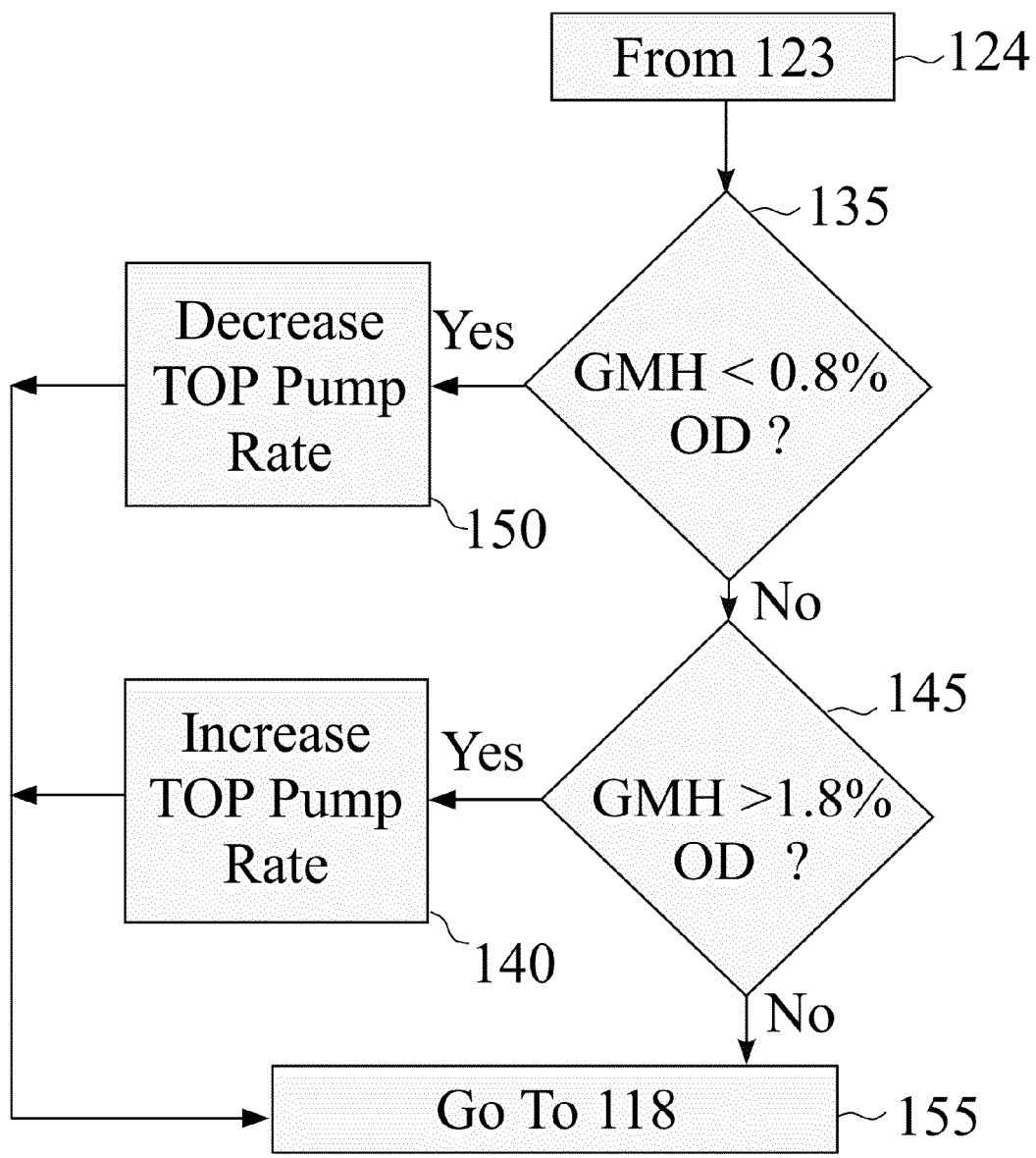
FIG. 1(B) is a flowchart showing a procedure used to optimize primary de-watering of growth media to be harvested (GMH) according to an embodiment of the invention.

In FIG. 1(B) the GMH is passed through the fractionation tank and the TPDWA is continuously recycled back to the pond. Based on the concentration of the TPDWA different actions can be taken.

In an embodiment of the invention, from step 123 a test can be carried out as shown in FIG. 1B, 124. The TOP pump rate can be decreased 150 (see also FIG. 1G) if the GMH concentration falls below 0.8 OD 135 or the TOP pump rate can be increased 140 (see also FIG. 1F), if the GMH concentration increases above 1.8 OD 145. After adjusting the TOP pump rate 140, 150, step 118 is continued at 155. Thus, at step 155 the change in TOP pump rate can be related back to the procedure shown in FIG. 1A at step 118, and in particular the requirement to keep the algae growing in a particular stage of growth.

In an embodiment of the invention, with a GMH concentration of 1.2 OD, the TOP pump rate would only be adjusted if the reduction in OD was greater than 20%. This reflects the unexpected discovery that significant amounts of algae can be harvested with only a minimal reduction in the concentration of the algae being pumped through the fractionation tank. The difference between a GMH of 1.2 OD and a TPDWA of 1.0 OD would not be apparent to the untrained human eye. Importantly, as shown in Tables II and III, the 20% reduction in the GMH compared with the TPDWA can result in significant biomass recovery.

In this embodiment, a flow rate between 50-70 gallon per minute (GPM) results in considerable concentration of algae present in the aqueous algae medium exiting through the outflow. In an embodiment of the invention, the rate of flow is adjusted to keep the concentration of the total solids (TS) drawn from the fractionation tank within a defined range.

Figure 1C:
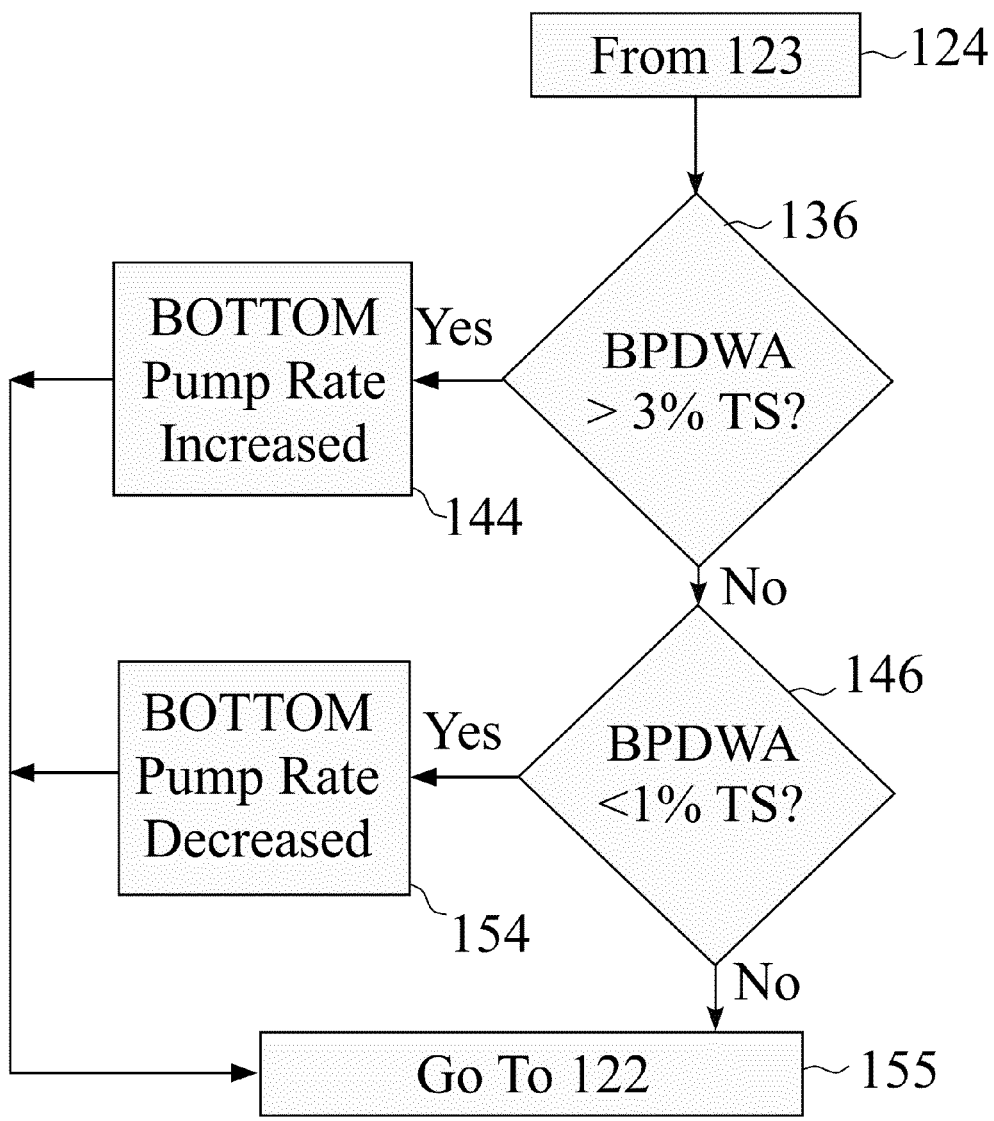
FIG. 1(C) is a flowchart showing a procedure used to optimize primary de-watering of GMH based on the bottom primary de-watered algae (BPDWA) according to an embodiment of the invention.

In an embodiment of the invention, the GMH flow rate is adjusted to keep the concentration of the TS in a defined range for a secondary dewatering step. FIG. 1(C) is a flowchart showing the procedure used to optimize primary de-watering of GMH and growth of the AGM based on the BPDWA according to an embodiment of the invention. In FIG. 1(C) the GMH is continuously pumped into the fractionation tank. The BPDWA is removed from the fractionation tank using pumping or gravity feed. In this embodiment of the invention, from step 123 a test can be carried out 124. The BOTTOM pump rate can be increased 144 if the BPDWA concentration is above 3% TS 136 or the BOTTOM pump rate can be decreased 154 if the BPDWA concentration falls below 1% TS 146. After adjusting the BOTTOM pump rate 144, 154, step 122 is continued at 155. At step 155 the change in BOTTOM pump rate can be related back to the procedure shown in FIG. 1A at step 122, and in particular the requirement to keep the algae growing in a particular growth phase.

In an alternative embodiment of the invention, if the BPDWA is greater than 5% TS, then the TOP pump rate can be increased. If the BPDWA is less than 0.7% TS, then the TOP pump rate can be decreased. In another alternative embodiment of the invention, if the BPDWA is greater than 10% TS, then the TOP pump rate can be increased. If the BPDWA is less than 0.2 OD, then the TOP pump rate can be decreased.

Figure 1D:
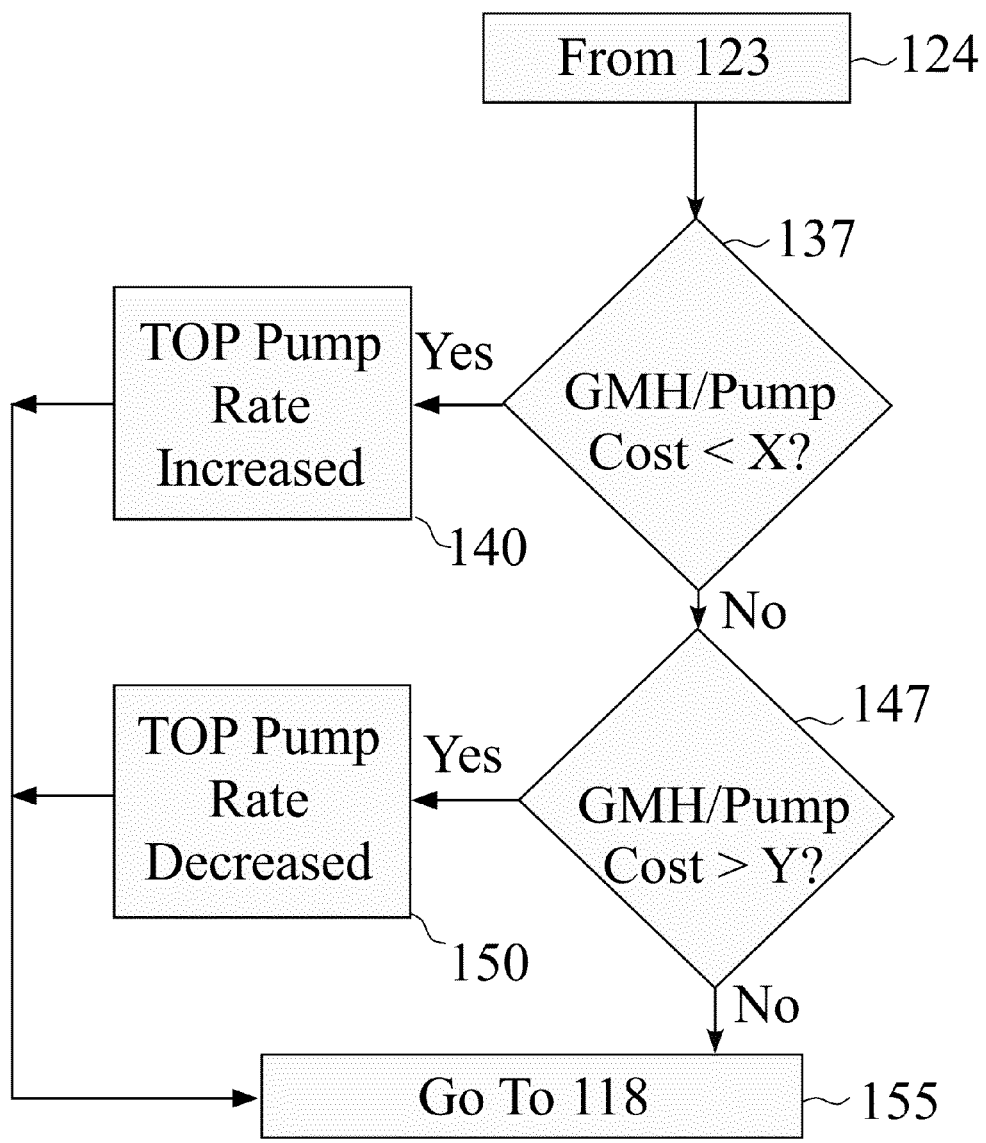
FIG. 1(D) is a flowchart showing a procedure used to optimize primary de-watering of GMH based on the ratio of the GMH to the pumping cost according to an embodiment of the invention.

FIG. 1(D) is a flowchart showing the procedure used to optimize primary de-watering of GMH and growth of the AGM based on the BPDWA and the cost of pumping the GMH from the pond thru the fractionation tank and back into the pond according to an embodiment of the invention. In FIG. 1(D) the GMH is continuously pumped from the pond into the fractionation tank and the TPDWA is continuously returned to the pond. The BPDWA is removed from the fractionation tank using pumping or gravity flow. Based on the ratio of the GMH concentration and the cost of pumping different actions can be taken. If the GMH/Pump Cost is less than X 137, then the TOP pump rate can be increased 140 (see also FIG. 1F). If the GMH/Pump Cost is greater than Y 147, then the TOP pump rate can be decreased 150 (see also FIG. 1G). After adjusting the TOP pump rate 140, 150, step 118 is continued at 155. Thus, at step 155 the change in TOP pump rate is related back to the procedure shown in FIG. 1A at step 118, and in particular the requirement to keep the algae growing in a particular phase. In an embodiment of the invention, the average cost including the cost of pumping for the 10-12 days before the fractionation tank begins to produce significant amounts of BPDWA can be incorporated into the calculated cost. In an alternative embodiment of the invention, the average cost excluding the cost of pumping for the 10-12 days before the fractionation tank begins to produce significant amounts of BPDWA can be calculated. In an alternative embodiment of the invention, the size of the fractionation tank can be chosen based on the pond size, the pump rate, the settling rate, and/or the removal efficiency. In another alternative embodiment of the invention, when the algae are in the appropriate growth conditions it can take less than 10 days to allow biomass recovery from the fractionation tank.

Figure 1E:
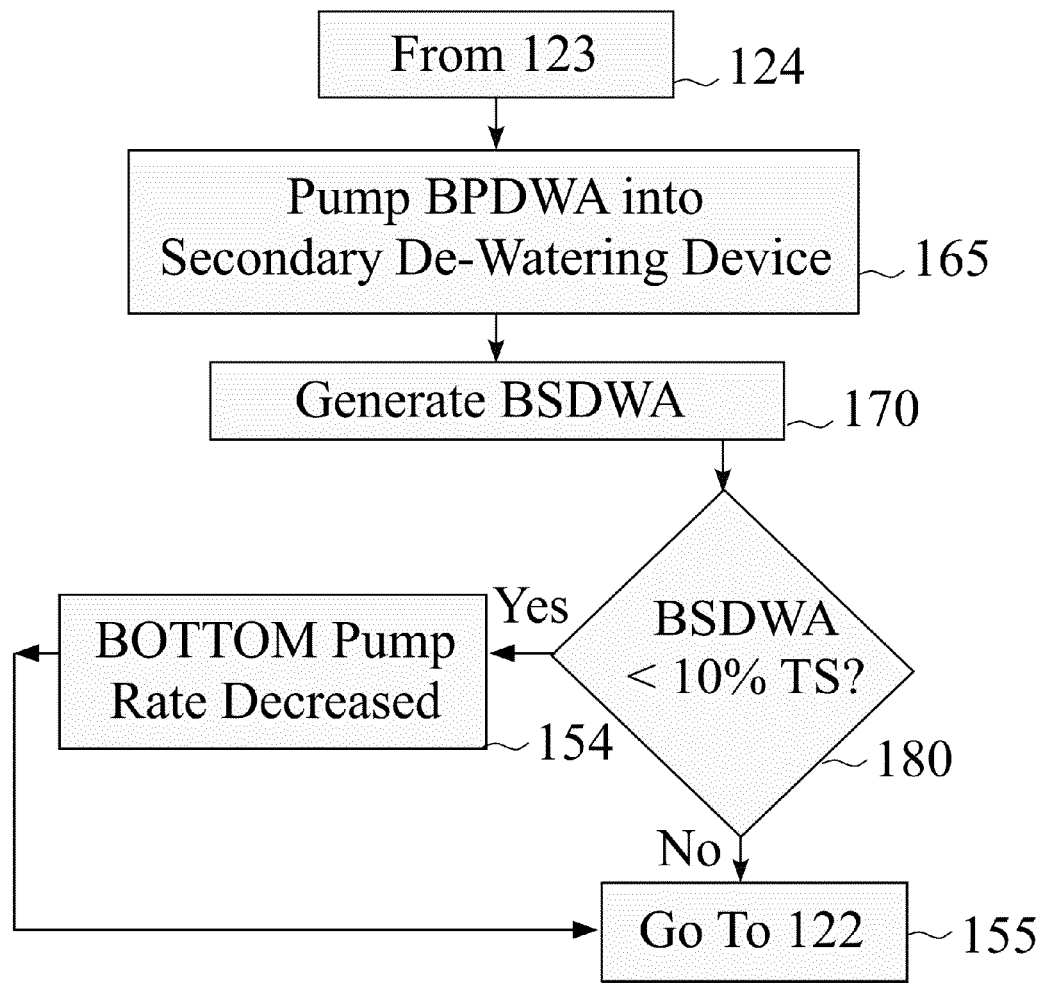
FIG. 1(E) is a flowchart showing a procedure used to optimize primary de-watering of GMH based on the bottom secondary de-watered algae (BSDWA) according to an embodiment of the invention.

In an embodiment of the invention, FIG. 1(E) is a flowchart showing the procedure used to optimize primary de-watering of aqueous growth medium based on the secondary DWA according to an embodiment of the invention. In FIG. 1(E) the BPDWA is pumped or gravity flowed and loaded into a secondary de-watering device (SDWD) 165. The BPDWA is further concentrated in the SDWD. Based on the total solids in the bottom secondary DWA (BSDWA) generated 170, different actions can be taken. If the BSDWA concentration is below 10% TS 180, the BOTTOM pump rate or gravity flow can be decreased 154. After adjusting the BOTTOM pump rate or flow rate 154, step 122 is continued at 155. The change in BOTTOM pump rate can be related back to the procedure shown in FIG. 1A at step 122, and in particular the requirement to keep the algae growing in a particular phase 120.

Figure 1G:
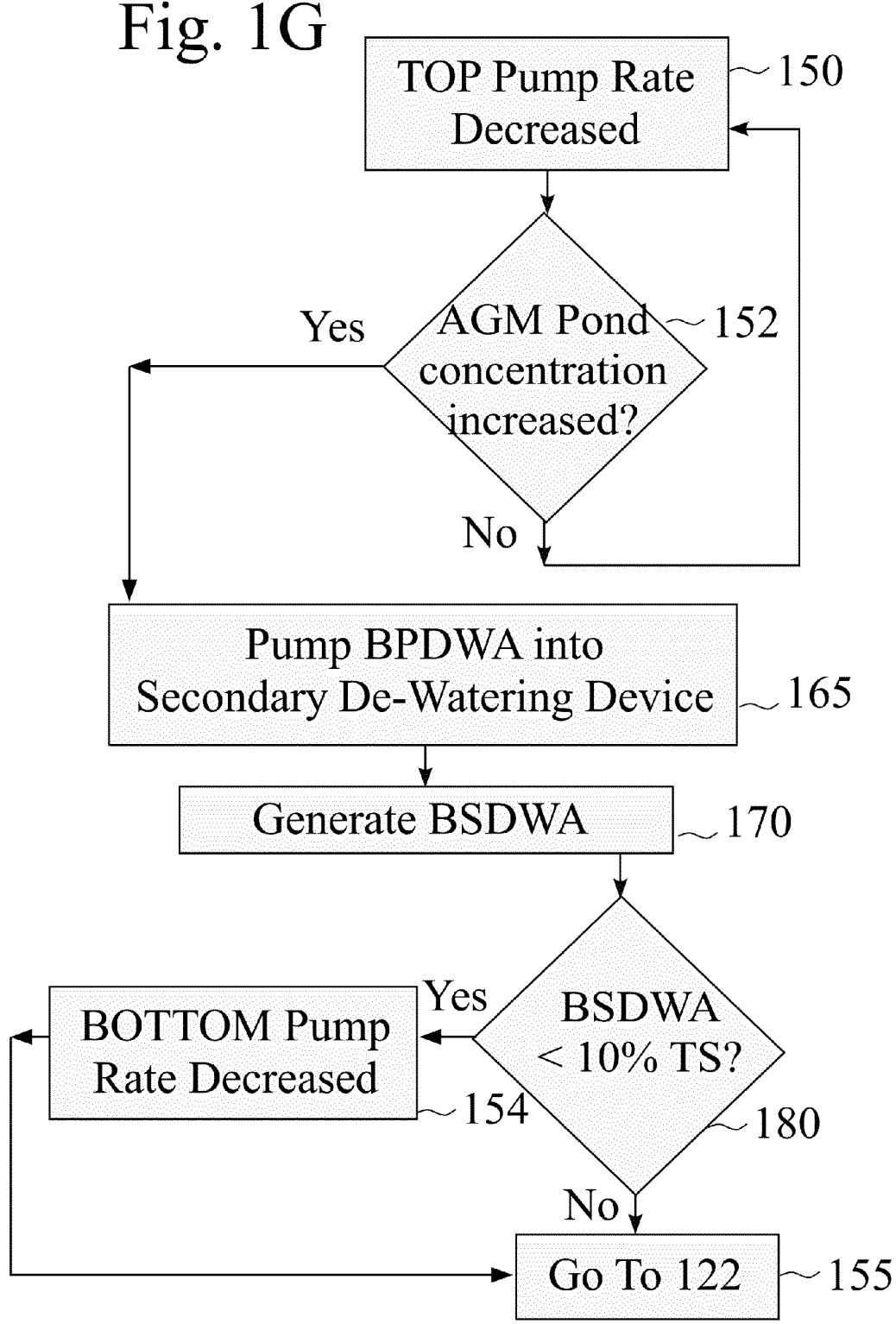
FIG. 1(G) is a flowchart showing a procedure used to decrease the TOP pump rate as required in the flowcharts shown in FIG. 1(B), FIG. 1(E) and FIG. 1(H) according to various embodiments of the invention.

In FIG. 1F and FIG. 1G the TOP pump rate can be varied based on the amount of algae harvested in either the BPDWA, or the BSDWA, or some composite measure involving one of these measures and the pumping cost. A person having ordinary skill in the art after having read the specification would understand that the TOP pump and the BOTTOM pump and/or BPDWA valve (when the BPDWA is gravity fed to the SDWD) can be independently or alternatively adjusted in combination to increase or decrease the amount of algae harvested. In FIG. 1F and FIG. 1G the TOP and BOTTOM pumping rate can be varied based on (i) the TOP pump rate or the BOTTOM pump rate, (ii) the TOP pump rate or the BPDWA valve aperture and (iii) the TOP pump rate, the BOTTOM pump rate and the BPDWA valve aperture. When removing more solids or more concentrated solids from the BPDWA, a pump can be incorporated to assist gravity feeding to the SDWD. In FIG. 1F the TOP pump rate can be increased 140 when the AGM concentration is not reduced 142 by an increase in the TOP pump rate 140. Alternatively, if the AGM concentration is reduced 142 by an increase in the TOP pump rate 140 then the BOTTOM pump rate can be increased 146. After adjusting the BOTTOM pump rate 146, step 122 is continued at 155. Thus, the change in BOTTOM pump rate can be related back to the procedure shown in FIG. 1A at step 122, and in particular the requirement to keep the algae growing in a particular phase 120. In FIG. 1G the TOP pump rate can be decreased 150 when the AGM concentration is increased 152 by a decrease in the TOP pump rate 150. Alternatively, if the AGM concentration is increased 152 by a decrease in the TOP pump rate 150 then the BPDWA can be pumped to transfer to a SDWD to generate BSDWA 165. Based on the total solids in the BSDWA generated 170, different actions can be taken. If the BSDWA concentration is below 10% TS 180, the BOTTOM pump rate or gravity flow can be decreased 154. After adjusting the BOTTOM pump rate or flow rate 154, step 122 is continued at 155. Thus, the change in BOTTOM pump rate can be related back to the procedure shown in FIG. 1A at step 122, and in particular the requirement to keep the algae growing in a particular phase 120.

Figure 1H:
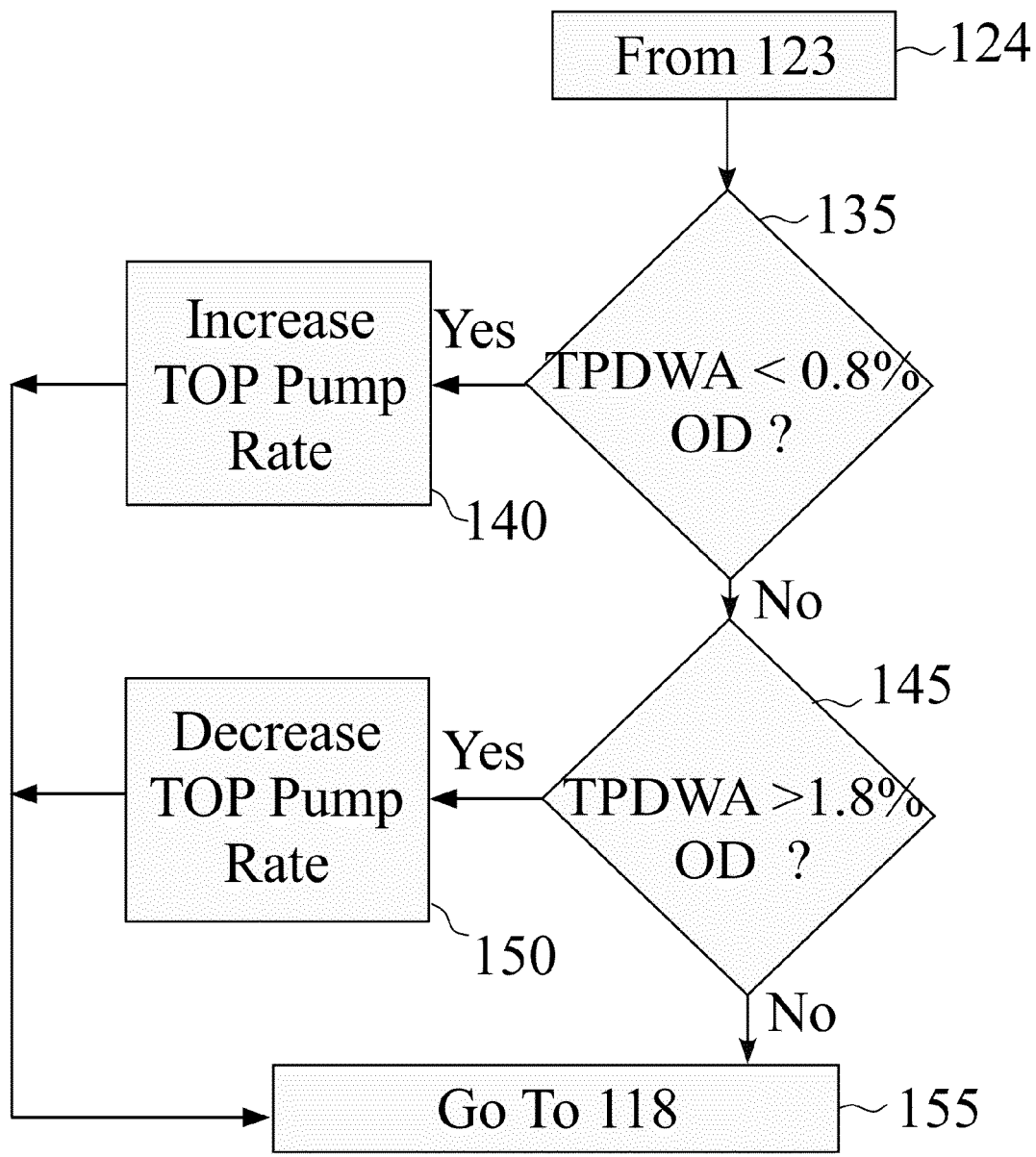
FIG. 1(H) is a flowchart showing a procedure used to optimize primary de-watering of GMH based on the top primary de-watered algae according to an embodiment of the invention.
Figure 1J:
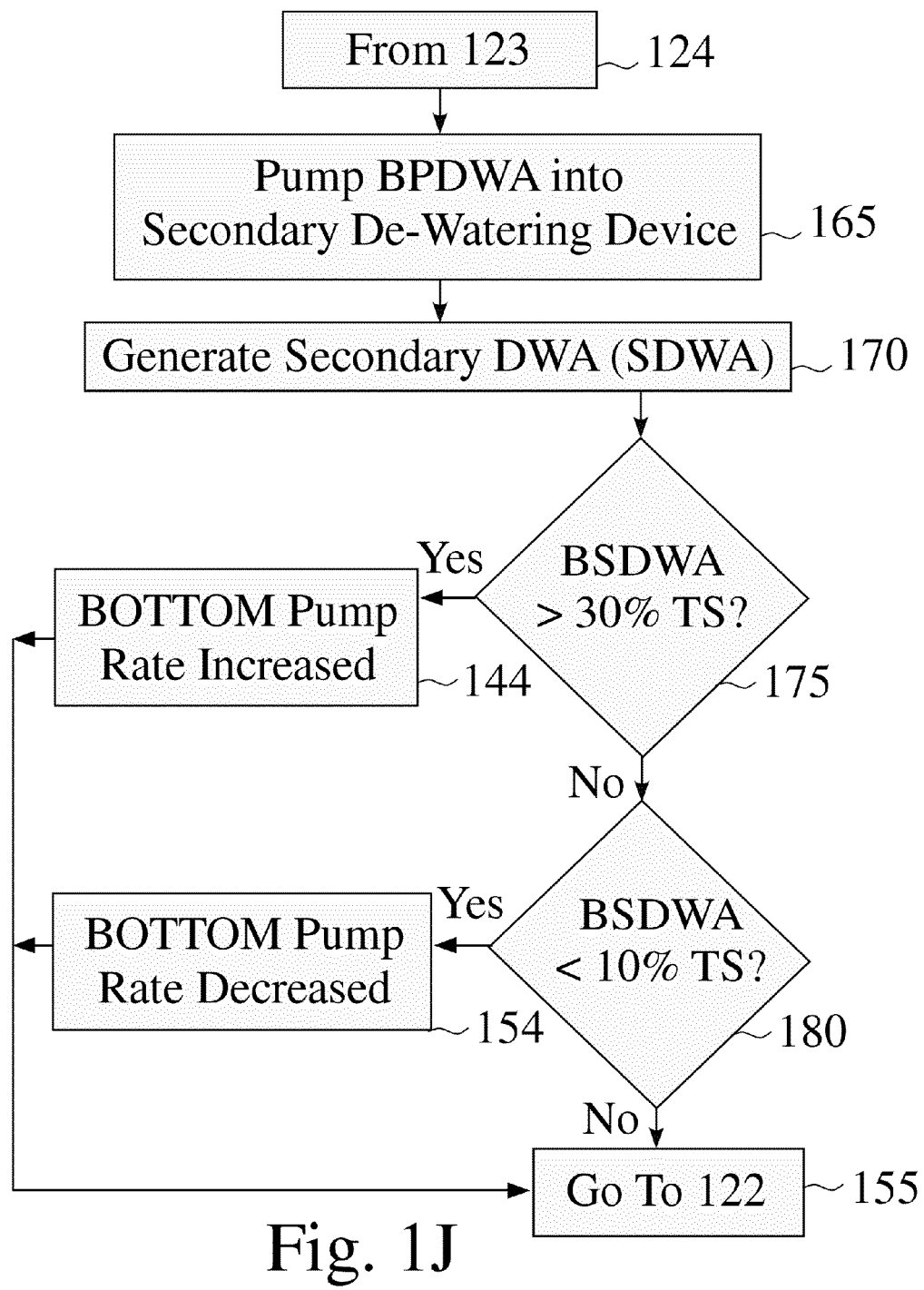
FIG. 1(J) is a flowchart showing a procedure used to optimize primary de-watering of GMH based on the secondary de-watered algae (SDWA) according to an embodiment of the invention.

In an embodiment of the invention, from step 123 a test can be carried out as shown in FIG. 1H, 124. If the TPDWA concentration is below 0.8 OD 135, the TOP pump rate can be increased 140. Alternatively, if the TPDWA concentration is above 1.8 OD 145, the TOP pump rate can be decreased 150. After adjusting the TOP pump rate 140, 150, step 118 is continued at 155. In an embodiment of the invention, from step 123 a test can be carried out as shown in FIG. 1J, 124. The BPDWA can be pumped into a secondary dewatering device 165. The BOTTOM pump rate can be increased 144 if the BSDWA concentration rises above 30% TS 175 or the BOTTOM pump rate can be decreased 154 if the BSDWA concentration falls below 10% TS 180. After adjusting the BOTTOM pump rate 144, 154, step 122 is continued at 155.

In an embodiment of the invention, from step 123 a test can be carried out as shown in FIG. 1K, 124. If the removal efficiency is below U % 138, the TOP pump rate can be decreased 150. Alternatively, if the removal efficiency is above V % 148, the TOP pump rate can be increased 140. After adjusting the TOP pump rate 140, 150, step 118 is continued at 155. In an embodiment of the invention, the TOP pump can be decreased when U is set at 10%. In an embodiment of the invention, the TOP pump can be increased when V is set at 70%. In an embodiment of the invention, the removal efficiency (RE) can be given by $RE = (1-([TPDWA]/[GMH]))*100$, where [TPDWA] is the TPDWA concentration in OD and [GMH] is the GMH concentration in OD.

In various embodiments of the invention, one or more of the procedures shown in FIGS. 1B-1K can be used to help optimize one or both the TOP pump rate and/or the BOTTOM pump rate to maximize the harvest. In various embodiments of the invention, the fractionation tank is not used as a water clarifier. In various embodiments of the invention, the fractionation tank is not used as a water clarifier would be used in the metal finishing industry. In an embodiment of the invention, the fractionation tank is not used as a typical water clarifier would be used in the waste water industry.

In various embodiments of the invention, the fractionation tank is used with faster flow rates than required to allow sufficient settling to clean water in a tank used as a water clarifier. Unexpectedly, it was found that by using a faster flow rate the aqueous algae growth medium in the pond can be kept above a level of 1.0 OD and solids can accumulate even though the efficiency of settling is relatively low (5-60%).

In an embodiment of the invention, a cover is placed on the fractionation tank to reduce heat loss in the fractionation tank. In an embodiment of the invention, a cover is placed on the fractionation tank to reduce the tendency of the algae to float on or towards the surface of the fractionation tank.

The type of fractionation tank that this separation and dewatering method uses is known as a clarifier and is used world-wide in sewage treatment facilities for sludge removal from wastewater. Its use in harvesting algae from mass algaculture has not been previously described.

In another embodiment, a method is provided for primary de-watering of algae from an aqueous growth medium, the method comprising introduction of the aqueous growth medium to a fractionation tank that includes a medium inlet, a medium outlet, one or more surfaces upon which the algae can settle by gravity and one or more baffles, wherein the configuration of the medium inlet, the medium outlet and the one or more baffles allows for enhanced exposure of the introduced medium to the one or more surfaces. In an alternative embodiment of the invention, the fractionation tank further includes an outlet by which the settled algae concentrate can be removed, wherein the introduction and removal of medium minimally disrupts the algae that has settled out by gravity. In an embodiment of the invention, the algae concentrate obtained from primary dewatering is further de-watered by centrifugation.

Parallel plate fractionation tank. The Met-Chem tank uses gravity in conjunction with the projected settling area of the 60 degree angle parallel plates to settle solids from a pretreated liquid flow. When the Met-Chem tank is used as a clarifier it meets EPA discharge limits for metal finishing wastes. When the Met-Chem tank is used as a clarifier, treated liquid flows first to the flocculation tank where polymer is added to promote flocculation growth, and then up through the settling plates where the solids settle out to the bottom sludge cones. When the Met-Chem tank is used as a clarifier, the clean water flows out through special laundering troughs to plant discharge or for polishing for water reuse. When the Met-Chem tank is used as a clarifier the solids are intermittently taken from the bottom cone to a filter press for further dewatering.

A circular clarifier tank manufactured by Siemens can be used to treat water or wastewater to remove particles and reduce TS to low levels. The Rim-Flo® center-feed clarifier had an overall hydraulic efficiency of 65%. Effluent suspended solids levels can be maintained below 20 p.p.m. at hydraulic loading up to 1,300 GPD/sq. ft./day. Effluent suspended solids levels below 15 p.p.m. can be achieved at levels of 800 GPD/sq. ft.

Elimination of the separate secondary clarifier and sludge return system by using an intrachannel clarifier at first appears to offer many advantages. Using any of these devices, however, has several implications relative to the design and operation of the facility that the designer must consider. The following sections discuss these various design tradeoffs.

A method of fractionating AGM comprises receiving AGM containing one or more species of algae in an open pond. All or a portion of the AGM comprising GMH is transferred into a PDWD, wherein the GMH enters the PDWD at a first flow rate. The GMH in the PDWD can be fractionated into at least a top fraction and a bottom fraction, wherein the PDWD fractionates based on at least the first flow rate and a settling rate of the algae, wherein at least one exit for the top fraction returns top fraction directly to the pond for algaculture and the bottom fraction is collected.

In various embodiments of the invention, the fractionation tank can be used to harvest cells, where the cells are cells capable of being grown in media. A person having ordinary skill in the art would understand the different nutrient and environment requirements of the cells being grown and modify the protocol accordingly. In various embodiments of the invention, the fractionation tank can be used to harvest cells, where the cells are selected from the group consisting of algae, bacteria, yeast and mammalian cells. In various embodiments of the invention, the fractionation tank can be used to harvest gram negative bacterial cells. In various embodiments of the invention, the fractionation tank can be used to harvest bacterial cells, where the bacterial cells are *Escherichia coli*.

A method of harvesting algae comprising generating algae at a site; wherein the site includes a pond containing AGM, wherein the AGM includes one or more species of algae. The site further includes a PDWD, wherein all or a portion of the AGM transported to the PDWD is a GMH, wherein the PDWD fractionates the GMH into at least a top fraction and a bottom fraction. The site further includes a paddle for inducing a flow in the AGM, wherein the AGM flow controls a flow rate of the GMH transported to the PDWD. The site further includes a flow control device for adjusting the bottom fraction removed from the PDWD. The method further comprising adjusting one or both the AGM flow and the flow control device to establish a target AGM concentration. The method further comprising stabilizing one or both the AGM flow and the flow control device setting to maintain a fixed AGM concentration. The method further comprising adjusting one or both the AGM flow and the flow control device to establish a target GMH concentration. The method further comprising stabilizing one or both the AGM flow and the flow control device setting to maintain a fixed GMH concentration. The method further comprising adjusting one or both the AGM flow and the flow control device to establish a target TPDWA concentration. The method further comprising stabilizing one or both the AGM flow and the flow control device setting to maintain a fixed TPDWA concentration.

A method of harvesting a micro organism comprising growing the micro organism at a site; wherein the site includes a vessel containing AGM, wherein the AGM includes the one or more species of micro organisms. The site further includes a PDWD, wherein all or a portion of the AGM transported to the PDWD is a GMH, wherein the PDWD fractionates the GMH into at least a top fraction and a bottom fraction. The site further includes a paddle for inducing a flow in the AGM, wherein the AGM flow controls a flow rate of the GMH transported to the PDWD. The site further includes a flow control device for adjusting the bottom fraction removed from the PDWD. The method further comprising adjusting one or both the AGM flow and the flow control device to establish a target AGM concentration. The method further comprising stabilizing one or both the AGM flow and the flow control device setting to maintain a fixed AGM concentration. The method further comprising adjusting one or both the AGM flow and the flow control device to establish a target GMH concentration. The method further comprising stabilizing one or both the AGM flow and the flow control device setting to maintain a fixed GMH concentration. The method further comprising adjusting one or both the AGM flow and the flow control device to establish a target TPDWA concentration. The method further comprising stabilizing one or both the AGM flow and the flow control device setting to maintain a fixed TPDWA concentration.

A method of fractionating algae grown in media comprising receiving AGM containing one or more species of algae in a PDWD, wherein the GMH enters the PDWD at a first flow rate and fractionating the GMH in the PDWD into at least a top fraction and a bottom fraction, wherein the PDWD fractionates based on at least the first flow rate and a settling time, wherein at least one exit for the top fraction is directed to algaculture. The method further comprising collecting the bottom fraction so as to reduce the ability of the mature cells to slow down growth in the top fraction directed for further algaculture.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

Embodiments of the present invention can include providing code for implementing processes of the present invention. The providing can include providing code to a user in any manner. For example, the providing can include transmitting digital signals containing the code to a user; providing the code on a physical media to a user; or any other method of making the code available.

Embodiments of the present invention can include a computer-implemented method for transmitting the code which can be executed at a computer to perform any of the processes of embodiments of the present invention. The transmitting can include transfer through any portion of a network, such as the Internet; through wires, the atmosphere or space; or any other type of transmission. The transmitting can include initiating a transmission of code; or causing the code to pass into any region or country from another region or country. A transmission to a user can include any transmission received by the user in any region or country, regardless of the location from which the transmission is sent.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

Some aspects of this invention include a method of fractionating algae grown in media comprises receiving aqueous growth media (AGM) containing one or more species of algae in a pond, transferring all or a portion of the AGM comprising growth media to be harvested (GMH) into a primary dewatering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction.

In an embodiment of the invention, a method of fractionating algae grown in media comprises receiving aqueous growth media (AGM) containing one or more species of algae in a pond, transferring all or a portion of the AGM comprising growth media to be harvested (GMH) into a primary dewatering device (PDWD), where the AGM is transferred to the PDWD for between a lower limit of approximately 6 hours per day; and an upper limit of 24 hours per day, where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary dewatering device (PDWD), where the GMH enters the PDWD at a first flow rate, where the first flow rate is set to maintain the top fraction concentration between a lower limit of approximately 0.5 OD; and an upper limit of approximately 2 OD, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary dewatering device (PDWD), where the GMH enters the PDWD at a first flow rate, where the first flow rate is set to maintain the AGM concentration between a lower limit of approximately 0.5 OD; and an upper limit of approximately 2 OD, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary dewatering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction, where the fractionation is based on one or both size and density of at least one of the one or more species of algae.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary dewatering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction, where the settling time is between a lower limit of approximately 30 minutes; and an upper limit of approximately 120 minutes.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary dewatering device (PDWD), where the GMH enters the PDWD at a first flow rate, where the first flow rate is set to maintain the bottom fraction concentration between a lower limit of approximately 1% TS; and an upper limit of approximately 5% TS, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary de-watering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction, further comprising transporting the bottom fraction to a secondary dewatering device at a second transport rate, where the second transport rate is set to maintain the concentration of the bottom fraction between a lower limit of approximately 0.5% TS; and an upper limit of approximately 5% TS.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary de-watering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction, further comprising transporting the bottom fraction to a secondary dewatering device at a second transport rate, where the second transport rate is set to maintain the concentration of the bottom fraction between a lower limit of approximately 0.5% TS and an upper limit of approximately 5% TS, where the second transport rate is set to maintain the concentration of the bottom fraction between a lower limit of approximately 3% TS; and an upper limit of approximately 10% TS.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary de-watering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction, further comprising applying waste heat to the top fraction exiting the PDWD.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary de-watering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction, where the PDWD is an intrachannel fractionation stage.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary de-watering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction, where the PDWD is an intrachannel fractionation stage and where the PDWD is selected from the group consisting of a boat fractionation stage, a vortex fractionation stage, a sidewall separator fractionation stage, a sidechannel fractionation stage and an integral fractionation stage.

In another embodiment of the invention, a method of fractionating algae grown in media comprises receiving aqueous growth media (AGM) containing one or more species of algae in a pond, transferring all or a portion of the AGM comprising growth media to be harvested (GMH) into a primary de-watering device (PDWD), where the GMH enters the PDWD at a first flow rate, fractionating the GMH in the PDWD into at least a top fraction and a bottom fraction, where the PDWD fractionates based on at least the first flow rate and a settling time, where at least one exit for the top fraction is direct to the pond for algaculture, and collecting the bottom fraction, where the PDWD includes tubes to transfer the top fraction to the pond and baffles to collect the bottom fraction, where one or both the tubes and the baffles are one or both heated and cooled by a heat/cold exchanger.

In another aspect of the present invention comprising a system for increasing algal growth by reseeding a pond comprises the pond containing algal growth media (AGM) including one or more species of algae, a primary de-watering device (PDWD), a system of transferring a growth media to be harvested (GMH) consisting of all or a portion of the AGM to the PDWD, where the PDWD separates the GMH into a top primary de-watered algae (TPDWA) and a bottom primary de-watered algae (BPDWA), removing the BPDWA from contact with one or both the TPDWA and the pond to minimize signaling of the BPDWA to one or both the TPDWA and the AGM in the pond to slow growth and reseeding the pond with the TPDWA.

An additional aspect of the present invention comprising a method of harvesting algae comprises generating one or more species of algae at a site; where the site includes a pond containing aqueous growth medium (AGM), where the AGM includes the one or more species of algae; a primary de-watering device (PDWD), where all or a portion of the AGM introduced to the PDWD is a growth media to be harvested (GMH), where the PDWD fractionates the GMH into at least a top fraction and a bottom fraction; a paddle for inducing an AGM, where the AGM flow controls a flow rate of the GMH transported to the PDWD; and a flow control device for adjusting the bottom fraction removed from the PDWD and adjusting one or both the AGM flow and the flow control device so that the concentration of algae in the GMH relative to the concentration of algae in the top fraction is between a lower limit of approximately 5% and an upper limit of approximately 60%.

An additional aspect of the present invention comprising a method of harvesting algae comprises generating one or more species of algae at a site; where the site includes a pond containing aqueous growth medium (AGM), where the AGM includes the one or more species of algae; a primary de-watering device (PDWD), where all or a portion of the AGM introduced to the PDWD is a growth media to be harvested (GMH), where the PDWD fractionates the GMH into at least a top fraction and a bottom fraction; a paddle for inducing an AGM, where the AGM flow controls a flow rate of the GMH transported to the PDWD; and a flow control device for adjusting the bottom fraction removed from the PDWD and adjusting one or both the AGM flow and the flow control device so that the concentration of algae in the GMH relative to the concentration of algae in the top fraction is between a lower limit of approximately 5% and an upper limit of approximately 60%, where the PDWD further includes one or more settling baffles.

An additional aspect of the present invention comprising a method of harvesting algae comprises generating one or more species of algae at a site; where the site includes a pond containing aqueous growth medium (AGM), where the AGM includes the one or more species of algae; a primary de-watering device (PDWD), where all or a portion of the AGM introduced to the PDWD is a growth media to be harvested (GMH), where the PDWD fractionates the GMH into at least a top fraction and a bottom fraction; a paddle for inducing an AGM, where the AGM flow controls a flow rate of the GMH transported to the PDWD; and a flow control device for adjusting the bottom fraction removed from the PDWD and adjusting one or both the AGM flow and the flow control device so that the concentration of algae in the GMH relative to the concentration of algae in the top fraction is between a lower limit of approximately 5% and an upper limit of approximately 60%, where at least the top fraction is heated by a heat exchanger.

An additional aspect of the present invention comprising a method of harvesting algae comprises generating one or more species of algae at a site; where the site includes a pond containing aqueous growth medium (AGM), where the AGM includes the one or more species of algae; a primary de-watering device (PDWD), where all or a portion of the AGM introduced to the PDWD is a growth media to be harvested (GMH), where the PDWD fractionates the GMH into at least a top fraction and a bottom fraction; a paddle for inducing an AGM, where the AGM flow controls a flow rate of the GMH transported to the PDWD; and a flow control device for adjusting the bottom fraction removed from the PDWD and adjusting one or both the AGM flow and the flow control device so that the concentration of algae in the GMH relative to the concentration of algae in the top fraction is between a lower limit of approximately 5% and an upper limit of approximately 60%, where the heat exchanger is located in the PDWD and the heat exchanger heats at least the GMH entering the fractionation tank.

An additional aspect of the present invention comprising a method of harvesting algae comprises generating one or more species of algae at a site; where the site includes a pond containing aqueous growth medium (AGM), where the AGM includes the one or more species of algae; a primary de-watering device (PDWD), where all or a portion of the AGM introduced to the PDWD is a growth media to be harvested (GMH), where the PDWD fractionates the GMH into at least a top fraction and a bottom fraction; a paddle for inducing an AGM, where the AGM flow controls a flow rate of the GMH transported to the PDWD; and a flow control device for adjusting the bottom fraction removed from the PDWD and adjusting one or both the AGM flow and the flow control device so that the concentration of algae in the GMH relative to the concentration of algae in the top fraction is between a lower limit of approximately 5% and an upper limit of approximately 60%, where the heat exchanger is located in the fractionation tank and the heat exchanger heats the GMH entering the PDWD.

What is claimed is:

1. A method of fractionating algae comprising the steps of:
   (a) receiving an aqueous growth medium (AGM) containing one or more species of algae at a pond;
   (b) transferring all or a portion of the AGM comprising growth media to be harvested (GMH) into a primary de-watering device (PDWD) which includes one or more baffles, one or more inlets and a plurality of outlets, where the GMH enters the PDWD at a first flow rate;
   (c) fractionating the GMH in the PDWD into at least a top fraction and a bottom fraction, where at least one outlet is an exit for the top fraction, where the top fraction exits at a second flow rate, where the PDWD fractionates based on at least the first flow rate, the second flow rate and a settling time;
   (d) adjusting a flow control device adapted to remove the bottom fraction from the PDWD through at least one of the plurality of outlets of the PDWD; and
   (e) removing the bottom fraction through at least one of the plurality of outlets of the PDWD.

2. The method of claim 1, where the AGM is transferred to the PDWD for between:
   a lower limit of approximately 6 hours per day; and
   an upper limit of 24 hours per day.

3. The method of claim 1, where the first flow rate is set to maintain the top fraction concentration between:
   a lower limit of approximately 0.5 OD; and
   an upper limit of approximately 2 OD.

4. The method of claim 1, where the second flow rate is set to maintain the top fraction concentration between:
   a lower limit of approximately 0.5 OD; and
   an upper limit of approximately 2 OD.

5. The method of claim 1, where the first flow rate is set to maintain the AGM concentration between:
   a lower limit of approximately 0.5 OD; and
   an upper limit of approximately 2 OD.

6. The method of claim 1, where the second flow rate is set to maintain the AGM concentration between:
   a lower limit of approximately 0.5 OD; and
   an upper limit of approximately 2 OD.

7. The method of claim 1, where the fractionation of the GMH is carried out based on a characteristic of at least one of the one or more species of algae, the characteristic selected from the group consisting of flotation characteristics, size and density.

8. The method of claim 1, where the settling time is between:
   a lower limit of approximately 30 minutes; and
   an upper limit of approximately 120 minutes.

9. The method of claim 1, where the first flow rate is set to maintain the bottom fraction concentration between:
   a lower limit of approximately 1% TS; and
   an upper limit of approximately 5% TS.

10. The method of claim 1, where the second flow rate is set to maintain the bottom fraction concentration between:
    a lower limit of approximately 1% TS; and
    an upper limit of approximately 5% TS.

11. The method of claim 1, where second flow rate is set to maintain the concentration of the bottom fraction between:
    a lower limit of approximately 3% TS; and
    an upper limit of approximately 10% TS.

12. The method of claim 1, further comprising applying waste heat to the top fraction exiting the PDWD.

13. The method of claim 1, where the PDWD is an intrachannel fractionation stage.

14. The method of claim 13, where the PDWD is selected from the group consisting of a boat fractionation stage, a vortex fractionation stage, a sidewall separator fractionation stage, a sidechannel fractionation stage and an integral fractionation stage.

15. The method of claim 1, further comprising heating the top fraction using a heat exchanger located in the PDWD.

16. The method of claim 1, where the first flow rate and the second flow rate are adjusted so that the concentration of algae in the top fraction returned to the pond is between:
   a lower limit of approximately 5 percent; and
   an upper limit of approximately 60 percent of the concentration of algae in the GMH.

17. The method of claim 1, where the first flow rate and the second flow rate are set to maintain the concentration of algae in the top fraction returned to the pond between:
   a lower limit of approximately 0.5 Optical Density; and
   an upper limit of approximately 2 Optical Density.

18. The method of claim 1, where the first flow rate and the second flow rate are set to maintain the AGM concentration between:
   a lower limit of approximately 0.5 Optical Density; and
   an upper limit of approximately 2 Optical Density.

19. A method of fractionating algae comprising the steps of:
   (a) receiving an aqueous growth medium (AGM) containing one or more species of algae;
   (b) transferring all or a portion of the AGM comprising growth media to be harvested (GMH) into a primary de-watering device (PDWD) which includes one or more baffles, one or more inlets and a plurality of outlets, where the GMH is transferred at a first flow rate; and
   (c) fractionating the GMH in the PDWD into at least a top fraction and a bottom fraction, where at least one outlet is an exit for the top fraction, where the top fraction exits at a second flow rate, where the PDWD fractionates based on at least the first flow rate, the second flow rate and a settling time, where the top fraction concentration flowing out of the PDWD is between:
   a lower limit of approximately 0.5 OD; and
   an upper limit of approximately 2 OD.

20. A method of fractionating algae comprising the steps of:
   (a) receiving an aqueous growth medium (AGM) containing one or more species of algae;
   (b) transferring all or a portion of the AGM comprising growth media to be harvested (GMH) into a primary de-watering device (PDWD) which includes one or more baffles, one or more inlets and a plurality of outlets, where the GMH is transferred at a first flow rate;
   (c) fractionating the GMH in the PDWD into at least a top fraction and a bottom fraction, where at least one outlet is an exit for the top fraction, where the top fraction exits at a second flow rate, where the PDWD fractionates based on at least the first flow rate, the second flow rate and a settling time;
   (d) adjusting a flow control device adapted to remove the bottom fraction from the PDWD through at least one of the plurality of outlets of the PDWD, where the bottom fraction exits at a third flow rate; and
   (e) removing the bottom fraction through at least one of the plurality of outlets of the PDWD, where the concentration of the bottom fraction is between:
   a lower limit of approximately 0.5% TS; and
   an upper limit of approximately 5% TS.

* * * * *